(12) United States Patent  
Nishide et al.

(10) Patent No.: US 11,492,313 B2  
(45) Date of Patent: Nov. 8, 2022

(54) ORGANIC COMPOUND AND ORGANIC LIGHT-EMITTING ELEMENT

(71) Applicant: CANON KABUSHIKI KAISHA, Tokyo (JP)

(72) Inventors: Yosuke Nishide, Kawasaki (JP); Naoki Yamada, Inagi (JP); Jun Kamatani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 336 days.

(21) Appl. No.: 16/886,354

(22) Filed: May 28, 2020

(65) Prior Publication Data

US 2020/0377433 A1  Dec. 3, 2020

(30) Foreign Application Priority Data

May 31, 2019 (JP) .............................. JP2019-102197

(51) Int. Cl.
  *C07C 13/64* (2006.01)
  *H01L 51/00* (2006.01)
  (Continued)

(52) U.S. Cl.
  CPC ................ *C07C 13/64* (2013.01); *C07F 5/04* (2013.01); *H01L 51/0054* (2013.01);
  (Continued)

(58) Field of Classification Search
  CPC ............. H01L 51/0072; H01L 51/0061; H01L 51/5012; H01L 51/5016; H01L 51/0073;
  (Continued)

(56) References Cited

U.S. PATENT DOCUMENTS 7,993,760 B2 *  8/2011  Komori .................... C09B 11/04  
  428/917  
9,126,970 B2 *  9/2015  Pflumm ............... C07D 403/14  
  (Continued)

FOREIGN PATENT DOCUMENTS

JP  2013-139426 A  7/2013

*Primary Examiner* — Vu A Vu  
(74) *Attorney, Agent, or Firm* — Canon U.S.A., Inc., IP Division

(57) ABSTRACT

An organic compound is represented by formula (1). In the formula (1), $R_1$ to $R_{24}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

18 Claims, 8 Drawing Sheets

(51) Int. Cl.
*C07F 5/04* (2006.01)
*H01L 51/50* (2006.01)

(52) U.S. Cl.
CPC ...... *H01L 51/0056* (2013.01); *H01L 51/0073* (2013.01); *H01L 51/5012* (2013.01)

(58) Field of Classification Search
CPC ............. H01L 51/0052; H01L 51/0059; H01L 51/0067; H01L 51/0054; H01L 51/0056; H01L 51/0008; H01L 51/0085; H01L 51/5024; C07D 487/06; C09K 11/06; C09K 2211/1018; C07C 13/64; C07C 15/20; C07C 25/22; C07C 255/52; C07C 255/54; C07F 5/04
USPC .......................................................... 257/40
See application file for complete search history.

(56) References Cited

U.S. PATENT DOCUMENTS

| | | | | |
|---|---|---|---|---|
| 9,466,801 | B2 * | 10/2016 | Cho | .................... H01L 51/0067 |
| 10,316,013 | B2 * | 6/2019 | Kim | .................... H01L 51/0072 |
| 11,130,747 | B2 * | 9/2021 | Shim | .................... C07D 495/04 |
| 11,299,459 | B2 * | 4/2022 | Mun | .................... C07D 495/04 |
| 2016/0020412 | A1 * | 1/2016 | Kim | .................... H01L 51/0085 |
| | | | | 257/40 |
| 2016/0087224 | A1 * | 3/2016 | Kim | .................... H01L 51/0072 |
| | | | | 257/40 |

\* cited by examiner

FIG. 1

| | STRUCTURAL FORMULA | MOLECULAR WEIGHT OF BASIC SKELETON | SYMMETRY OF BASIC SKELETON | POINT GROUP | SUBLIMABILITY |
|---|---|---|---|---|---|
| COMPARATIVE COMPOUND 2-A | | 501 | (TOP) | $D_{2h}$ | DECOMPOSED AFTER SUBLIMATION |
| COMPARATIVE COMPOUND 1-B | | 575 | (TOP) (HORIZONTAL) | $C_{2v}$ | NOT DECOMPOSED AFTER SUBLIMATION |
| EXEMPLARY COMPOUND A2 | | 649 | (TOP) (HORIZONTAL) 14° | $C_1$ | NOT DECOMPOSED AFTER SUBLIMATION |

ORGANIC COMPOUND AND ORGANIC LIGHT-EMITTING ELEMENT

BACKGROUND OF THE INVENTION

Field of the Invention

The present disclosure relates to an organic compound and an organic light-emitting element including the organic compound.

Description of the Related Art

Organic light-emitting elements (organic electroluminescent elements (organic EL elements)) are electronic elements including a pair of electrodes and an organic compound layer disposed between the electrodes. By injecting electrons and holes through the pair of electrodes, excitons of a luminescent organic compound in the organic compound layer are generated. The organic light-emitting elements emit light when the excitons return to their ground state.

Recent remarkable progress in organic light-emitting elements can achieve low driving voltage, various emission wavelengths, high-speed response, and reductions in the thickness and weight of light-emitting devices.

The standards of sRGB and AdobeRGB have been used as a color reproduction range used for displays, and materials that reproduce the color reproduction range have been demanded. In recent years, BT-2020 has been further selected as the standard that widens the color reproduction range.

Organic compounds having light-emitting properties have been enthusiastically created to date. This is because it is important to create compounds having good light-emitting properties in order to provide high-performance organic light-emitting elements. Japanese Patent Laid-Open No. 2013-139426 discloses a compound 1-A below as a compound that has been created so far.

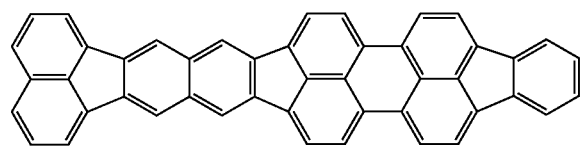

1-A

An organic light-emitting element including the compound disclosed in Japanese Patent Laid-Open No. 2013-139426 is difficult to reproduce the chromaticity coordinates of red in the color reproduction range of BT-2020. Thus, compounds that emit red light at longer wavelengths are required.

SUMMARY OF THE INVENTION

Accordingly, the present disclosure provides an organic compound that emits red light having longer wavelengths. The present disclosure also provides an organic compound that emits light in a red region with a high color purity. The present disclosure also provides an organic light-emitting element having high light emission efficiency and high driving durability. An organic compound according to the present disclosure is represented by formula (1) below.

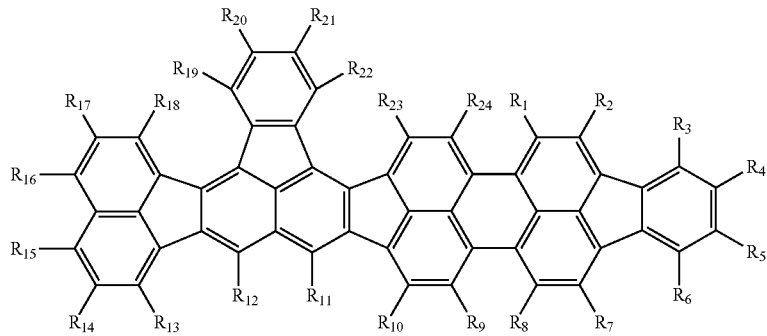

(1)

In the formula (1), $R_1$ to $R_{24}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

Further features of the present disclosure will become apparent from the following description of exemplary embodiments with reference to the attached drawings.

BRIEF DESCRIPTION OF THE DRAWINGS

FIG. 1 illustrates the planarity and sublimability of compounds.

DESCRIPTION OF THE EMBODIMENTS

Organic Compound

Figure 2:
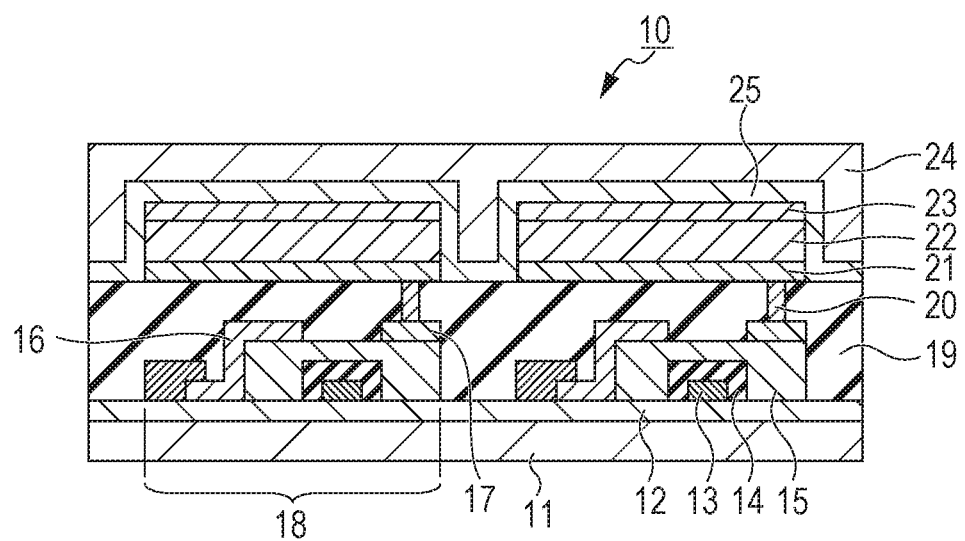
FIG. 2 is a schematic sectional view illustrating an example of a display apparatus according to this embodiment.

An organic compound according to this embodiment will be described. The organic compound according to this embodiment is represented by formula (1) below.

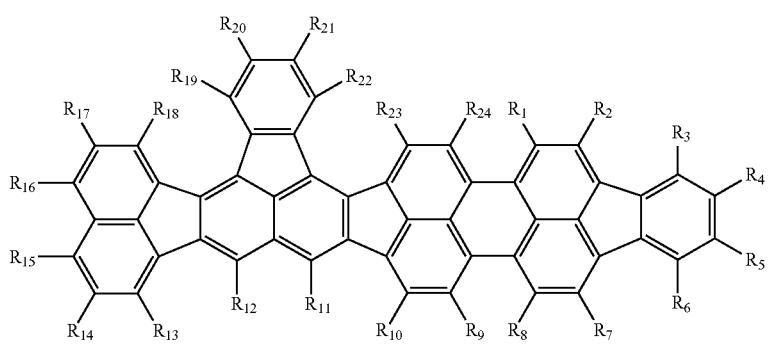

(1)

In the formula (1), $R_1$ to $R_{24}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group. $R_1$ to $R_{24}$ are preferably each independently selected from the group consisting of a hydrogen atom, a substituted or unsubstituted alkyl group, and a substituted or unsubstituted aryl group. $R_1$ to $R_{24}$ are more preferably each independently selected from the group consisting of a hydrogen atom and a substituted or unsubstituted aryl group.

In this specification, the term "basic skeleton" refers to a skeleton in which all of $R_1$ to $R_{24}$ of the compound represented by the formula (1) are hydrogen atoms.

Non-limiting examples of the halogen atom represented by $R_1$ to $R_{24}$ include fluorine, chlorine, bromine, and iodine.

Non-limiting examples of the alkyl group represented by $R_1$ to $R_{24}$ include a methyl group, an ethyl group, a n-propyl group, an isopropyl group, a n-butyl group, a tert-butyl group, a sec-butyl group, an octyl group, a cyclohexyl group, an 1-adamantyl group, and an 2-adamantyl group. The alkyl group is preferably an alkyl group having 1 to 10 carbon atoms and more preferably an alkyl group having 1 to 4 carbon atoms.

Non-limiting examples of the alkoxy group represented by $R_1$ to $R_{24}$ include a methoxy group, an ethoxy group, a propoxy group, an 2-ethyl-hexyloxy group, and a benzyloxy group. The alkoxy group may be an alkoxy group having 1 to 6 carbon atoms.

Non-limiting examples of the amino group represented by $R_1$ to $R_{24}$ include an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, an N-phenyl-N-(4-trifluoromethylphenyl)amino group, and an N-piperidyl group.

Non-limiting examples of the aryl group represented by $R_1$ to $R_{24}$ include a phenyl group, a naphthyl group, an indenyl group, a biphenyl group, a terphenyl group, a fluorenyl group, a phenanthryl group, and a triphenylenyl group. The aryl group may be an aryl group having 6 to 18 carbon atoms.

Non-limiting examples of the heterocyclic group represented by $R_1$ to $R_{24}$ include a pyridyl group, an oxazolyl group, an oxadiazolyl group, a thiazolyl group, a thiadiazolyl group, a carbazolyl group, an acridinyl group, a phenanthrolyl group, a dibenzofuranyl group, and a dibenzothiophenyl group. The heterocyclic group may be a heterocyclic group having 3 to 15 carbon atoms.

Non-limiting examples of the aryloxy group represented by $R_1$ to $R_{24}$ include a phenoxy group and a thienyloxy group.

Non-limiting examples of the silyl group represented by $R_1$ to $R_{24}$ include a trimethylsilyl group and a triphenylsilyl group.

Non-limiting examples of a substituent that may be further included in the alkyl group, the alkoxy group, the amino group, the aryl group, the heterocyclic group, and the aryloxy group include alkyl groups such as a methyl group, an ethyl group, a n-propyl group, an isopropyl group, a n-butyl group, and a tert-butyl group; aralkyl groups such as a benzyl group; aryl groups such as a phenyl group and a biphenyl group; heterocyclic groups such as a pyridyl group and a pyrrolyl group; amino groups such as a dimethylamino group, a diethylamino group, a dibenzylamino group, a diphenylamino group, and a ditolylamino group; alkoxy groups such as a methoxy group, an ethoxy group, and a propoxy group; aryloxy groups such as a phenoxy group; halogen atoms such as fluorine, chlorine, bromine, and iodine; and cyano groups. The substituent is preferably a halogen atom or a substituted or unsubstituted alkyl group, more preferably an alkyl group having 1 to 10 carbon atoms or a substituted or unsubstituted aryl group, more preferably an aryl group having 6 to 12 carbon atoms or a substituted or unsubstituted heterocyclic group, and more preferably a heterocyclic group having 3 to 9 carbon atoms or a cyano group.

In the organic compound according to this embodiment, when a group other than the hydrogen atom, such as a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, or a cyano group, is introduced to the basic skeleton, a compound whose concentration quenching is suppressed, which has an improved sublimability when sublimated, and which has an improved solvent solubility when coated can be obtained.

Next, a method for synthesizing the organic compound according to this embodiment will be described. The organic compound according to this embodiment is synthesized through, for example, a reaction scheme shown below.

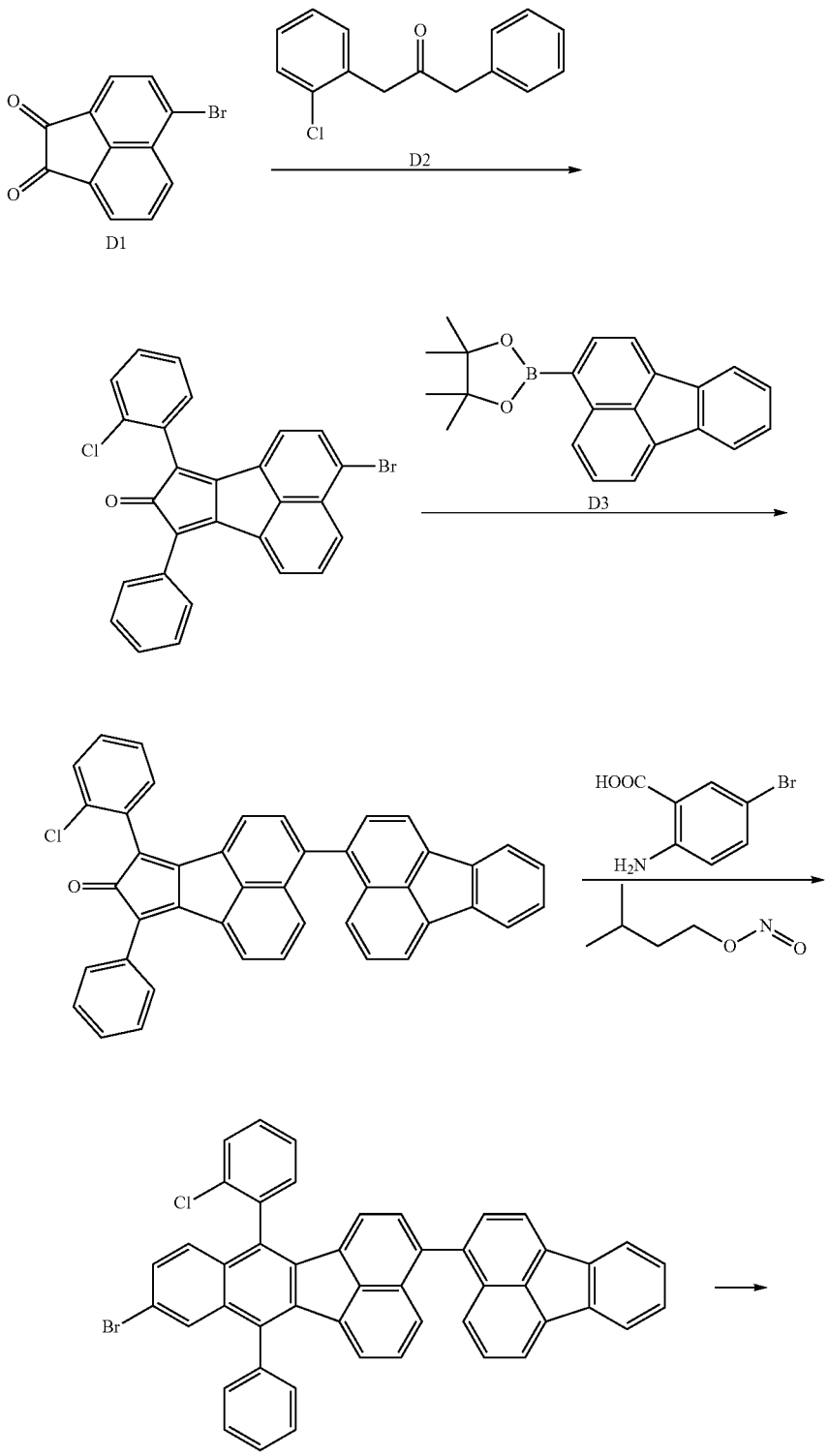

-continued
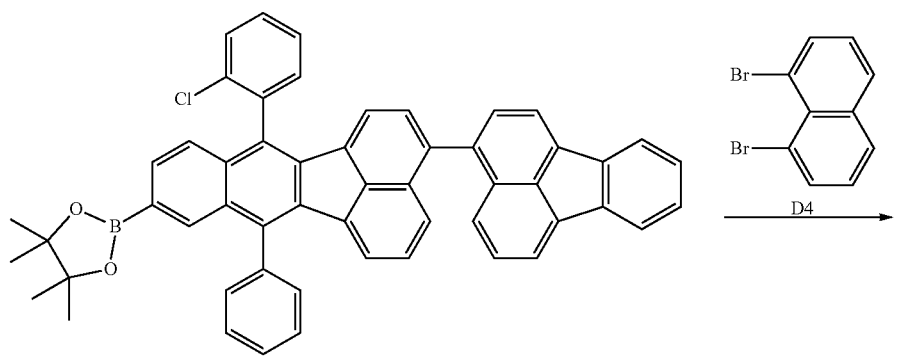
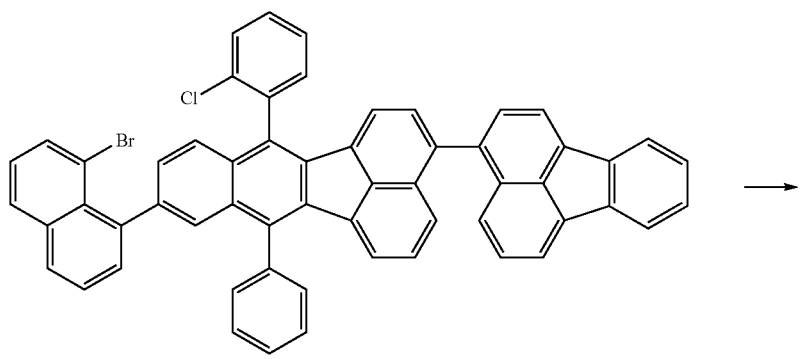
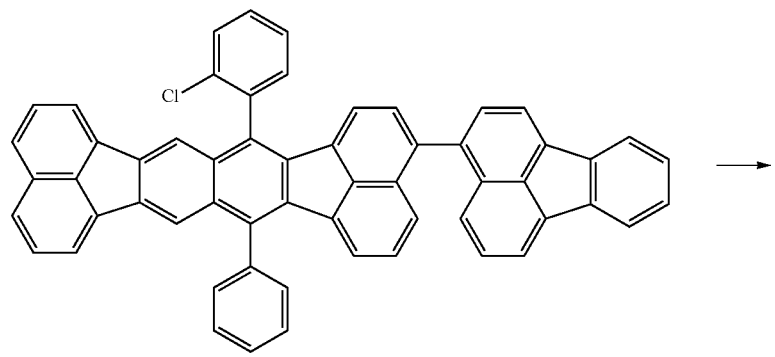
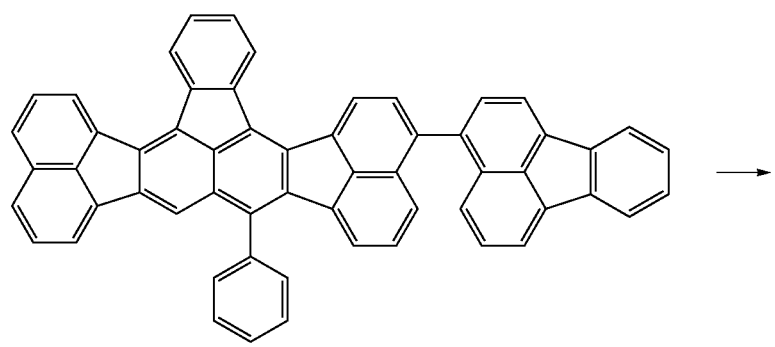

-continued

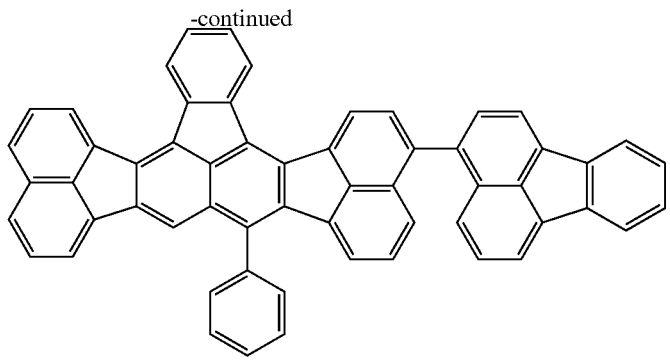

As shown in the above synthesis scheme, the organic compound according to this embodiment is synthesized using the following compounds (a) to (d) as raw materials.
(a) Acenaphthenequinone derivative (D1)
(b) Dibenzyl ketone derivative (D2)
(c) Fluoranthene derivative (D3)
(d) Naphthalene derivative (D4)

By appropriately introducing a substituent to the compounds (a) to (d), hydrogen atoms at any of $R^1$ to $R^{24}$ in the formula (1) are substituted with particular groups other than the hydrogen atom. Furthermore, various organic compounds can be synthesized by changing the compounds D1 to D4 in the above synthesis scheme.

The organic compound according to this embodiment is a stable compound that emits red light with a high color purity because the organic compound has the following features. Furthermore, the use of this organic compound can provide an organic light-emitting element having high light emission efficiency and high durability. The basic skeleton of the organic compound according to this embodiment has an electron-deficient π conjugation, which decreases the HOMO and LUMO energy levels. Thus, the basic skeleton has high electron acceptability.
(1) The emission wavelength of the basic skeleton itself is in a red region with a high color purity.
(2) The compound has an asymmetric structure and thus has low crystallinity.
(3) The HOMO energy is low and the compound itself has high chemical stability.

Hereafter, these features will be described. The dihedral angle of the molecular structure shown in Table 4 was calculated by using the following molecular orbital calculations.

The density functional theory (DFT), which has been widely used today, was used as a calculation technique of the molecular orbital calculations. The functional was B3LYP and the basis function was 6-31G*. The molecular orbital calculations were conducted by using Gaussian09 (Gaussian09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford Conn., 2010.), which has been widely used today.

(1) The Emission Wavelength of the Basic Skeleton Itself is in a Red Region with a High Color Purity In the organic compound represented by the formula (1), the present inventors have focused on the basic skeleton itself. Specifically, the present inventors have attempted to provide a compound in which the emission wavelength of a molecule having only a basic skeleton is within a desired emission wavelength region. In this embodiment, the desired emission wavelength region is a red region with a high color purity, which is specifically a region in which the maximum emission wavelength is 590 nm or more and 650 nm or less in a dilute solution.

Next, the properties of the basic skeleton of the organic compound according to an embodiment of the present disclosure will be described by comparing comparative compounds having a structure similar to that of the organic compound according to an embodiment of the present disclosure. Specifically, the comparative compound is a comparative compound 1-B below.

1-B

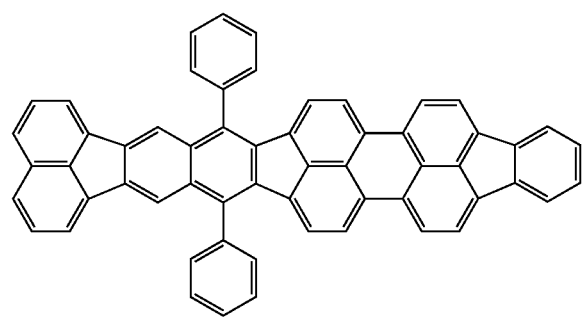

Herein, one of the organic compounds according to an embodiment of the present disclosure is an exemplary compound A2 which has a basic skeleton represented by the formula (1) and in which $R_1$ to $R_{10}$ and $R_{12}$ to $R_{24}$ represent a hydrogen atom and $R_{11}$ represents a phenyl group.

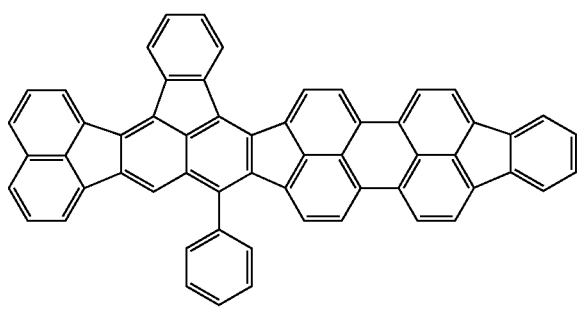

A2

The present inventors compared the comparative compound 1-B and the exemplary compound A2 according to an embodiment of the present disclosure in terms of measured maximum emission wavelength. Table 1 shows the results. The emission wavelength was determined by photoluminescence measurement of a diluted toluene solution at an excitation wavelength of 350 nm at room temperature using an F-4500 manufactured by Hitachi, Ltd.

the present disclosure is capable of emitting light with a high color purity that can reproduce deep red. The chromaticity coordinates of red will be described in detail in Examples.

(2) The Compound has an Asymmetric Structure and Thus has Low Crystallinity

The conjugation length of the organic compound according to an embodiment of the present disclosure is increased such that the emission wavelength region of the basic skeleton itself is a red region. Since molecules having a large conjugation length generally have high molecular planarity, the degree of molecular packing increases. The molecular packing unfavorably increases the crystallinity, which deteriorates sublimability and causes concentration quenching. Therefore, the present inventors have focused on the symmetry of the molecular structure. The molecular arrangement of molecules having low symmetry is more easily disturbed when the molecules are solidified than that of molecules having high symmetry, which suppresses molecular packing in which molecules regularly overlap each other.

In this embodiment, the exemplary compound A2 according to this embodiment, the comparative compound 1-B, and

TABLE 1

| Name of compound | Molecular structure | Actual measurement Maximum emission wavelength/nm |
|---|---|---|
| Comparative compound 1-B | 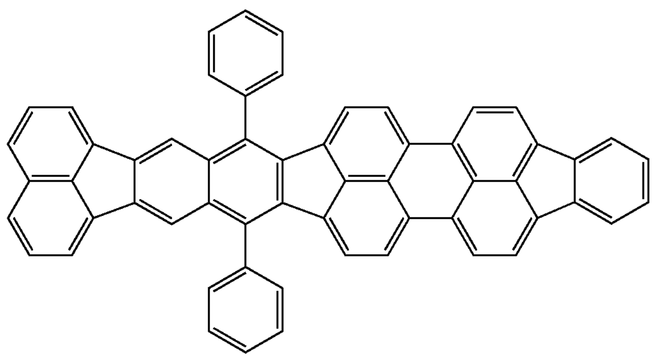 [SMILES: c1ccc(-c2c3cc4c(cc3c(-c3ccccc3)c3c5ccc6c7ccc8c9c(ccc(c%10ccc(c23)c5c%106)c97)-c2ccccc2-8)c2cccc3cccc4c32)cc1] | 588 |
| Exemplary compound A2 | 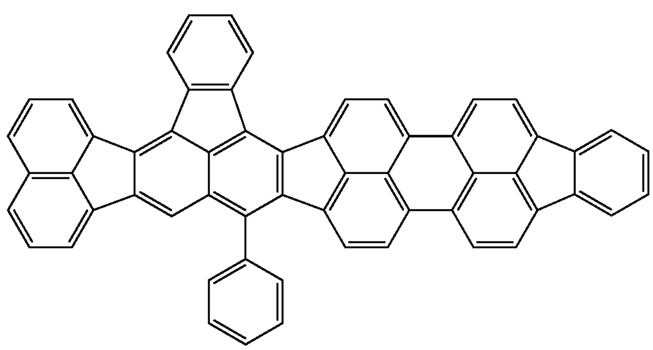 [SMILES: c1ccc(-c2c3cc4c5cccc6cccc(c65)c4c4c5ccccc5c(c5c6ccc7c8ccc9c%10c(ccc(c%11ccc(c25)c6c%117)c%108)-c2ccccc2-9)c34)cc1] | 598 |

Table 1 shows that the emission color of the comparative compound 1-B is red, but is not in the desired range. In contrast, the exemplary compound A2 has a maximum emission wavelength in the desired range, and thus exhibits a long-wavelength red emission color that is suitable for red in the display standard such as BT-2020. The same applies to the exemplary compound A1 that is a basic skeleton itself. Therefore, the basic skeleton according to an embodiment of the comparative compound 2-A were compared with each other using a group theory in terms of symmetry of the molecular structure of the basic skeleton. The comparative compound 2-A was used for comparison as an example of the organic compound that has high symmetry and emits red light.

As illustrated in FIG. 1, the basic skeleton of the comparative compound 2-A has a two-fold rotation axis (C2) in a direction perpendicular to the molecular plane, and also has a two-fold rotation axis (C2) and a symmetry plane ($\sigma_h$) that are orthogonal to the above two-fold rotation axis. Therefore, the point group is classified into $D_{2h}$. The basic skeleton of the comparative compound 1-B has a two-fold rotation axis (C2) in a major axis direction of the molecular plane and a symmetry plane ($\sigma_v$) including the two-fold rotation axis, and therefore the point group is classified into $C_{2v}$.

On the other hand, the basic skeleton of the exemplary compound A2 according to an embodiment of the present disclosure does not have a rotation axis or a symmetry plane ($\sigma$) including a molecular plane. Therefore, the point group is classified into $C_1$. This is because the basic skeleton of the exemplary compound A2 according to an embodiment of the present disclosure is twisted by about 14° by steric repulsion in a molecule.

Therefore, the molecular symmetry is lower in the exemplary compound A2 than in the comparative compound 2-A and the comparative compound 1-B.

Molecules having low symmetry have high sublimability because the molecular packing is suppressed and the crystallinity reduces. Compared with the comparative compound 2-A and the comparative compound 1-B, the exemplary compound A2 is considered to be a compound that is disadvantageous in terms of sublimability because the molecular weight of the basic skeleton increases and the molecular planarity increases. However, the decomposition has not been observed even after sublimation. On the other hand, the comparative compound 2-A has a small molecular weight, but high symmetry. Therefore, the molecular packing is facilitated, which increases the sublimation temperature to a temperature close to the decomposition temperature of the compound. Thus, it is believed that the decomposition after sublimation has been observed. The decomposition before and after sublimation is determined by whether the purity after sublimation is decreased. The purity was measured by high-performance liquid chromatography using an instrument manufactured by JASCO Corporation.

Furthermore, the exemplary compound A2 has a longer distance between molecules in a solid state than the comparative compound 1-B because of its twisted basic skeleton and thus the molecular packing is suppressed. Therefore, the exemplary compound A2 has higher sublimability.

The organic compound according to an embodiment of the present disclosure includes a molecule having low symmetry and has a twisted portion in the basic skeleton. Therefore, the organic compound is a compound whose molecular packing can be suppressed and whose sublimability can be maintained while the basic skeleton has a conjugation length having a light-emitting region in a long-wavelength range.

(3) The HOMO Energy is Low and the Compound Itself has High Chemical Stability

In the creation of a material having a desired emission wavelength region, the present inventors have focused on the HOMO energy of molecules. An emission wavelength region on the longer wavelength side means a narrow band gap. Therefore, the HOMO energy needs to be increased or the LUMO energy needs to be decreased. Herein, high HOMO energy means that the energy level is close to the vacuum level and low HOMO energy means that the energy level is far from the vacuum level. As is clear from Table 2, the exemplary compound A2 according to an embodiment of the present disclosure has a lower HOMO energy than the comparative compound 1-B. That is, the exemplary compound A2 according to an embodiment of the present disclosure has a higher oxidation resistance. Furthermore, the organic compound according to an embodiment of the present disclosure has low HOMO and LUMO energy levels, and an emission wavelength region on the longer wavelength side is achieved as shown in Table 1. This is because a molecular design having a fused-ring structure with increased conjugation length is provided so that three electron-attracting five-membered rings are present in the basic skeleton. Therefore, a compound having low HOMO and LUMO energy levels, that is, the organic compound according to this embodiment has high oxidation resistance.

TABLE 2

| Name of compound | Molecular structure | Calculated value HOMO/eV |
|---|---|---|
| Comparative compound 1-B | 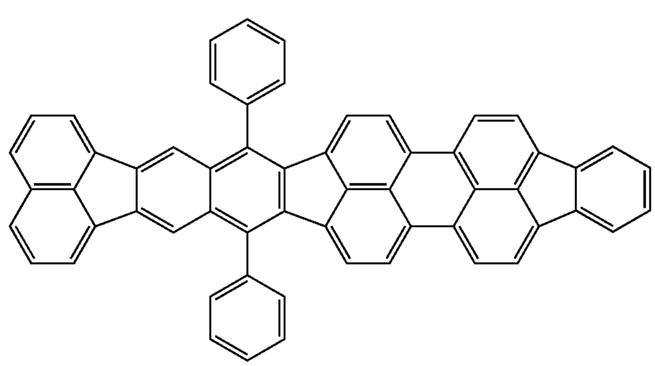 | −4.85 |

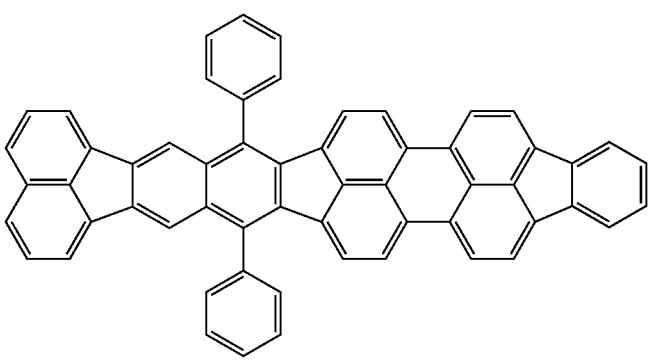 [SMILES: c1ccc(-c2c3cc4c(cc3c(-c3ccccc3)c3c5ccc6c7ccc8c9c(ccc(c%10ccc(c23)c5c%106)c97)-c2ccccc2-8)c2cccc3cccc4c32)cc1]

TABLE 2-continued

| Name of compound | Molecular structure | Calculated value HOMO/eV |
|---|---|---|
| Exemplary compound A2 | 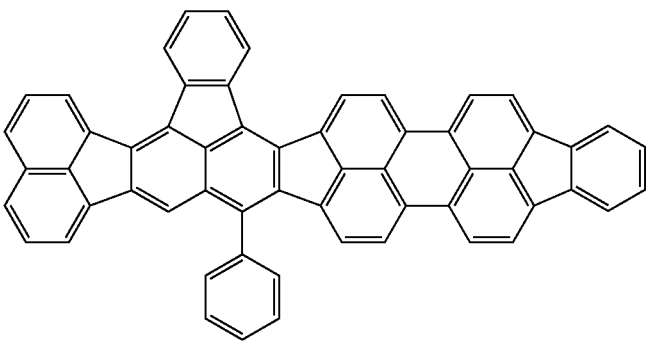 [SMILES: c1ccc(-c2c3cc4c5cccc6cccc(c65)c4c4c5ccccc5c(c5c6ccc7c8ccc9c%10c(ccc(c%11ccc(c25)c6c%117)c%108)-c2ccccc2-9)c34)cc1] | −4.96 |

Table 2 shows that the comparative compound 1-B has a high HOMO energy of −4.85 eV whereas the exemplary compound A2 according to an embodiment of the present disclosure has a low HOMO energy of −4.96 eV. This shows that the exemplary compound A2 according to an embodiment of the present disclosure is a compound whose emission wavelength is increased, but which is not easily oxidized compared with the comparative compound 1-B.

The organic compound according to this embodiment has high oxidation resistance and thus an organic light-emitting element that uses such a compound has high stability and high durability.

Furthermore, an organic compound that satisfies the following condition (4) may be used for organic light-emitting elements. This is because when the condition (4) is satisfied, an effect of suppressing the molecular packing is further increased, which can improve the sublimability and can suppress the concentration quenching. The improvement in sublimability can increase the purity of a material through sublimation purification and enables the production of an organic light-emitting element by vapor deposition. This can decrease the amount of impurities contained in the organic light-emitting element. Thus, a decrease in light emission efficiency due to impurities and a decrease in driving durability can be suppressed. The concentration quenching can also be suppressed from the viewpoint of improving the light emission efficiency of the organic light-emitting element.

(4) The Organic Compound has a Group Other than a Hydrogen Atom at any of $R_{11}$ and $R_{12}$ Hereafter, this condition will be described.

(4) The Organic Compound has a Group Other than a Hydrogen Atom at any of $R_{11}$ and $R_{12}$ In the organic compound according to an embodiment of the present disclosure, the crystallinity of the molecule itself due to intermolecular stacking can be reduced to some degree by introducing a group other than the hydrogen atom to $R_1$ to $R_{24}$. The reduction in crystallinity leads to suppressing the intermolecular concentration quenching and improving the sublimability. The organic compound according to an embodiment of the present disclosure has high planarity because of the increase in wavelength. Therefore, if all of $R_1$ to $R_{24}$ represent groups other than the hydrogen atom, the intermolecular stacking readily occurs. Accordingly, the substitution position at which the intermolecular stacking can be effectively suppressed will be described.

Table 3 shows a dihedral angle between the basic skeleton and a phenyl group introduced to each of $R_1$ to $R_{24}$, that is, the degree of twisting therebetween. At the substitution positions $R_{11}$ and $R_{12}$, hydrogen at an ortho position of the phenyl group and hydrogen of the basic skeleton cause a large steric repulsion and thus the dihedral angle is as large as 90° as shown in Table 3. Therefore, the planarity on the whole molecule is lost. This effect leads to prevention of intermolecular stacking, reduction in crystallinity, suppression of intermolecular concentration quenching, and improvement in sublimability. As the dihedral angle decreases, the degree of twisting decreases and the conjugation is further extended between the basic skeleton and the groups represented by $R_1$ to $R_{24}$. Therefore, the emission wavelength can be further shifted to longer wavelengths.

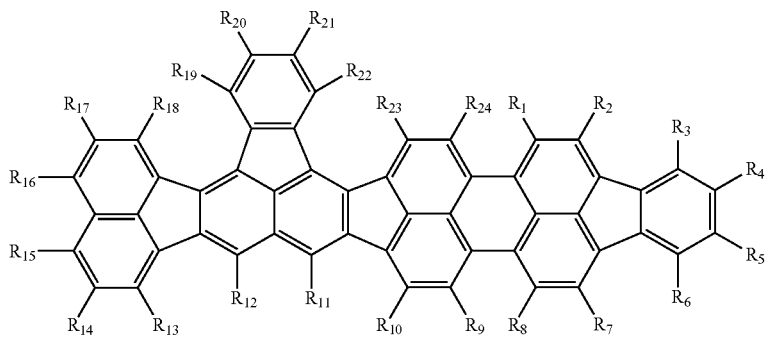

TABLE 3

| Substitution position | $R_1$ $R_8$ | $R_2$ $R_7$ | $R_3$ $R_6$ | $R_4$ $R_5$ | $R_9$ $R_{24}$ | $R_{10}$ | $R_{11}$ $R_{12}$ |
|---|---|---|---|---|---|---|---|
| Dihedral angle/° | 68 | 56 | 58 | 17 | 68 | 57 | 90 |
| Substitution position | $R_{13}$ | $R_{14}$ $R_{17}$ | $R_{15}$ $R_{16}$ | $R_{18}$ $R_{23}$ | $R_{19}$ $R_{22}$ | $R_{20}$ $R_{21}$ | |
| Dihedral angle/° | 56 | 17 | 59 | 42 | 41 | 38 | |

Accordingly, a group other than the hydrogen atom, such as a bulky group or a group having a bulky substituent, may be introduced to at least one selected from $R_{11}$ and $R_{12}$. The group other than the hydrogen atom is a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, or a cyano group and is preferably a substituted or unsubstituted alkyl group or a substituted or unsubstituted aryl group. At least one selected from $R_{11}$ and $R_{12}$ is preferably an aryl group having a substituent and more preferably an aryl group having a substituent at an ortho position. At least one selected from $R_{11}$ and $R_{12}$ is also preferably a substituted or unsubstituted phenyl group.

Since the organic compound according to an embodiment of the present disclosure has the above properties (1) to (3), the emission wavelength of the basic skeleton itself is a red color with a high color purity, the compound itself has high chemical stability, and the sublimability is maintained compared with the comparative compounds. Furthermore, when the organic compound has the property (4), the intermolecular stacking is suppressed, which can improve the sublimability and suppress the concentration quenching. By using such an organic compound, an organic light-emitting element that has high efficiency and high durability and that emits red light with a high color purity can be provided.

Specific examples of the organic compound according to an embodiment of the present disclosure are shown below. The organic compound according to an embodiment of the present disclosure is not limited thereto.

A1

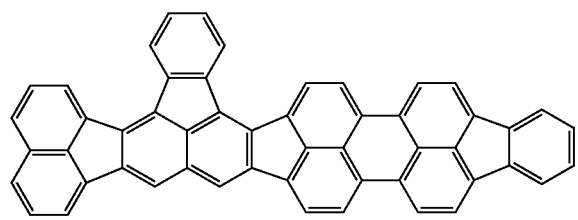

A2

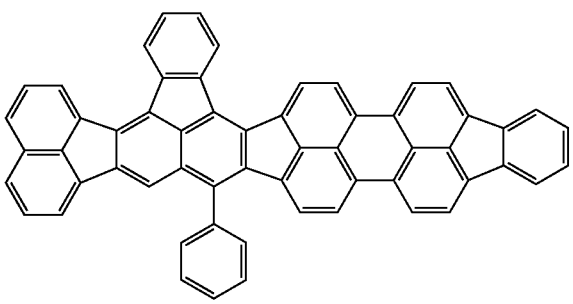

A3

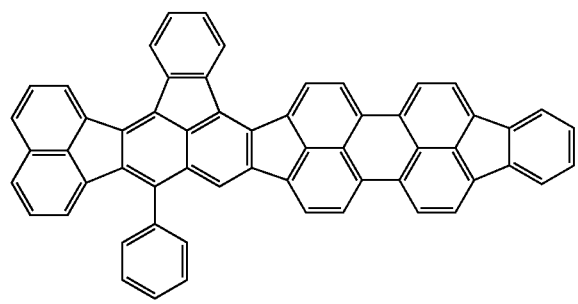

A4

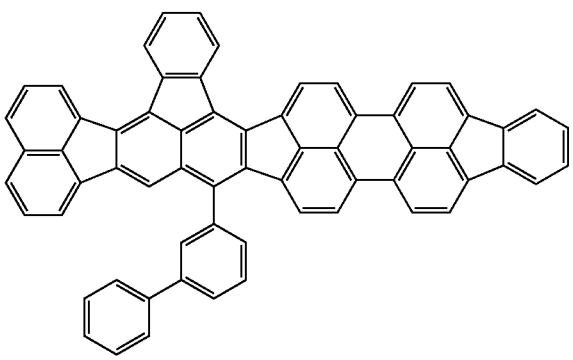

A5

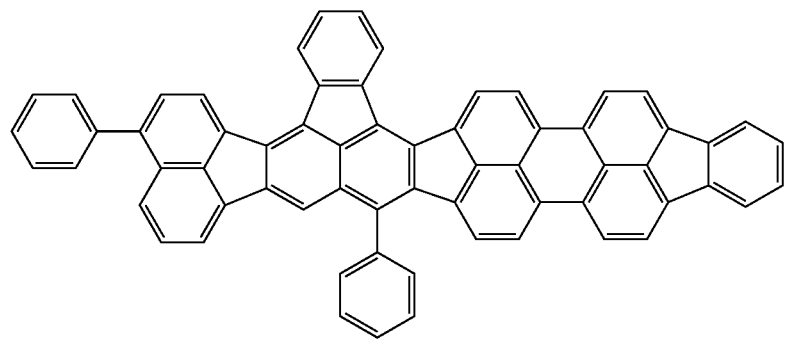

-continued
A6
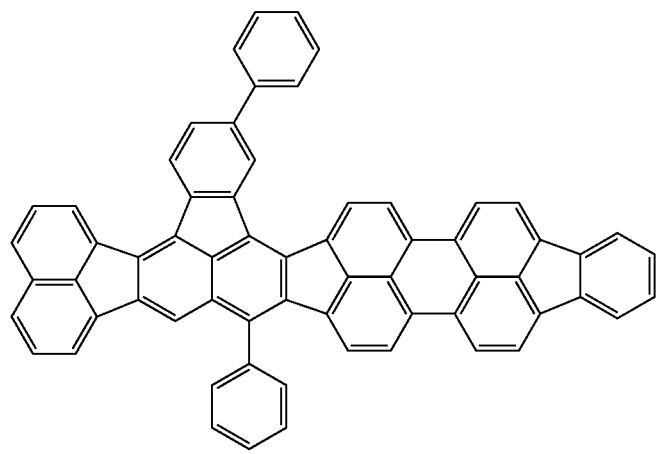
A7
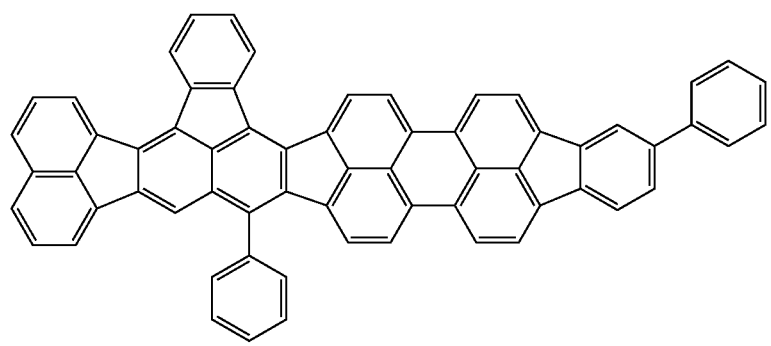
A8
A9
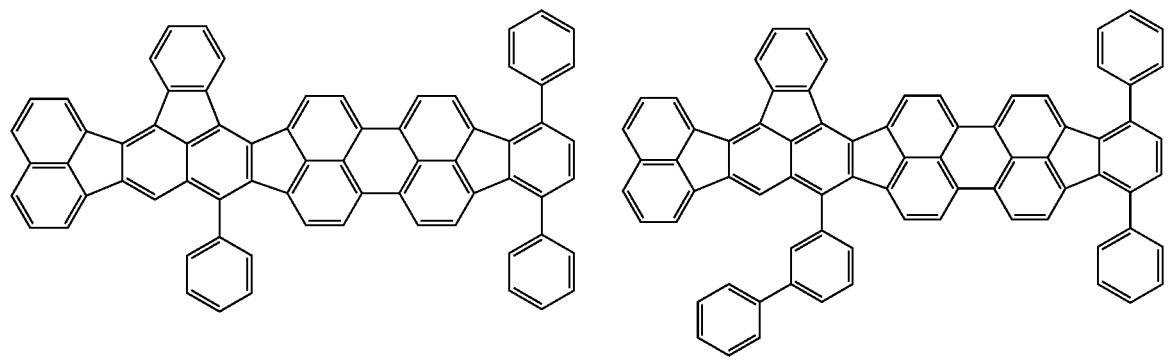
A10
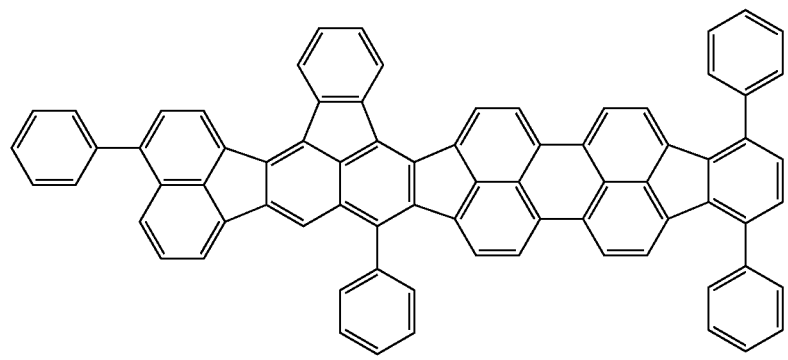

-continued
A11
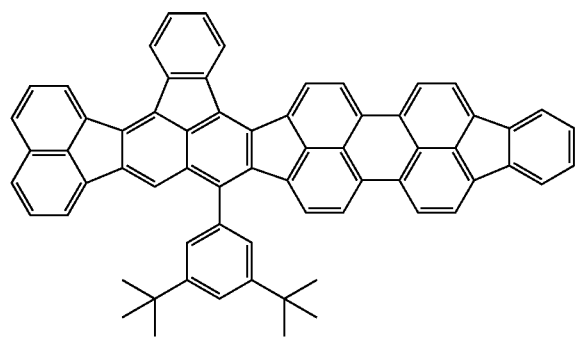
A12
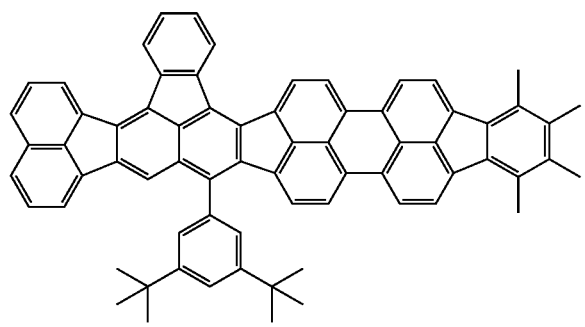
A13
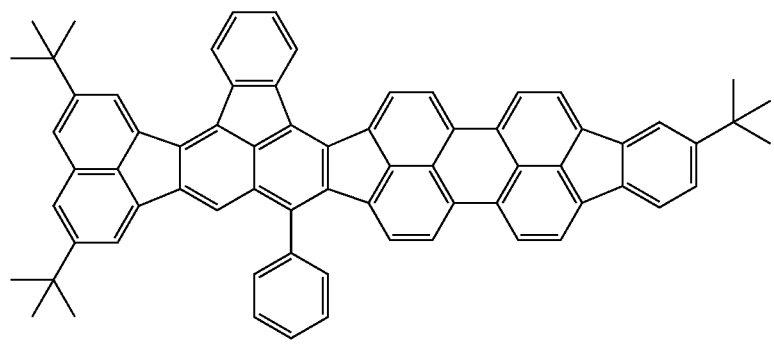
A14
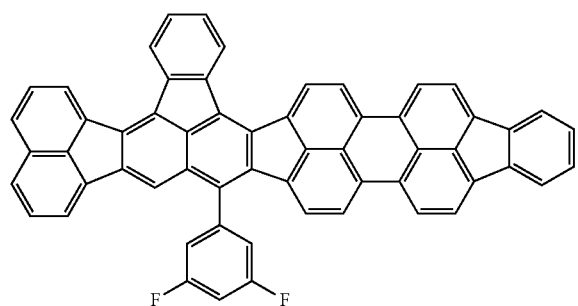
A15
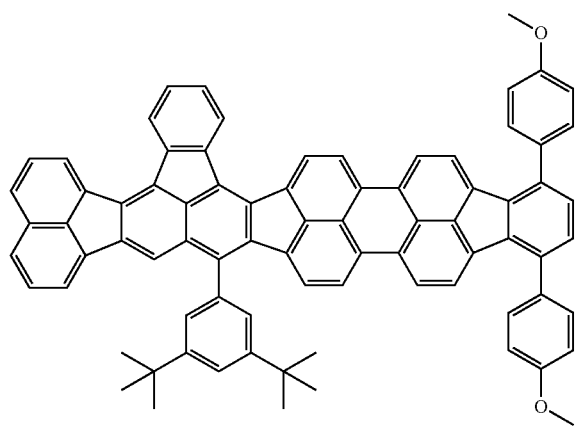
A16
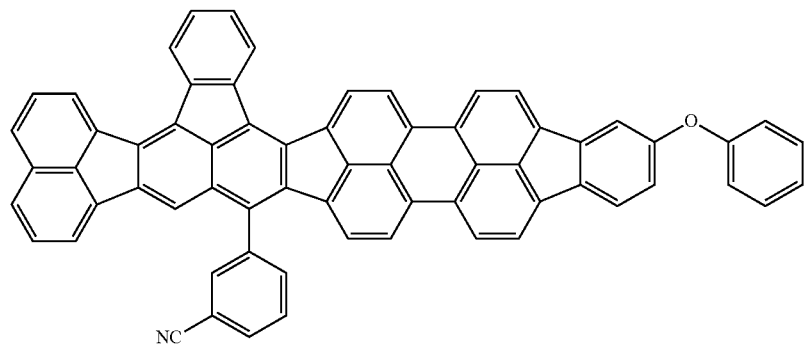

-continued
A17
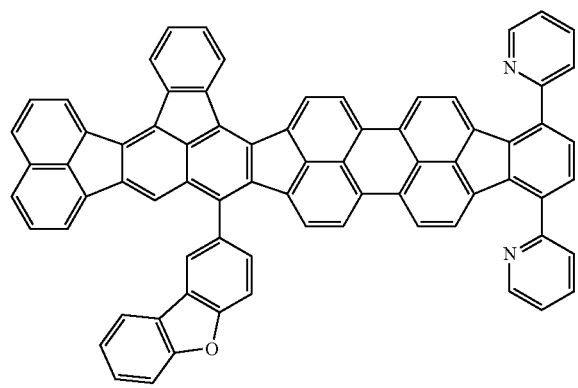
A18
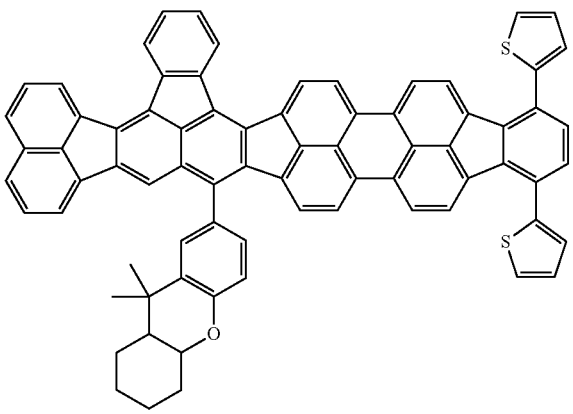
B1
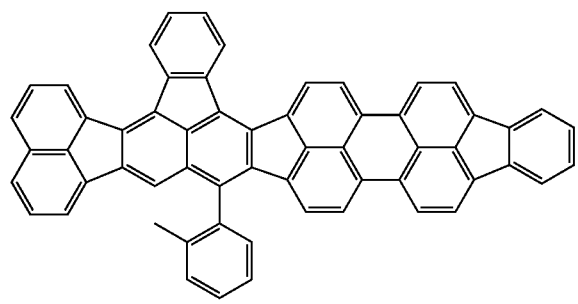
B2
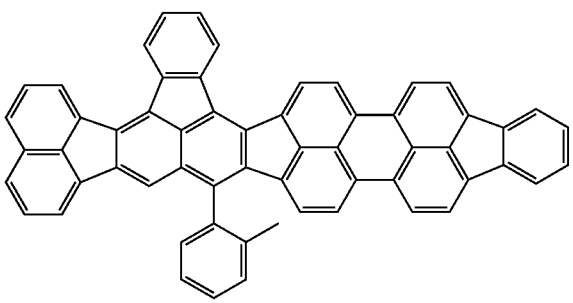
B3
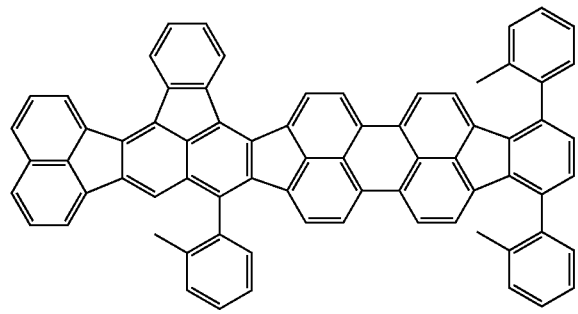
B4
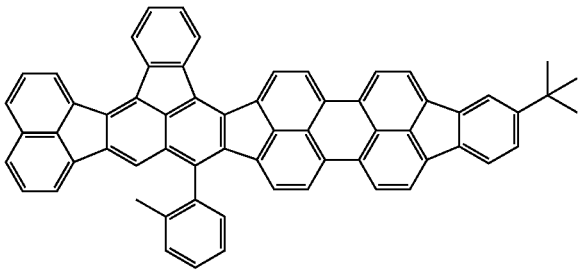
B5
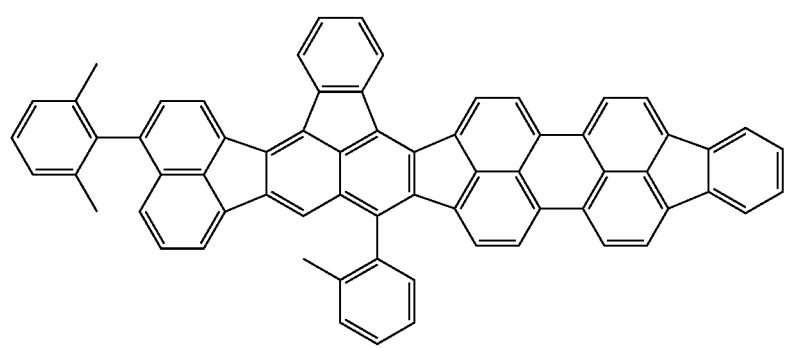

-continued
B6
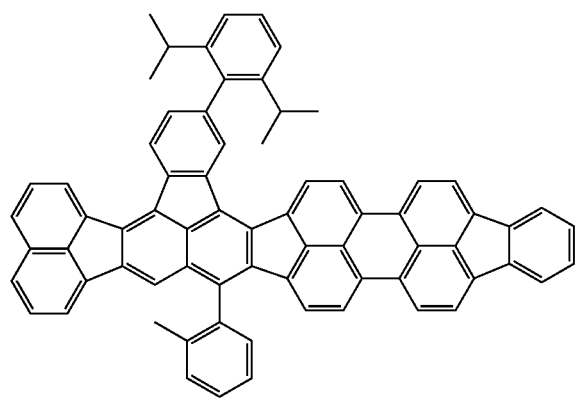
B7
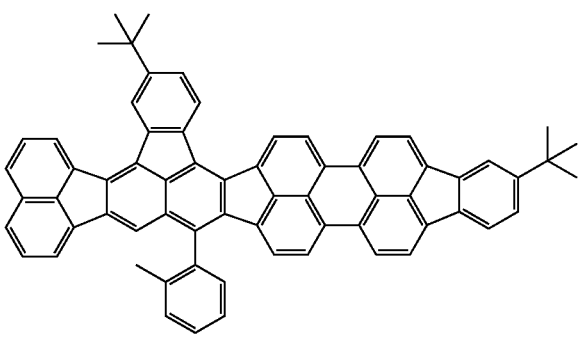
B8
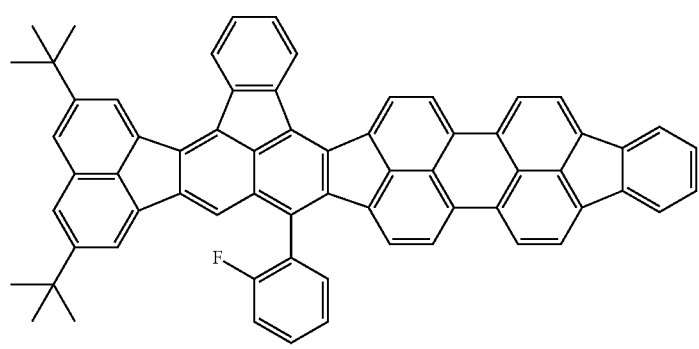
B9
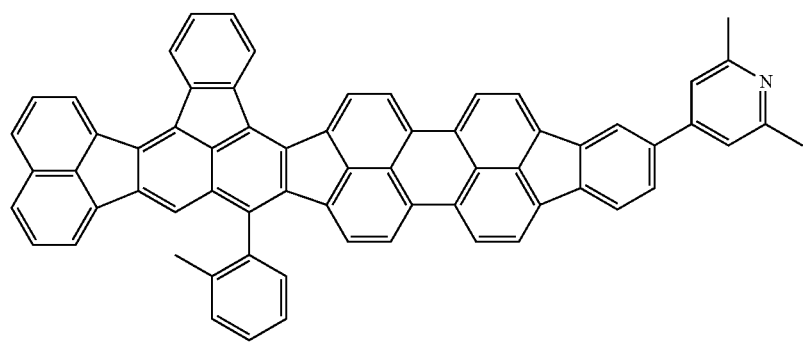
B10
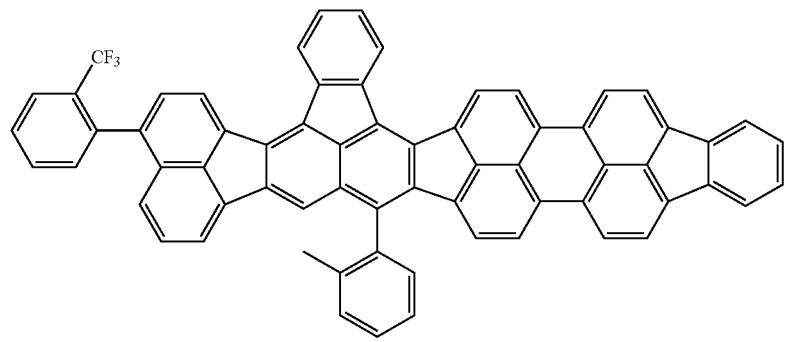

-continued
B11
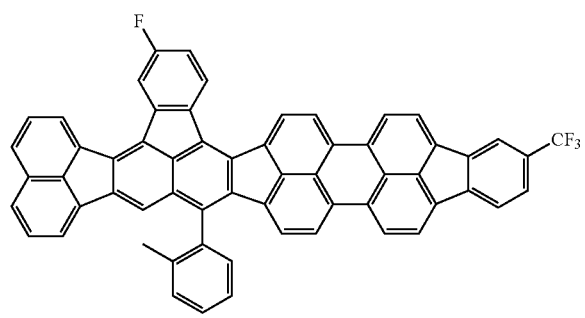
B12
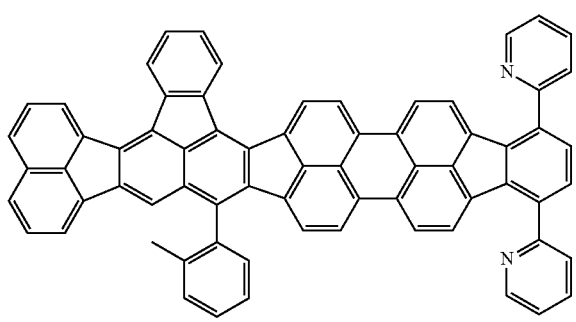
B13
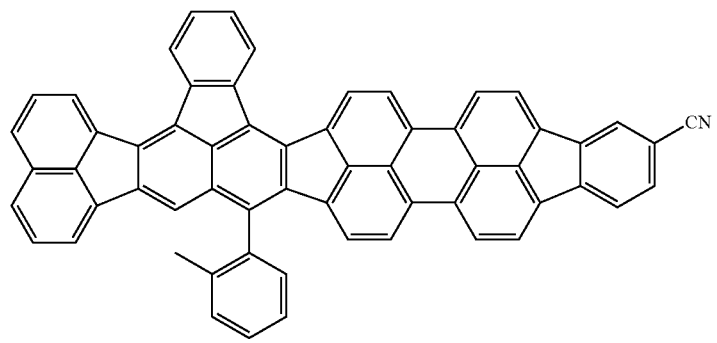
B14
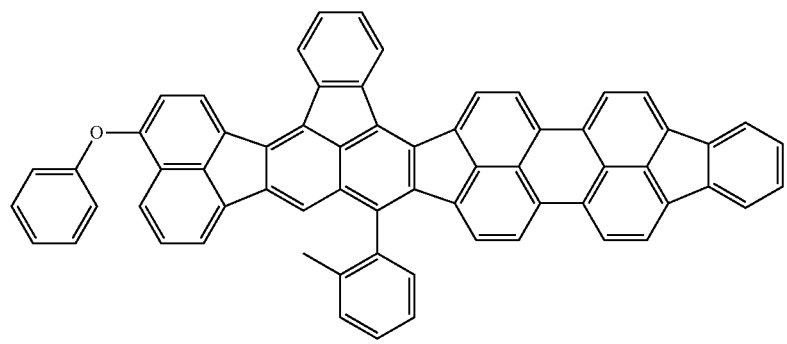
B15
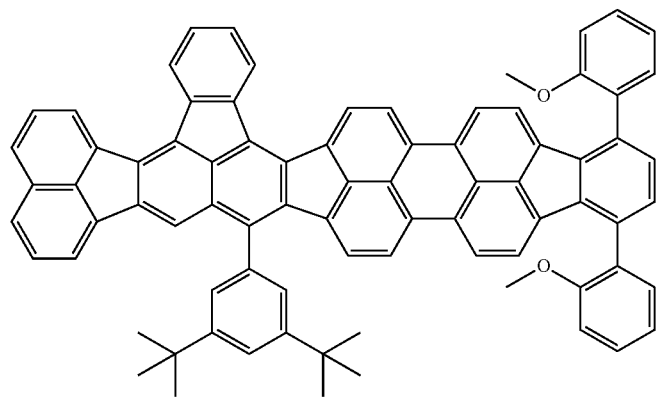

B16
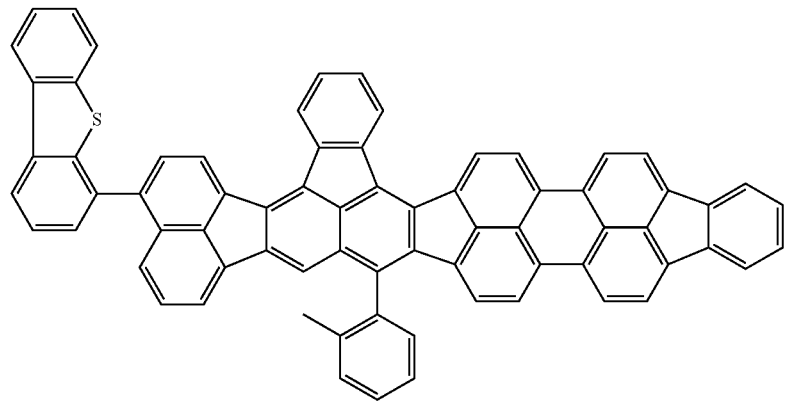
B17
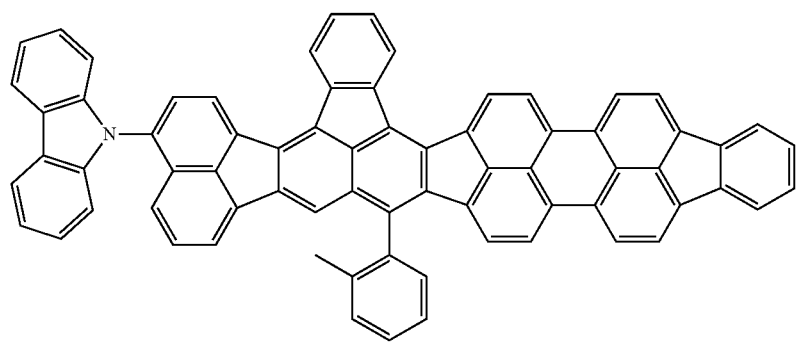
B18 C1
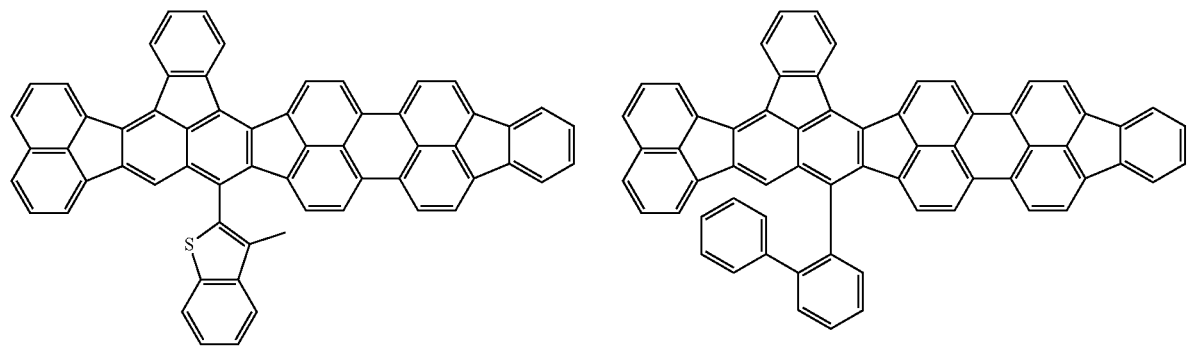
C2
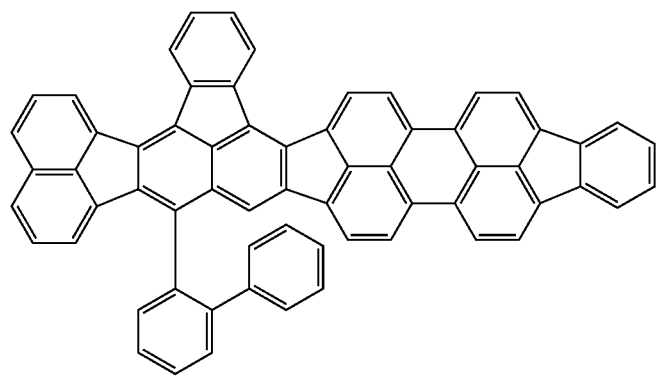

C3
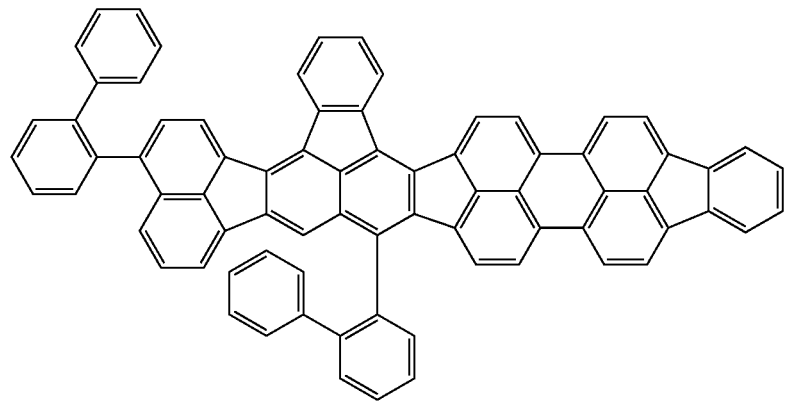
C4
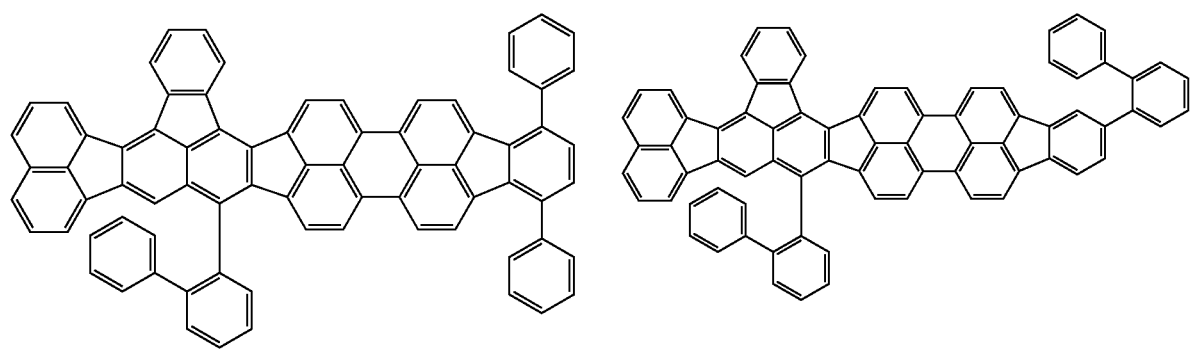
C5
C6
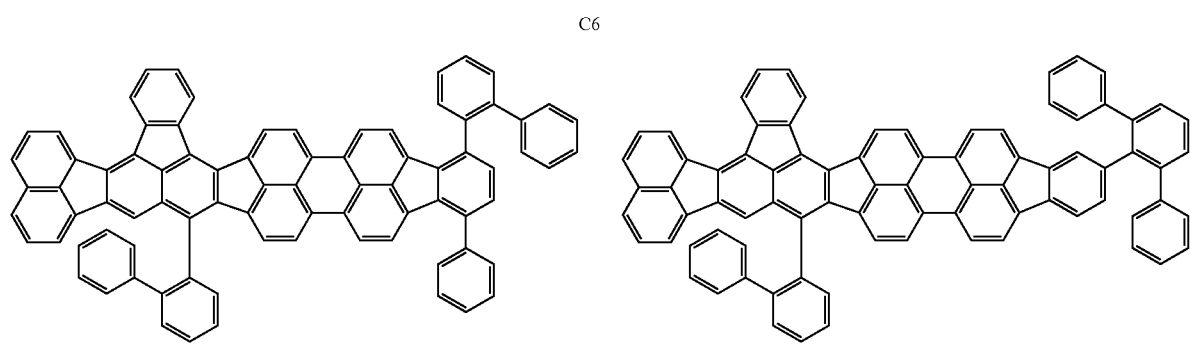
C7
C8
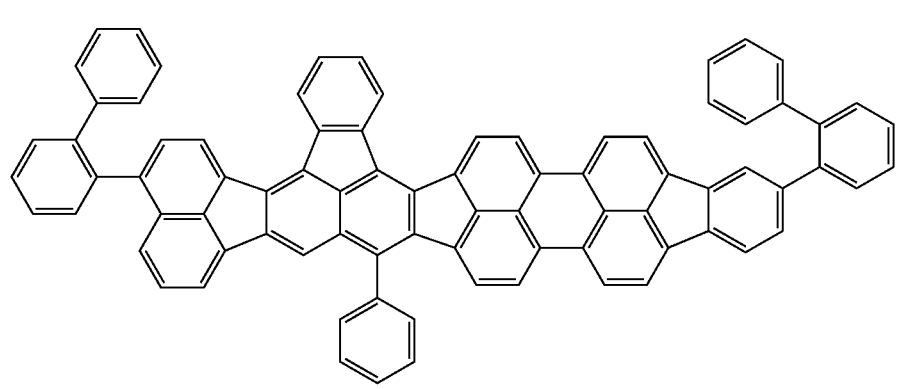

-continued
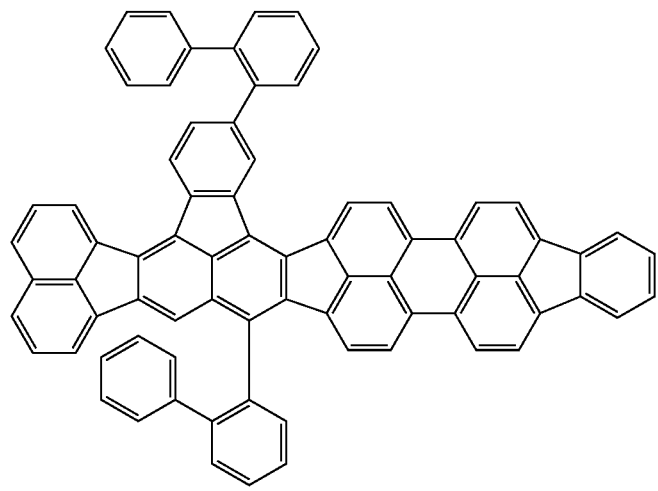
C9
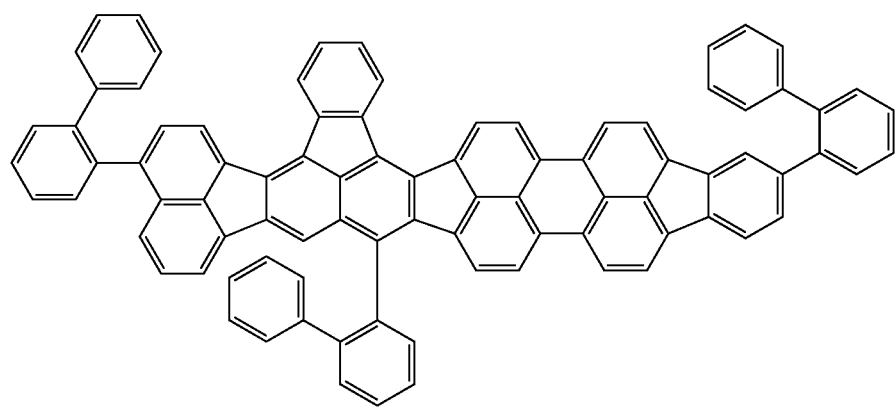
C10
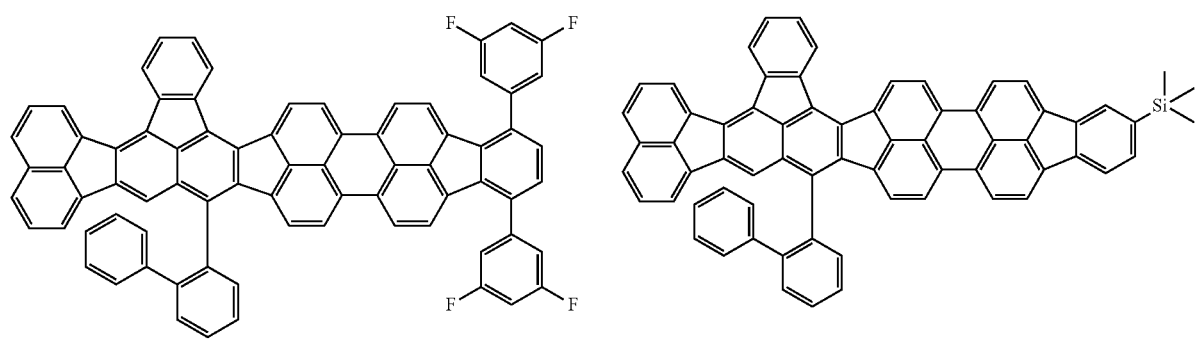
C11    C12

-continued

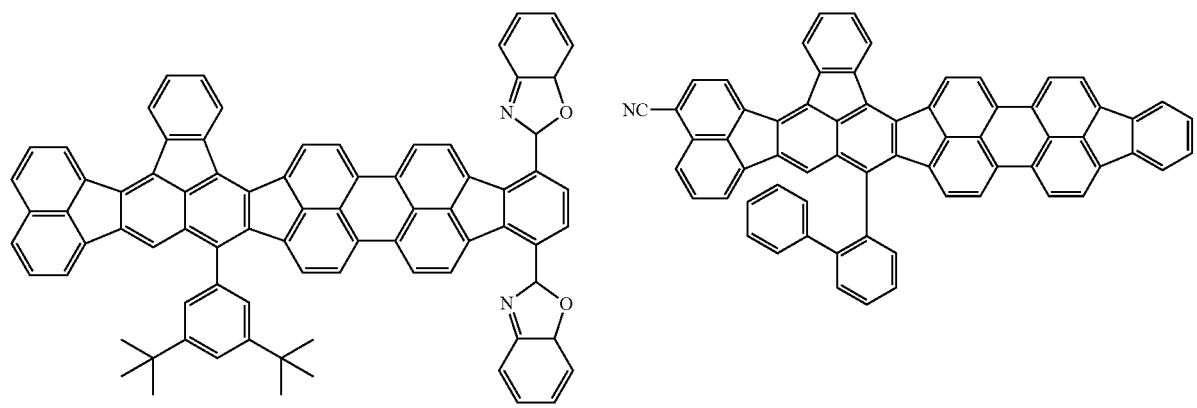

C13

C14

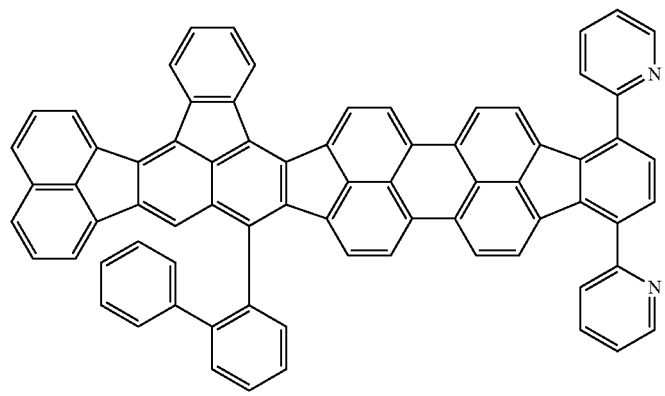

C15

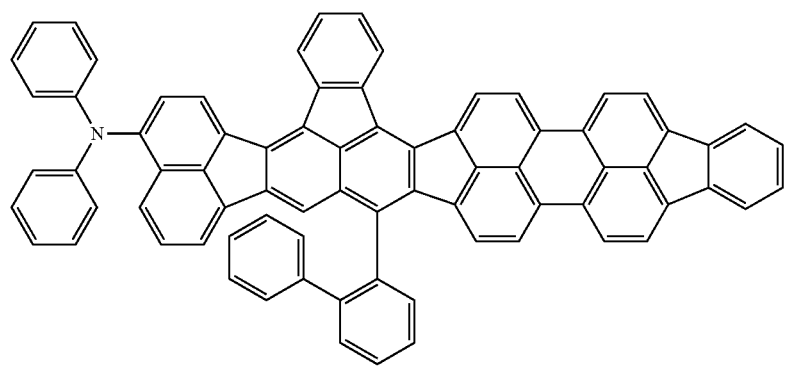

C16

Among the above exemplary compounds, the exemplary compounds A1 to A10 and C1 to C10 are compounds having only an aryl group or a hydrogen atom as $R_1$ to $R_{24}$ or a substituent included in $R_1$ to $R_{24}$. Herein, the compounds having only an aryl group or a hydrogen atom as $R_1$ to $R_{24}$ or a substituent included in $R_1$ to $R_{24}$ generally have a low HOMO energy level. Therefore, the exemplary compounds A1 to A10 and C1 to C10 are compounds having a high oxidation potential, that is, compounds having high oxidation resistance. Accordingly, among the compounds according to this embodiment, the organic compounds having only an aryl group or a hydrogen atom as $R_1$ to $R_{24}$ or a substituent included in $R_1$ to $R_{24}$, that is, the exemplary compounds A1 to A10 and C1 to C10 may be used because of their high molecular stability. The exemplary compounds A1 to A10 and C1 to C10 can also be used for, in short, light-emitting-layer host materials, transport layers, and injection layers.

Among the above exemplary compounds, the exemplary compounds A11 to A18, B1 to B18, and C11 to C16 are compounds in which an alkyl group, fluorine, an alkoxy group, an amino group, a heterocyclic group having 3 or more carbon atoms, a nitrogen-containing heterocyclic group, an aryloxy group, a silyl group, or a cyano group is introduced as $R_1$ to $R_{24}$ or a substituent included in $R_1$ to $R_{24}$. In the compounds to which an alkyl group or fluorine has been introduced, the intermolecular stacking is avoided and the sublimation temperature or the deposition start temperature is decreased. When such a compound is used as a light-emitting-layer guest material, the concentration quenching can be suppressed. Such a compound can be used as a coating material because of its high solubility. The compounds to which an alkoxy group, an aryloxy group, or a silyl group has been introduced also have an effect of suppressing the concentration quenching and thus can be used as a coating material. The compounds to which a nitrogen-containing heterocyclic group or a cyano group has been introduced have an effect of attracting electrons on the basic skeleton and thus have a low HOMO energy level and a higher oxidation resistance among the compounds according to an embodiment of the present disclosure. The compounds to which an amino group has been introduced have an effect of donating electrons on the basic skeleton and thus have a narrow band gap and emit light having a longer wavelength. The compounds to which a heterocyclic group having 3 or more carbon atoms has been introduced have a higher glass transition temperature than the compounds to which a phenyl group has been introduced. When such a compound is used for light-emitting-layer host materials or transport layers, a thermally stable amorphous film is formed.

Among the above exemplary compounds, the exemplary compounds that belong to the B group are compounds which have a phenyl group or a heterocyclic group as $R_1$ to $R_{24}$ and in which an alkyl group, fluorine, or an alkoxy group has been introduced at an ortho position of the phenyl group or the heterocyclic group. When a substituent is introduced at an ortho position of the phenyl group or the heterocyclic group, the phenyl group or the heterocyclic group is twisted with respect to the basic skeleton and the substituent at the ortho position covers the π-conjugated planes of the basic skeleton, which suppresses the molecular packing. Therefore, the intermolecular stacking is further avoided in the compounds that belong to the B group compared with the compounds that belong to the A group, which decreases the sublimation temperature or the deposition start temperature. When such a compound is used for light-emitting-layer guest materials, the concentration quenching can be suppressed.

Among the above exemplary compounds, the exemplary compounds that belong to the C group other than the exemplary compound C13 are compounds which have a phenyl group as $R_1$ to $R_{24}$ and in which a phenyl group has been further introduced at an ortho position of the phenyl group. The compounds that belong to the C group other than the exemplary compound C13 have a larger effect of covering the π-conjugated planes of the basic skeleton than the compounds that belong to the B group, and the molecular packing is further suppressed. Consequently, the intermolecular stacking is further avoided compared with the compounds that belong to the B group, which decreases the sublimation temperature or the deposition start temperature.

The organic compound according to an embodiment of the present disclosure is a compound that emits light suitable for red-light emission. Therefore, when the organic compound according to an embodiment of the present disclosure is used as a material for organic light-emitting elements, an organic light-emitting element having good light-emitting properties and high durability can be provided.

Organic Light-Emitting Element

Next, an organic light-emitting element according to this embodiment will be described. The organic light-emitting element according to this embodiment at least includes an anode and a cathode, which are a pair of electrodes, and an organic compound layer disposed between the electrodes. In the organic light-emitting element according to this embodiment, the organic compound layer may have a single-layer structure or a multilayer structure including a plurality of layers as long as the organic compound layer includes a light-emitting layer. When the organic compound layer has a multilayer structure including a plurality of layers, the organic compound layer may include, in addition to the light-emitting layer, a hole injection layer, a hole transport layer, an electron blocking layer, a hole/exciton blocking layer, an electron transport layer, and an electron injection layer. The light-emitting layer may have a single-layer structure or a multilayer structure including a plurality of layers.

In the organic light-emitting element according to this embodiment, at least one layer of the organic compound layer contains the organic compound according to this embodiment. Specifically, the organic compound according to this embodiment is contained in any of the light-emitting layer, the hole injection layer, the hole transport layer, the electron blocking layer, the hole/exciton blocking layer, the electron transport layer, and the electron injection layer. The organic compound according to this embodiment may be contained in the light-emitting layer.

In the organic light-emitting element according to this embodiment, when the organic compound according to this embodiment is contained in the light-emitting layer, the light-emitting layer may be a layer formed of only the organic compound according to this embodiment or may be a layer formed of the organic compound according to this embodiment and other compounds. When the light-emitting layer is a layer formed of the organic compound according to this embodiment and other compounds, the organic compound according to this embodiment may be used as a host of the light-emitting layer or a guest of the light-emitting layer. Alternatively, the organic compound may be used as an assist material that can be contained in the light-emitting layer. Herein, the host refers to a compound having the highest mass ratio among the compounds that form the light-emitting layer. The guest refers to a compound that has a lower mass ratio than the host and that is responsible for main light emission among the compounds that form the light-emitting layer. The assist material refers to a compound that has a lower mass ratio than the host and that assists light emission of the guest among the compounds that form the light-emitting layer. The assist material is also referred to as a second host.

When the organic compound according to this embodiment is used as a guest of the light-emitting layer, the concentration of the guest is preferably 0.01 mass % or more and 20 mass % or less and more preferably 0.1 mass % or more and 5 mass % or less relative to the whole light-emitting layer.

When the organic compound according to this embodiment is used as a guest of the light-emitting layer, a material having a higher LUMO energy level than the organic compound according to this embodiment (a material having a LUMO energy level closer to the vacuum level) may be used as the host. This is because the organic compound according to this embodiment has a low LUMO energy level, and thus when a material having a higher LUMO energy level than the organic compound according to this embodiment is used as the host, the organic compound according to this embodiment can receive a larger amount of electrons supplied to the host of the light-emitting layer.

As a result of thorough studies, the present inventors have found that when the organic compound according to this embodiment is used as the host or guest of the light-emitting layer, in particular, as the guest of the light-emitting layer, an element that produces an optical output with high efficiently and high luminance and that has very high durability is provided. This light-emitting layer may have a single-layer structure or a multilayer structure, or red light, which is an emission color of this embodiment, can be mixed with another color light by adding a light-emitting material having another emission color. The multilayer structure refers to a state in which the light-emitting layer and another light-emitting layer are stacked. In this case, the emission color of the organic light-emitting element is not limited to red. The emission color may be specifically white or an intermediate color. In the case of white, the other light-emitting layer emits light having a color other than red, such as blue or green. The light-emitting layers are formed by a method such as vapor deposition or coating. The details of the method will be specifically described in Examples below.

The organic compound according to this embodiment can be used as a material for organic compound layers other than the light-emitting layer constituting the organic light-emitting element according to this embodiment. Specifically, the organic compound may be used as a material for electron transport layers, electron injection layers, hole transport layers, hole injection layers, and hole blocking layers. In this case, the emission color of the organic light-emitting element is not limited to red. The emission color may be specifically white or an intermediate color.

The organic compound according to this embodiment may be used in combination with, for example, a publicly known low-molecular-weight or high-molecular-weight hole injection compound or hole transport compound, a compound serving as the host, a luminous compound, an electron injection compound, and an electron transport compound if necessary. Examples of these compounds will be described below.

A hole injection or transport material may be a material having a high hole mobility such that injection of holes from the anode is facilitated and the injected holes can be transported to the light-emitting layer. The hole injection or transport material may also be a material having a high glass transition temperature in order to suppress the deterioration of the film quality, such as crystallization in the organic light-emitting element. Examples of the low-molecular-weight or high-molecular-weight material having hole injectability or transportability include triarylamine derivatives, arylcarbazole derivatives, phenylenediamine derivatives, stilbene derivatives, phthalocyanine derivatives, porphyrin derivatives, poly(vinylcarbazole), poly(thiophene), and other electrically conductive polymers. The above hole injection or transport material is also suitably used for the electron blocking layer. Non-limiting specific examples of the compound used as the hole injection or transport material are shown below.

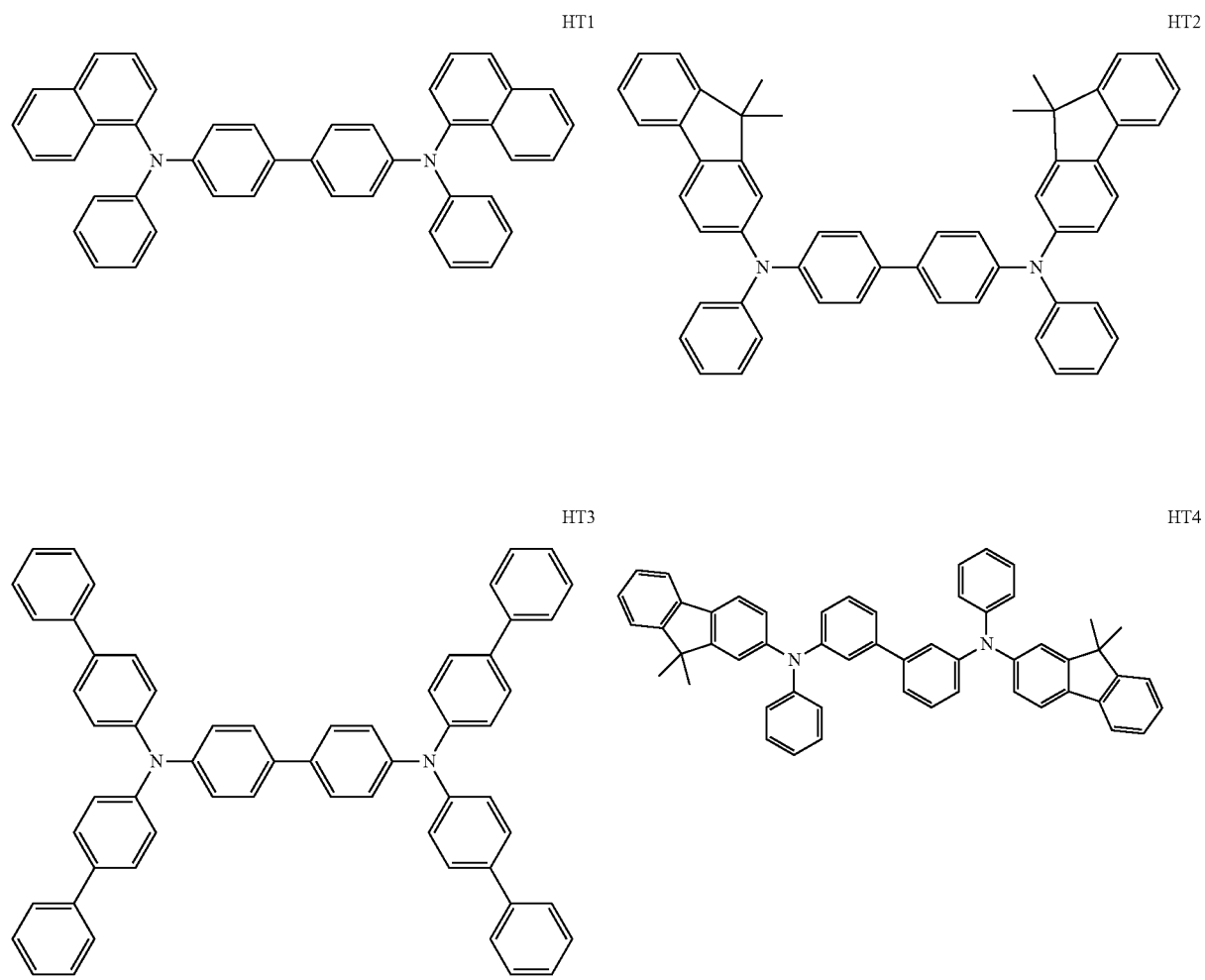

-continued
HT5
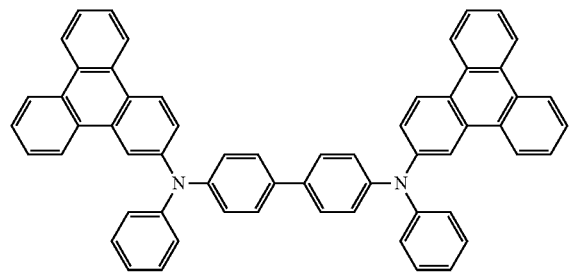
HT6
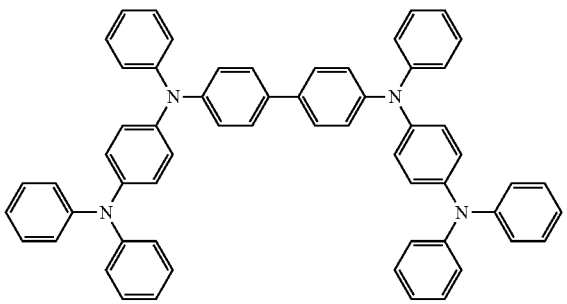
HT7
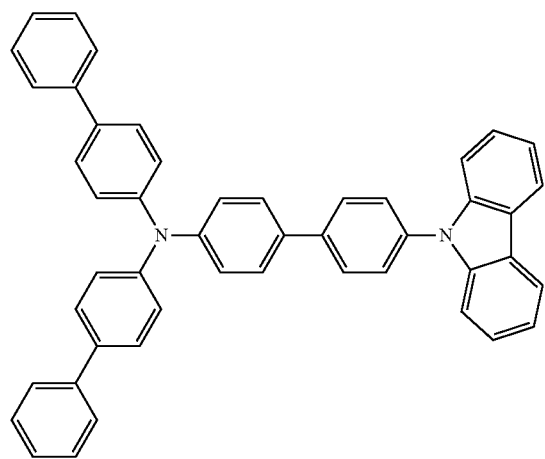
HT8
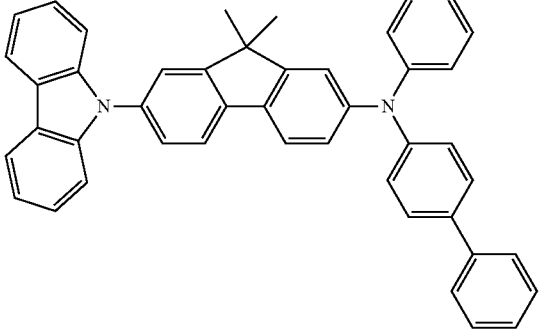
HT9
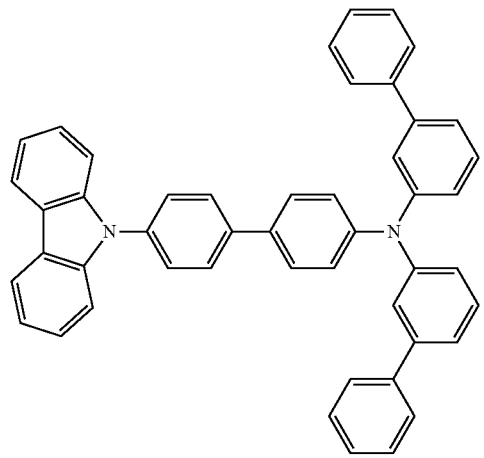
HT10
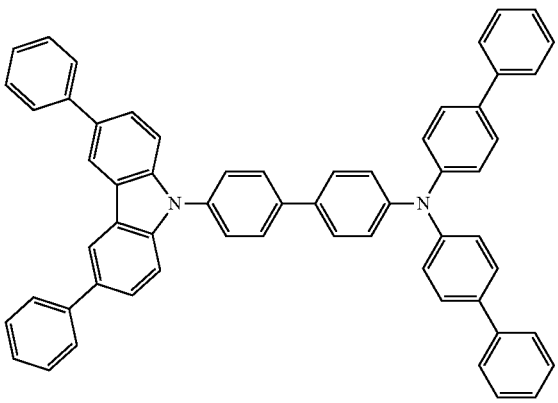
HT11
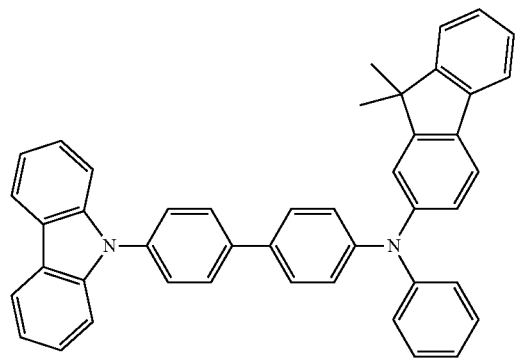
HT12
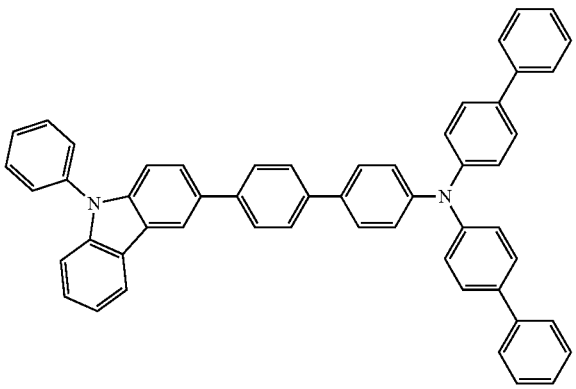

-continued
HT13
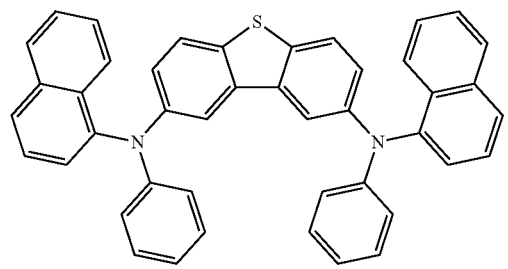
HT14
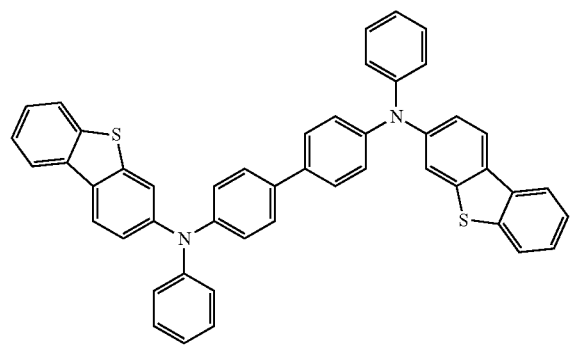
HT15
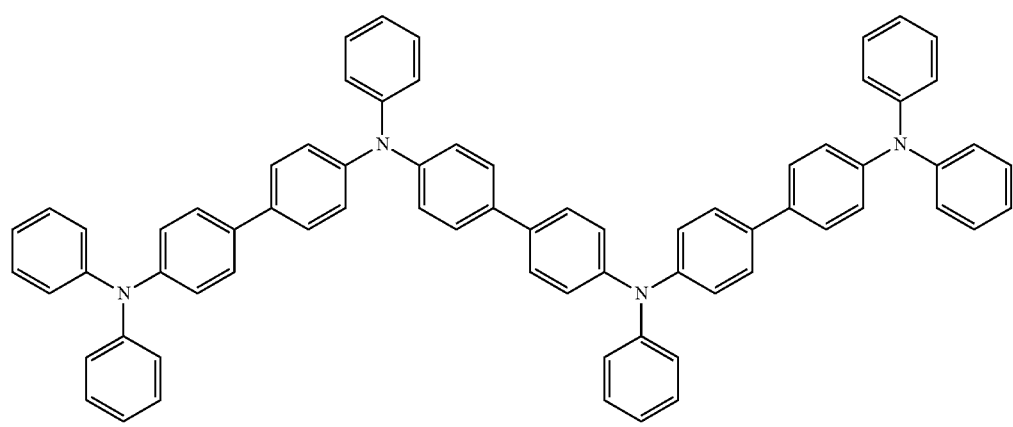
HT16
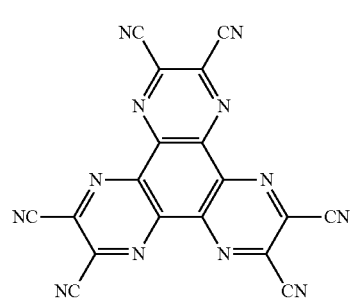
HT17
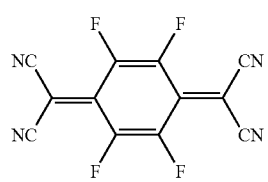
HT18
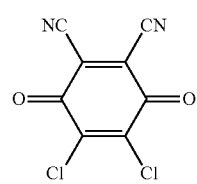
HT19
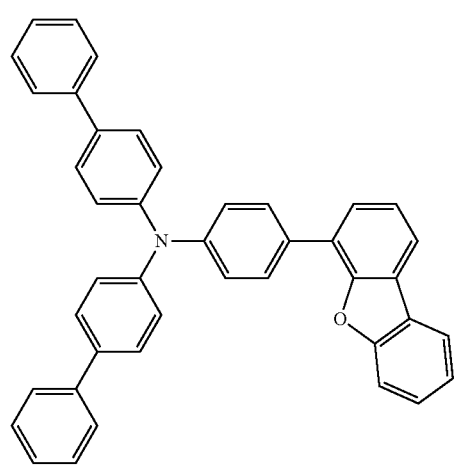

Examples of the light-emitting material mainly concerned with a light-emitting function include, in addition to the organic compound represented by the formula (1), fused ring compounds (e.g., fluorene derivatives, naphthalene derivatives, pyrene derivatives, perylene derivatives, tetracene derivatives, anthracene derivatives, and rubrene), quinacridone derivatives, coumarin derivatives, stilbene derivatives, organoaluminum complexes such as tris(8-quinolinolato) aluminum, iridium complexes, platinum complexes, rhenium complexes, copper complexes, europium complexes, ruthenium complexes, and polymer derivatives such as poly(phenylene vinylene) derivatives, poly(fluorene) derivatives, and poly(phenylene) derivatives.

The organic compound according to an embodiment of the present disclosure is a compound having a narrow band gap and a low HOMO/LUMO energy level. Therefore, when a mixture layer is formed with another light-emitting material or when light-emitting layers are stacked, the other light-emitting material may also have a low HOMO/LUMO energy level. This is because if the HOMO/LUMO energy level is high, formation of a quenching component or a trap level may occur, such as the case where the other light-emitting material forms an exciplex with the organic compound according to an embodiment of the present disclosure.

Non-limiting specific examples of the compound used as the light-emitting material are shown below.

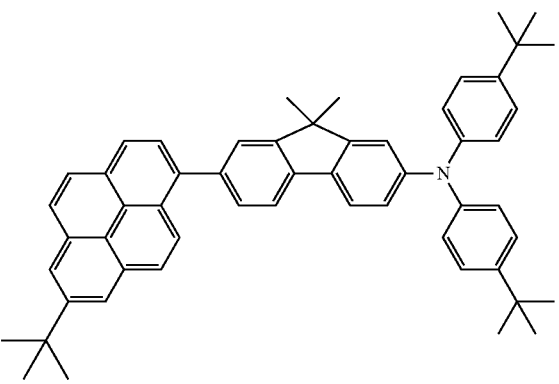

BD3

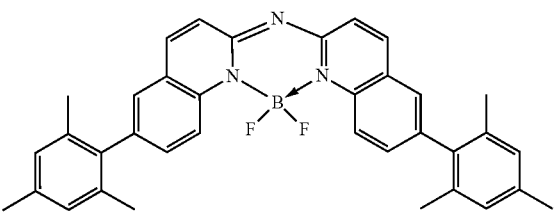

BD4

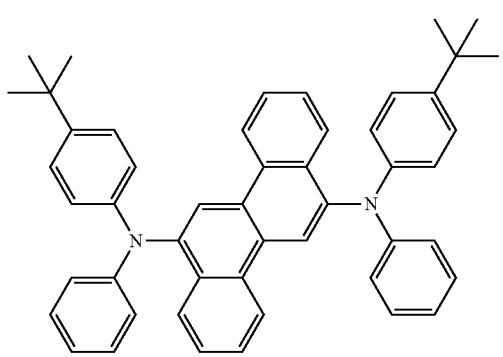

BD1

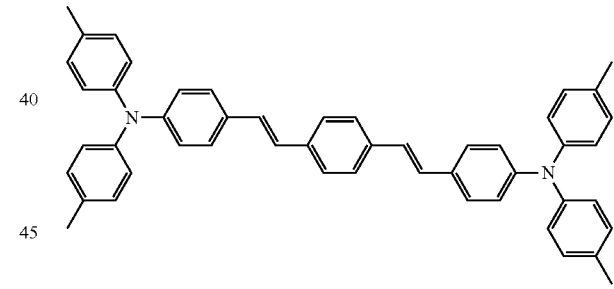

BD5

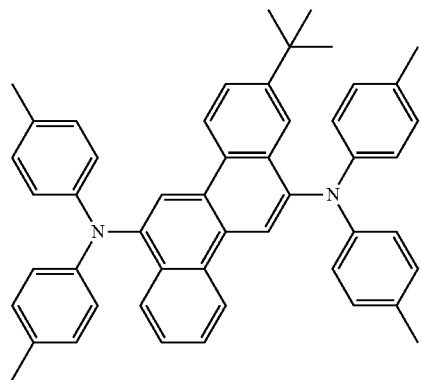

BD2

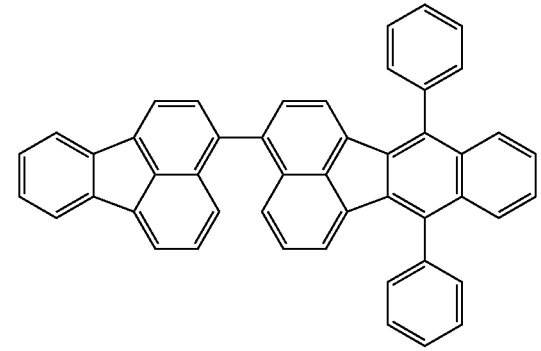

BD6

BD7
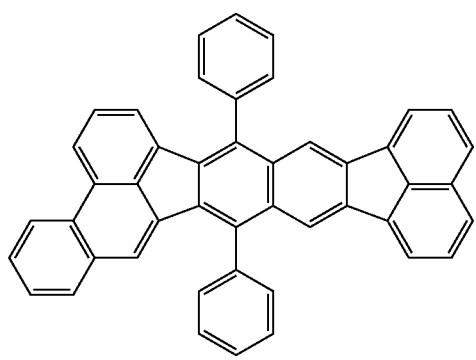
BD8
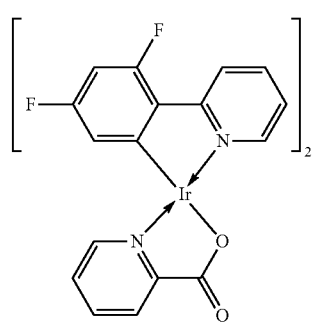
GD1
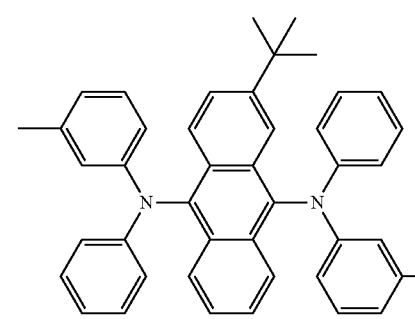
GD2
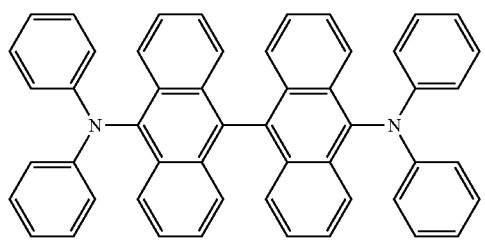
GD3
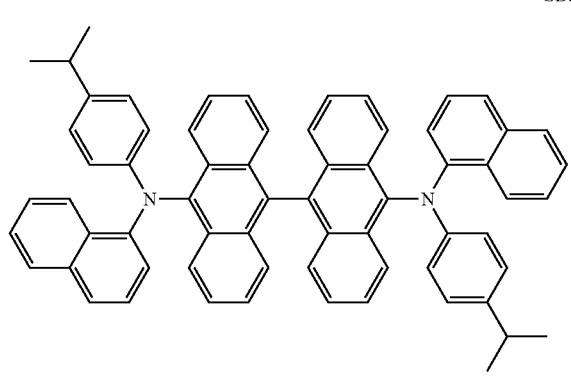
GD4
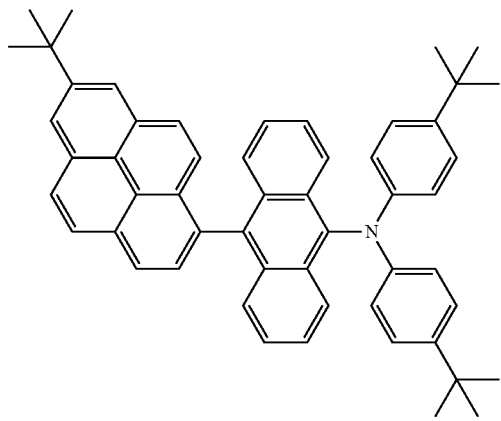
GD5
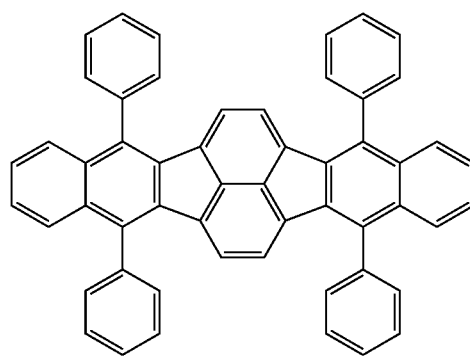
GD6
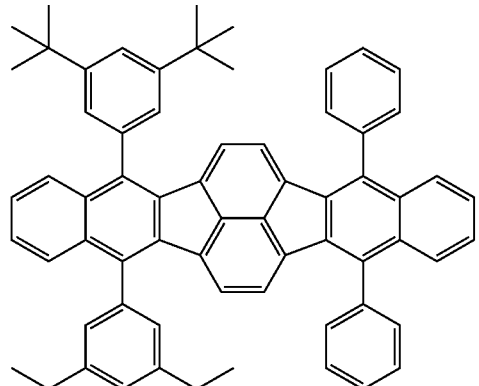
GD7
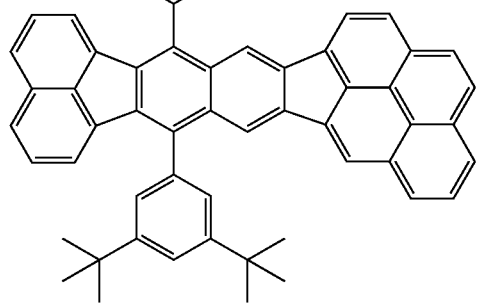

GD8

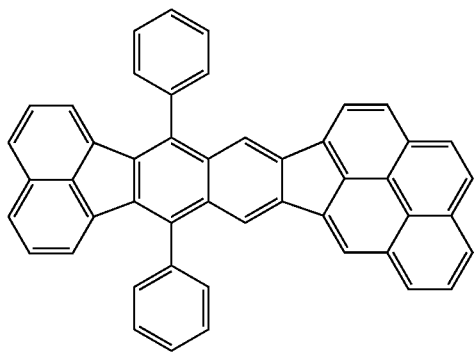

GD9

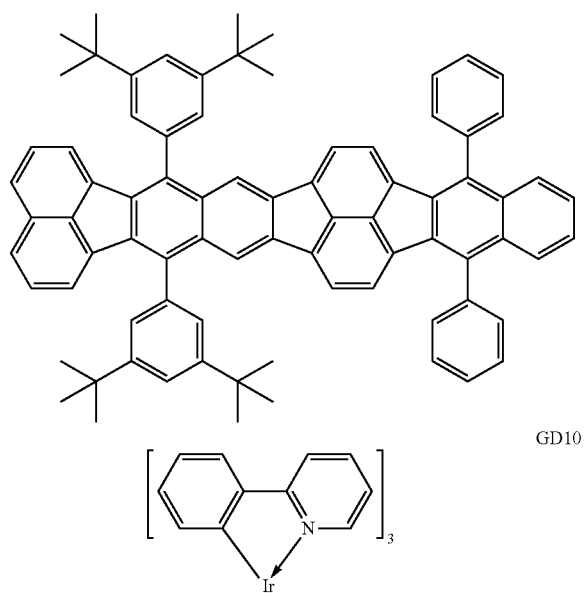

GD10

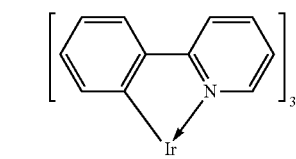

GD11

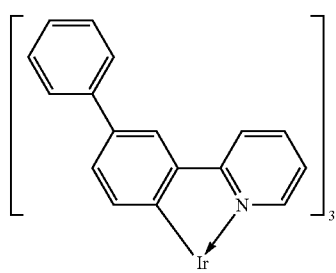

GD12

Examples of the light-emitting-layer host or light emission assist material contained in the light-emitting layer include aromatic hydrocarbon compounds and derivatives thereof, carbazole derivatives, dibenzofuran derivatives, dibenzothiophene derivatives, organoaluminum complexes such as tris(8-quinolinolato)aluminum, and organoberyllium complexes.

The organic compound according to an embodiment of the present disclosure is a compound having a narrow band gap and a low HOMO/LUMO energy level. Therefore, the host material may also be formed of a hydrocarbon and may have a low HOMO/LUMO energy level. This is because if the host material contains a hetero atom such as a nitrogen atom, the HOMO/LUMO energy level increases, and formation of a quenching component or a trap level may occur, such as the case where the host material forms an exciplex with the organic compound according to an embodiment of the present disclosure.

In particular, the host material may have an anthracene, tetracene, perylene, or pyrene skeleton in its molecular skeleton. This is because the host material is formed of a hydrocarbon as described above and also has an Si energy capable of causing sufficient energy transfer to the organic compound according to an embodiment of the present disclosure.

Non-limiting specific examples of the compound used as the light-emitting-layer host or light emission assist material contained in the light-emitting layer are shown below.

EM1

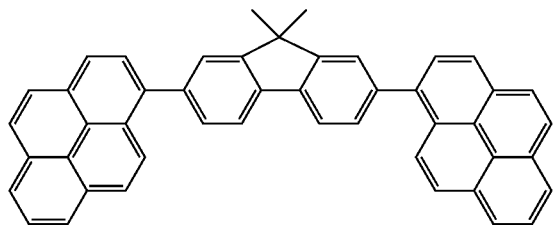

EM2

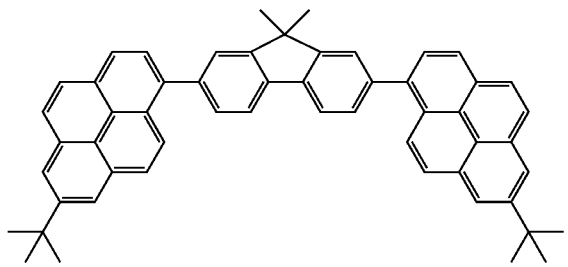

-continued
EM3
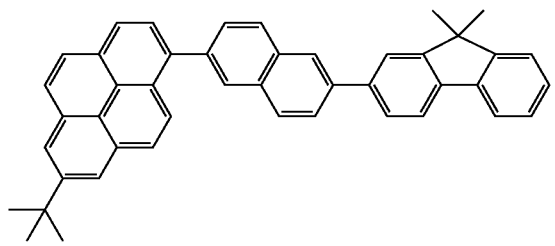
EM4
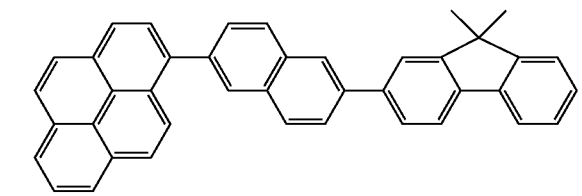
EM5
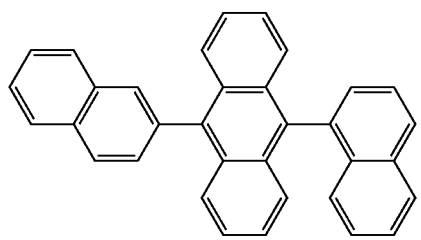
EM6
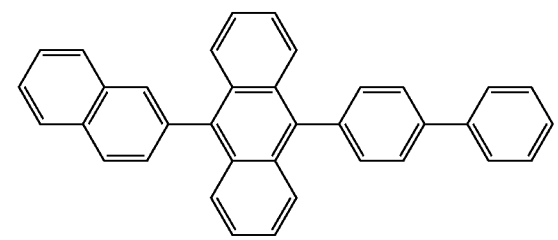
EM7
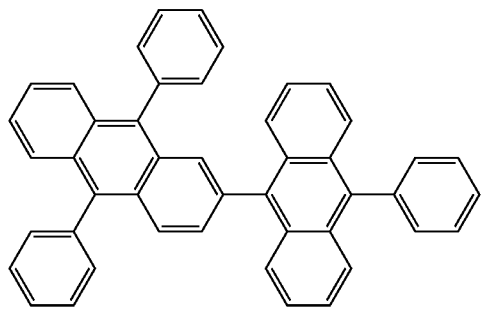
EM8
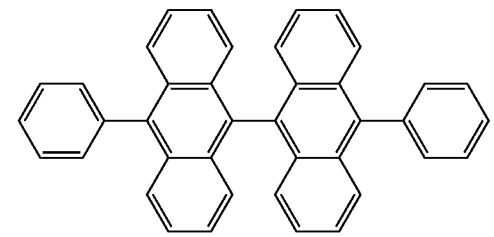
EM9
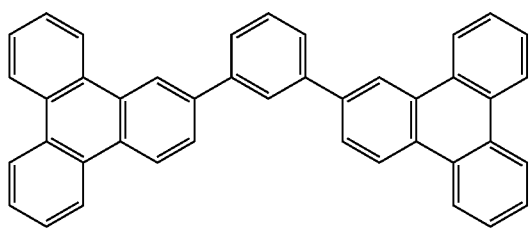
EM10
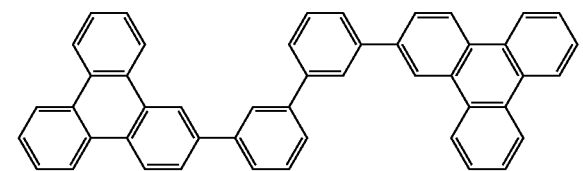
EM11
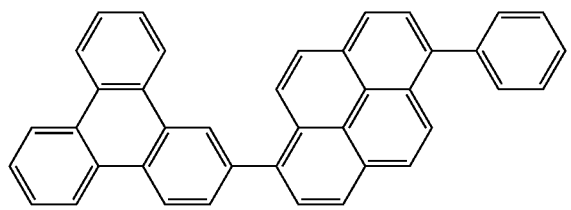
EM12
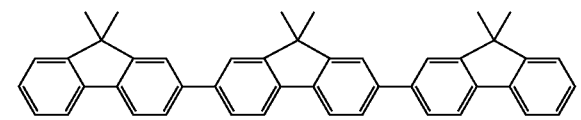
EM13
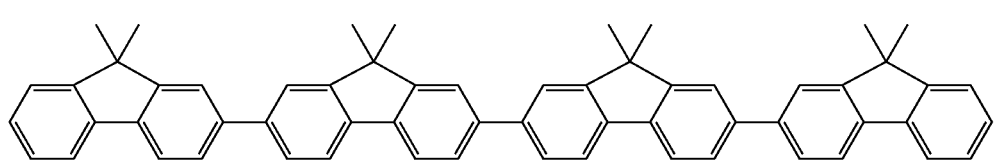

-continued
EM14
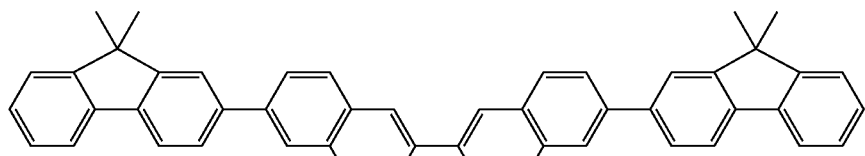
EM15
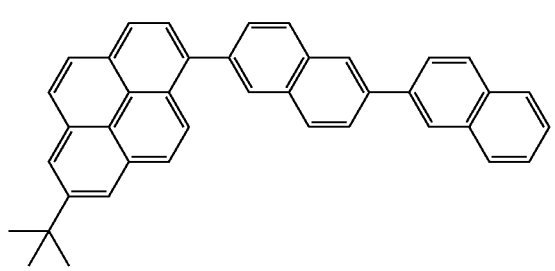
EM16
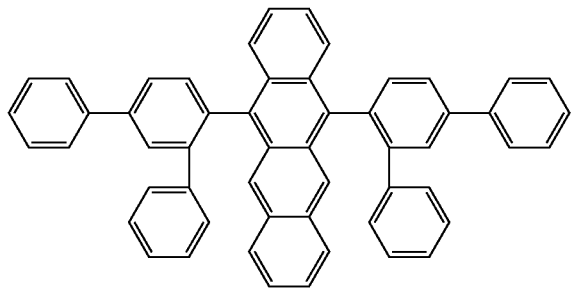
EM17
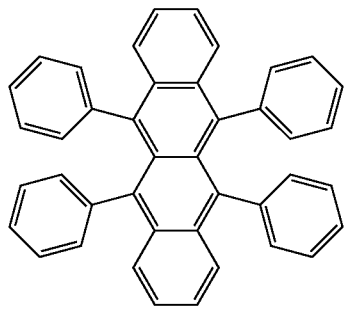
EM18
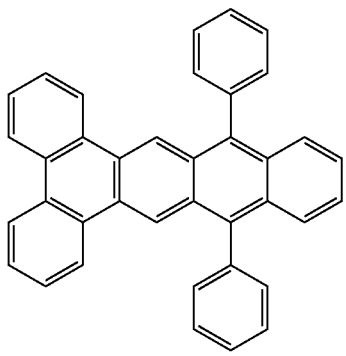
EM19
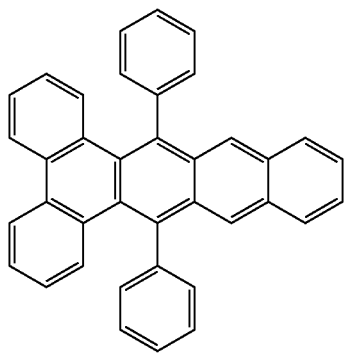
EM20
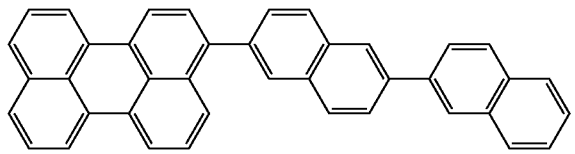
EM21
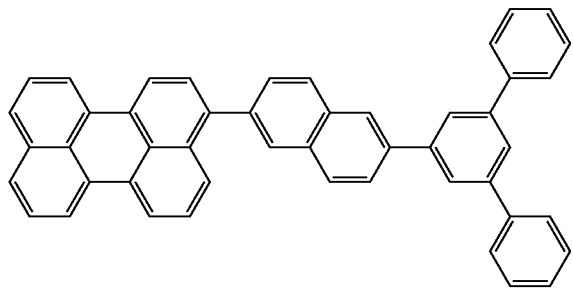
EM22
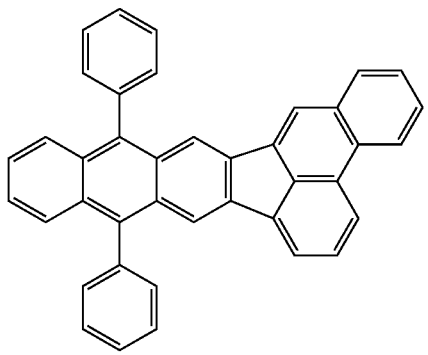

EM23
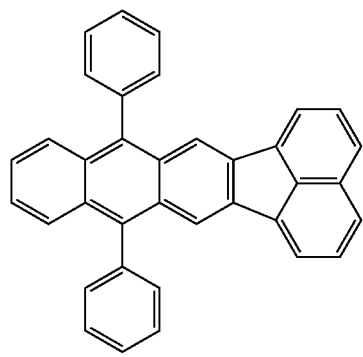
EM24
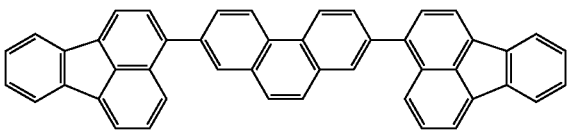
EM25
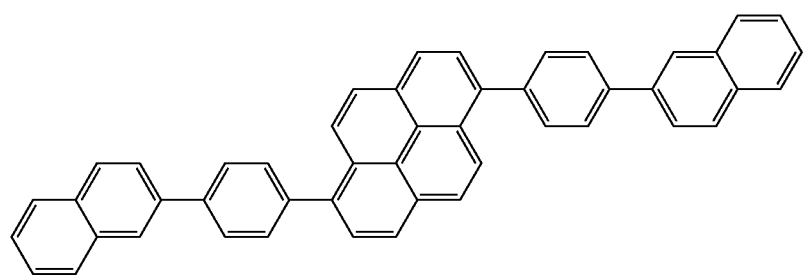
EM26
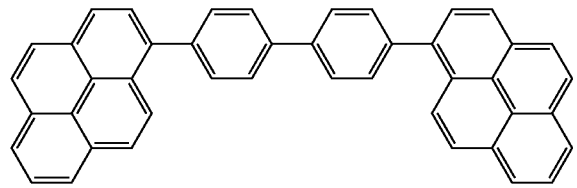
EM27
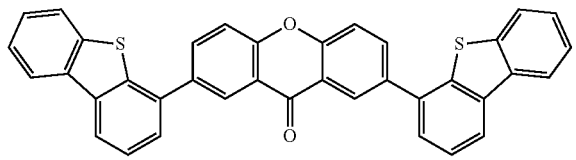
EM28
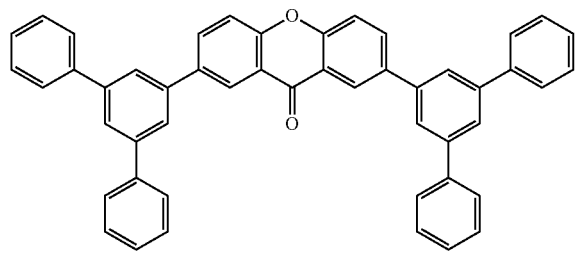
EM29
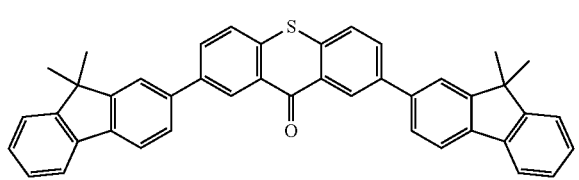
EM30
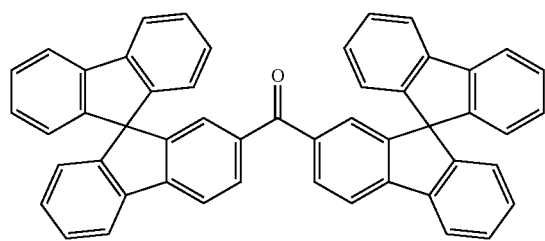
EM31
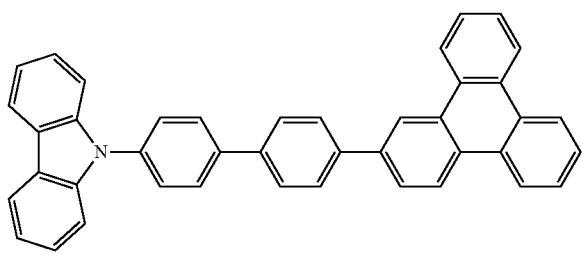

EM32
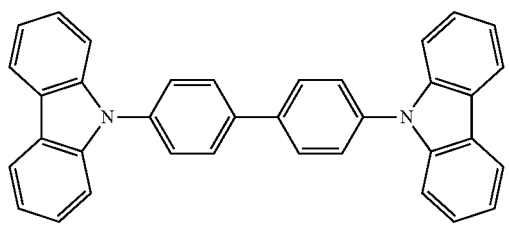

EM33
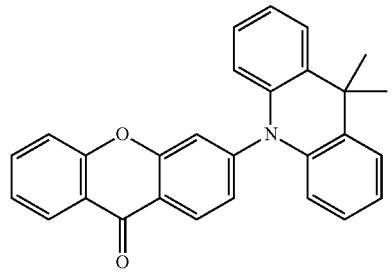

EM34
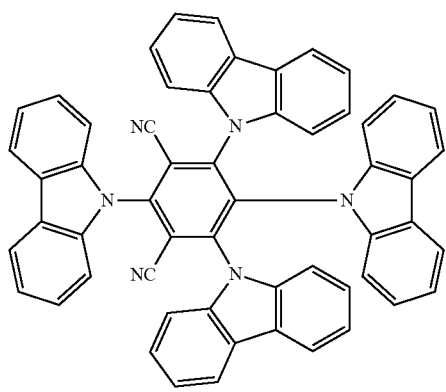

EM35
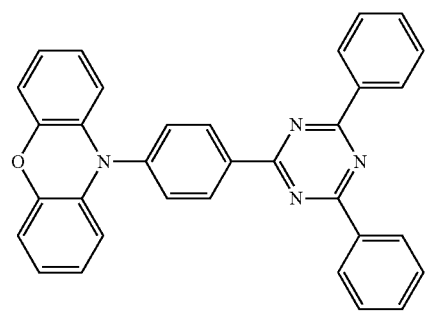

The electron transport material can be freely selected from materials capable of transporting electrons injected from the cathode to the light-emitting layer. The electron transport material is selected in consideration of, for example, the balance with the hole mobility of the hole transport material. Examples of the material having electron transportability include oxadiazole derivatives, oxazole derivatives, pyrazine derivatives, triazole derivatives, triazine derivatives, quinoline derivatives, quinoxaline derivatives, phenanthroline derivatives, organoaluminum complexes, and fused ring compounds (e.g., fluorene derivatives, naphthalene derivatives, chrysene derivatives, and anthracene derivatives). The above electron transport material is also suitably used for the hole blocking layer. Non-limiting specific examples of the compound used as the electron transport material are shown below.

ET2
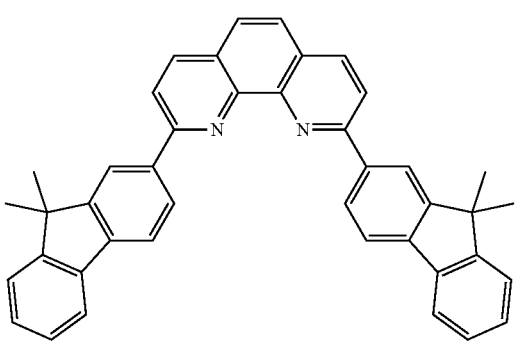

ET1
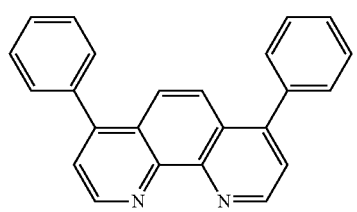

ET3
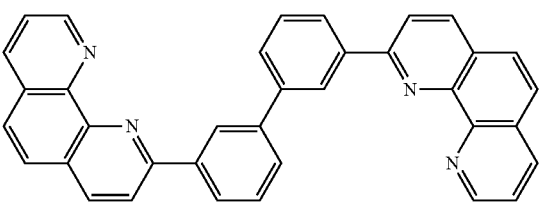

ET4
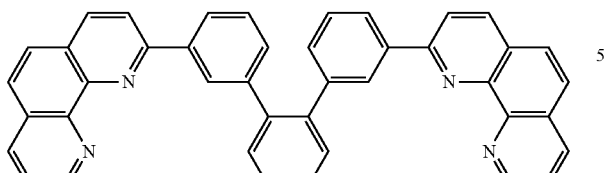
ET5
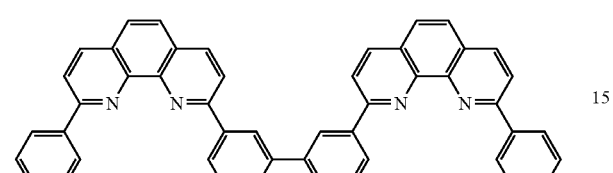
ET6
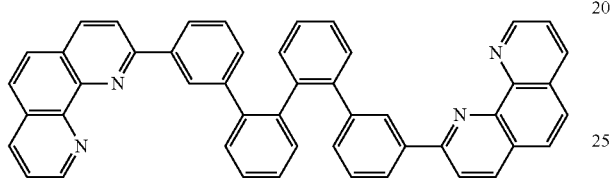
ET7
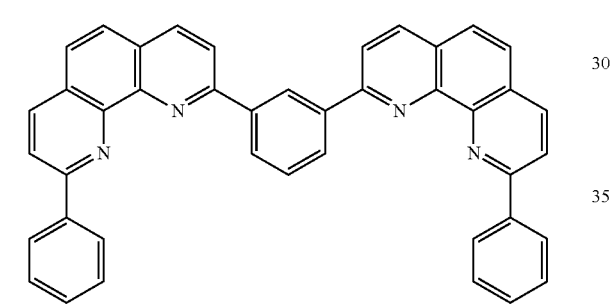
ET8
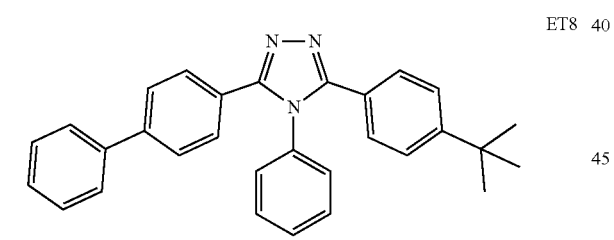
ET9
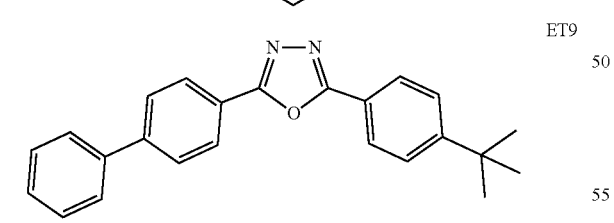
ET10
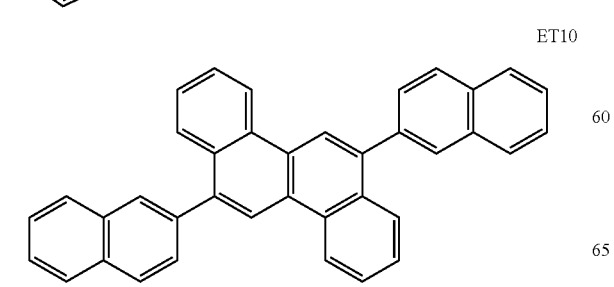
ET11
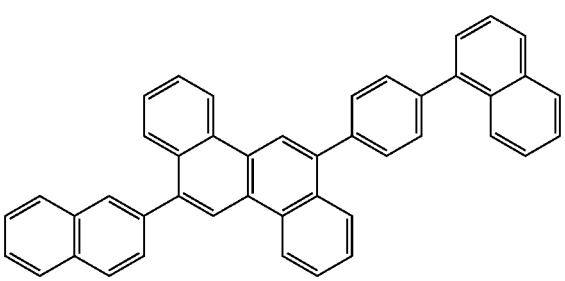
ET12
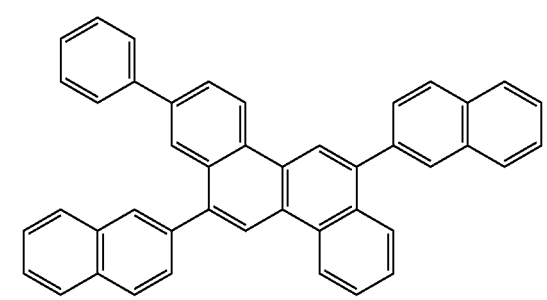
ET13
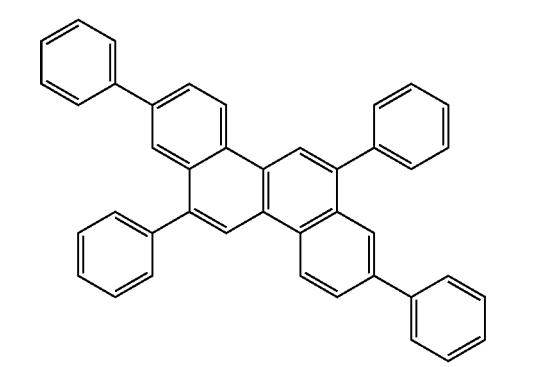
ET14
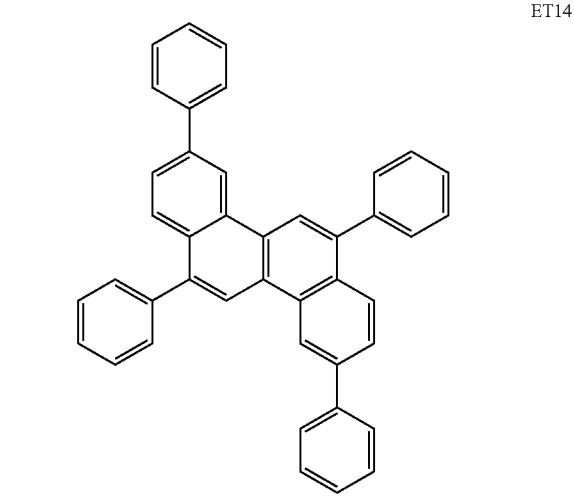

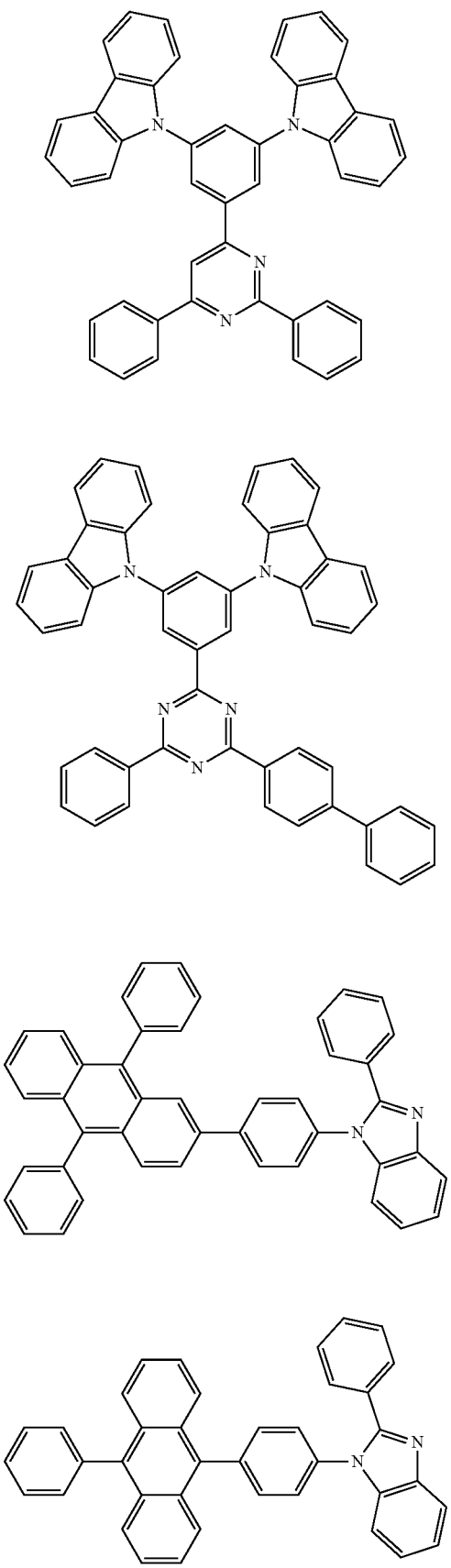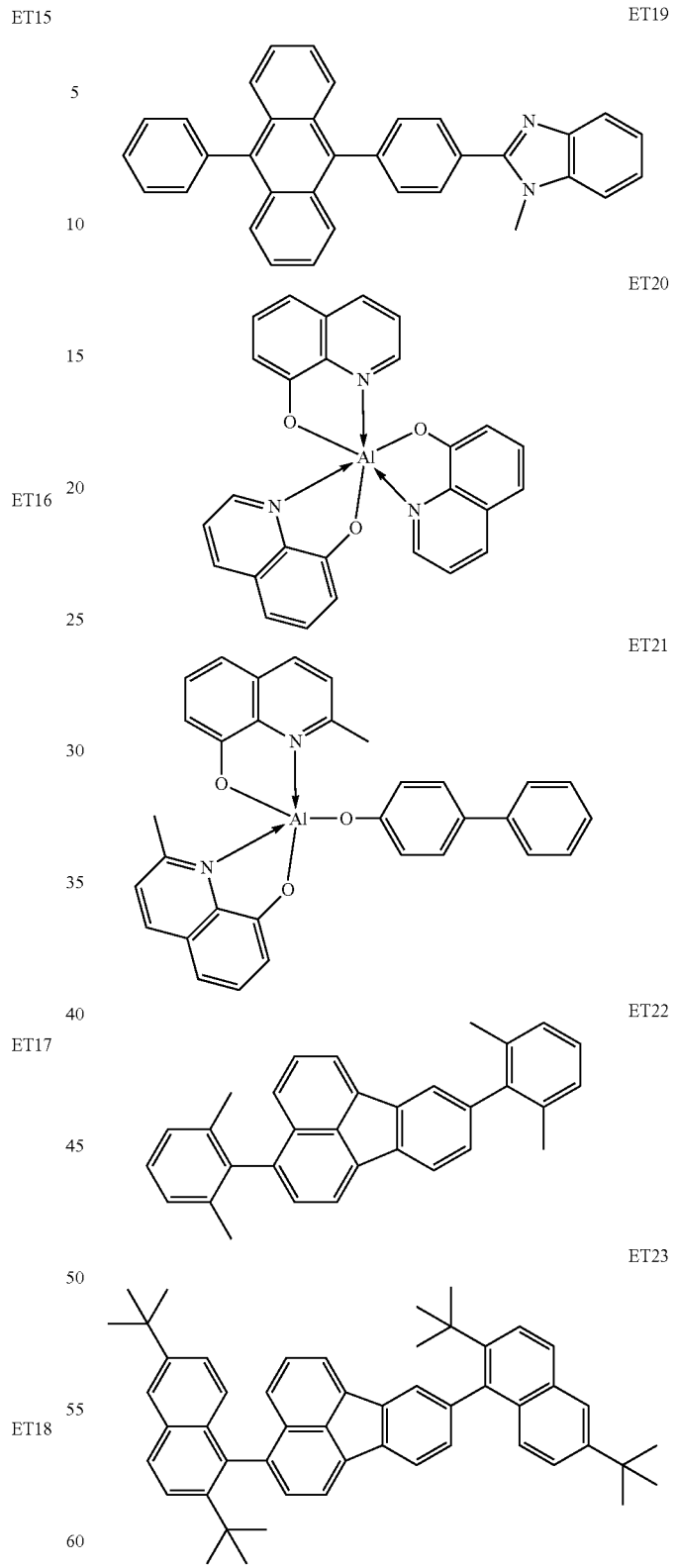
Hereafter, members other than the organic compound layer that constitute the organic light-emitting element according to this embodiment will be described. The organic light-emitting element may be provided by forming an anode, an organic compound layer, and a cathode on a substrate. For example, a protective layer and a color filter may be disposed on the cathode. If the color filter is disposed, a planarizing layer may be disposed between the protective layer and the color filter. The planarizing layer may be formed of, for example, an acrylic resin.

The substrate may be formed of any material such as quartz, glass, silicon wafer, resin, or metal. A switching element such as a transistor and a wire may be disposed on the substrate, and an insulating layer may be disposed thereon. The insulating layer may be formed of any material as long as contact holes can be formed to establish electrical connection between the anode and the wire and the anode can be insulated from wires to which the anode is not connected. Examples of the material for the insulating layer include resins such as polyimide, silicon oxide, and silicon nitride.

The material for the anode desirably has as high a work function as possible. Examples of the material for the anode include elemental metals such as gold, platinum, silver, copper, nickel, palladium, cobalt, selenium, vanadium, and tungsten; mixtures containing these metals; alloys of these metals; and metal oxides such as tin oxide, zinc oxide, indium oxide, indium tin oxide (ITO), and indium zinc oxide. Conductive polymers such as polyaniline, polypyrrole, and polythiophene can also be used. These electrode materials may be used alone or in combination of two or more. The anode may have a single-layer structure or a multilayer structure. When the anode is used as a reflective electrode, for example, chromium, aluminum, silver, titanium, tungsten, molybdenum, an alloy thereof, or a laminate thereof can be used. When the anode is used as a transparent electrode, a transparent conductive oxide layer made of, for example, indium tin oxide (ITO) or indium zinc oxide can be used, but the materials are not limited thereto. The anode can be formed by photolithography.

On the other hand, the material for the cathode desirably has a low work function. Examples of the material for the cathode include alkali metals such as lithium; alkaline earth metals such as calcium; elemental metals such as aluminum, titanium, manganese, silver, lead, and chromium; mixtures containing these metals; alloys of these metals, such as magnesium-silver, aluminum-lithium, aluminum-magnesium, silver-copper, and zinc-silver; and metal oxides such as indium tin oxide (ITO). These electrode materials may be used alone or in combination of two or more. The cathode may have a single-layer structure or a multilayer structure. In particular, silver is preferably used and a silver alloy is more preferably used to suppress aggregation of silver. The silver alloy may have any mixing ratio such as 1:1 as long as the aggregation of silver can be suppressed.

Any device may be employed, such as a top emission device obtained by using a conductive oxide layer made of, for example, ITO as a cathode or a bottom emission device obtained by using a reflective electrode made of, for example, aluminum (Al) as a cathode. The cathode may be formed by any method such as a DC and AC sputtering method. In this method, good film coverage can be achieved to readily reduce the resistance.

After formation of the cathode, a protective layer may be disposed. For example, a glass plate including a moisture absorbent is bonded to the cathode. This suppresses permeation of water or the like into the organic compound layer and thus can suppress occurrence of display defects. In another embodiment, a passivation film made of silicon nitride or the like may be disposed on the cathode to suppress permeation of water or the like into the organic compound layer. For example, after the formation of the cathode, the resulting substrate may be transferred to another chamber without breaking the vacuum, and a silicon nitride film having a thickness of 2 µm may be formed by a chemical vapor deposition (CVD) method to provide a protective layer. After the film formation by the CVD method, a protective layer may be disposed by an atomic layer deposition method (ALD method).

A color filter may be disposed on each pixel. For example, color filters each having a size corresponding to the pixel size may be disposed on another substrate, and this substrate may be bonded to the substrate on which the organic light-emitting elements have been disposed. Alternatively, a color filter may be patterned on a protective layer made of silicon oxide or the like using photolithography.

The organic compound layers (e.g., a hole injection layer, a hole transport layer, an electron blocking layer, a light-emitting layer, a hole blocking layer, an electron transport layer, and an electron injection layer) that constitute the organic light-emitting element according to this embodiment are formed by the following method. That is, the organic compound layer can be formed by a dry process such as a vacuum vapor deposition method, an ionized vapor deposition method, a sputtering method, or a method using plasma. Instead of the dry process, a wet process in which an organic compound is dissolved in an appropriate solvent and a layer is formed by a publicly known coating method (e.g., spin coating, dipping, a casting method, a Langmuir-Blodgett (LB) method, or an ink jet method) can also be employed. When a layer is formed by, for example, a vacuum vapor deposition method or a solution coating method, crystallization or the like is unlikely to occur and the resulting layer has high stability over time. When a layer is formed by a coating method, the layer can be formed by using an appropriate binder resin in combination. Non-limiting examples of the binder resin include polyvinylcarbazole resin, polycarbonate resin, polyester resin, ABS resin, acrylic resin, polyimide resin, phenolic resin, epoxy resin, silicone resin, and urea resin. The binder resins may be used alone as a homopolymer or in combination as a mixture of two or more as a copolymer. Furthermore, publicly known additives such as a plasticizer, an antioxidant, and an ultraviolet absorber may be optionally used in combination.

Apparatus Including Organic Light-Emitting Element

The organic light-emitting element according to this embodiment can be used as a member of display apparatuses and lighting apparatuses. In addition, the organic light-emitting element may be used as, for example, an exposure light source for electrophotographic image forming apparatuses, a backlight of liquid crystal display apparatuses, and a light-emitting device including a white light source having a color filter.

The display apparatus may be an image information processing apparatus that includes an image input unit which inputs image information from an area CCD, a linear CCD, a memory card, or the like and an information processing unit which processes the input information and that displays the input image on a display unit. The display unit included in an image pickup apparatus or an ink jet printer may have a touch panel function. The touch panel function may be driven by any method such as a method that uses infrared rays, electrostatic capacitance, a resistive film, or electromagnetic induction. The display apparatus may be used as a display unit of multifunction printers.

By using an apparatus including the organic light-emitting element according to this embodiment, an image having good image quality can be stably displayed for a long time.

Display Apparatus

A display apparatus according to this embodiment includes a plurality of pixels, at least one of which includes the organic light-emitting element according to this embodiment. The pixels include the organic light-emitting element according to this embodiment and an active element. The display apparatus may be used as a display unit of an image display apparatus including an input section for inputting image information and a display section for outputting an image.

FIG. 2 is a schematic sectional view illustrating an example of a display apparatus according to this embodiment that includes organic light-emitting elements and TFT elements connected to the organic light-emitting elements. The TFT elements are an example of active elements. The display apparatus according to this embodiment may include red, green, and blue color filters. The red, green, and blue color filters may be disposed in a delta arrangement.

A display apparatus 10 in FIG. 2 includes a substrate 11 made of glass or the like and a moistureproof film 12 that is disposed on the substrate 11 and protects TFT elements 18 or organic compound layers 22. Each of the TFT elements 18 includes a metal gate electrode 13, a gate insulating film 14, a semiconductor layer 15, a drain electrode 16, and a source electrode 17. An insulating film 19 is disposed on the TFT element 18. An anode 21 that constitutes an organic light-emitting element and the source electrode 17 are connected to each other through a contact hole 20. The form of electrical connection between electrodes (anode 21 and cathode 23) included in the organic light-emitting element and electrodes (source electrode 17 and drain electrode 16) included in the TFT is not limited to the form illustrated in FIG. 2. That is, it suffices that one of the anode 21 and the cathode 23 is electrically connected to one of the source electrode 17 and the drain electrode 16 of the TFT element. In the display apparatus 10 in FIG. 2, an organic compound layer 22 is illustrated as if having a single-layer structure, but may have a multilayer structure. A first protective layer 24 and a second protective layer 25 for suppressing the deterioration of the organic light-emitting element are disposed on the cathode 23.

In the display apparatus 10 in FIG. 2, a transistor is used as a switching element. Instead, an MIM element may be used as a switching element. The transistor used in the display apparatus 10 in FIG. 2 is not limited to transistors that use a single-crystal silicon wafer, but may be thin-film transistors including an active layer on an insulating surface of a substrate. Examples of the active layer include single-crystal silicon, amorphous silicon, non-single-crystal silicon such as microcrystalline silicon, and non-single-crystal oxide semiconductors such as indium zinc oxide and indium gallium zinc oxide. The thin-film transistors are also referred to as TFT elements. The transistor included in the display apparatus 10 in FIG. 2 may be formed in a substrate such as a Si substrate. Herein, the phrase "formed in a substrate" means that a transistor is produced by processing the substrate itself, such as a Si substrate. That is, a transistor formed in a substrate can be regarded as a transistor integrally formed with a substrate.

In the organic light-emitting element according to this embodiment, the emission luminance is controlled by a TFT that is an example of a switching element. When a plurality of such organic light-emitting elements are arranged in a plane, an image can be displayed using an emission luminance of each of the organic light-emitting elements. The switching element according to this embodiment is not limited to TFTs. The switching element may be a transistor formed of low-temperature polysilicon or an active matrix driver formed on a substrate such as a Si substrate. The phrase "on a substrate" may also refer to "in a substrate". The size of a display unit determines whether a transistor is disposed in a substrate or a TFT is used. For example, in the case of a size of about 0.5 inches, the organic light-emitting element may be disposed on a Si substrate.

Figure 3:
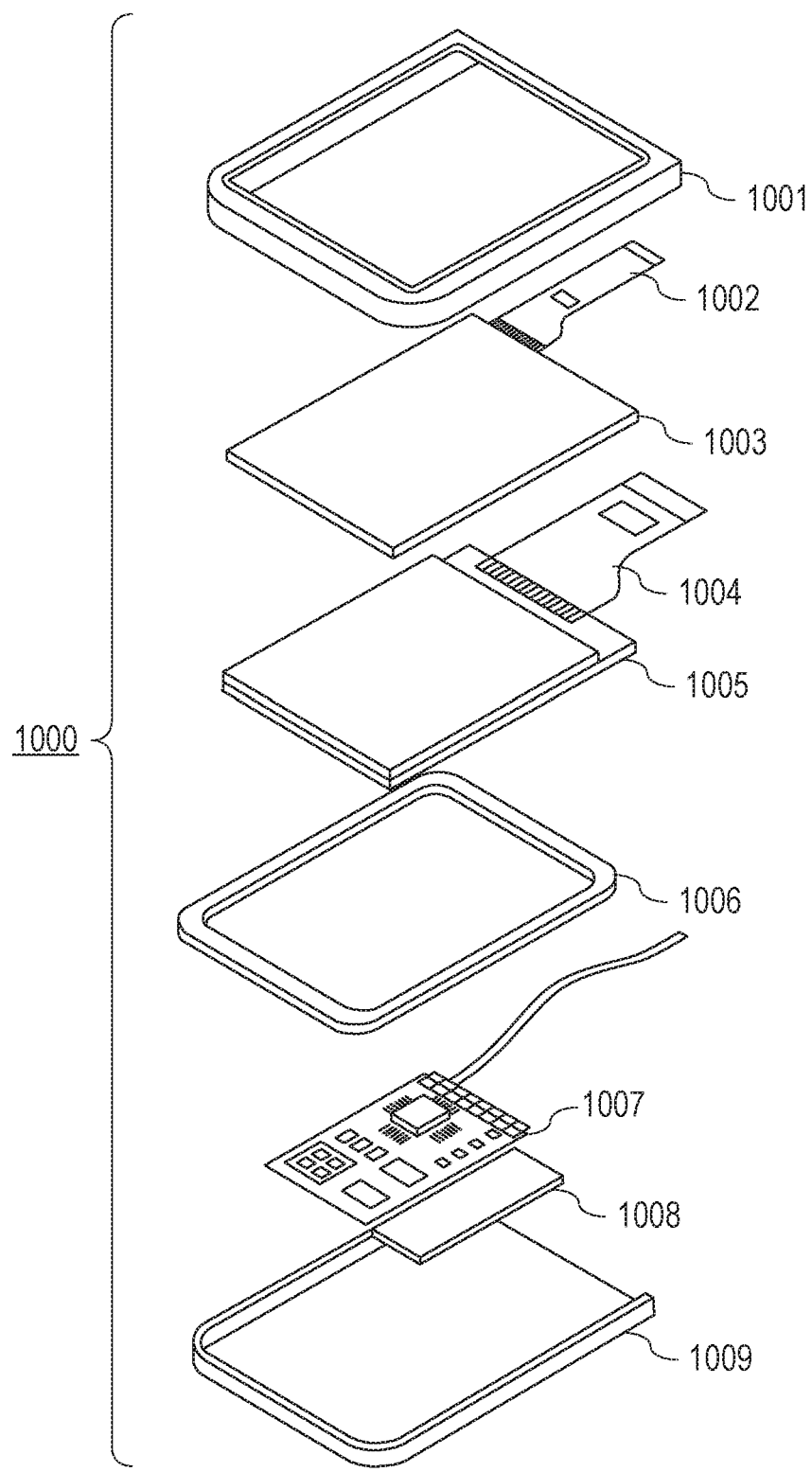
FIG. 3 schematically illustrates an example of a display apparatus according to this embodiment.

FIG. 3 schematically illustrates an example of a display apparatus according to this embodiment. A display apparatus 1000 may include a touch panel 1003, a display panel 1005, a frame 1006, a circuit board 1007, and a battery 1008 between an upper cover 1001 and a lower cover 1009. Flexible printed circuits FPC 1002 and 1004 are connected to the touch panel 1003 and the display panel 1005, respectively. The organic light-emitting element according to this embodiment may be used for the display panel 1005. A transistor is printed on the circuit board 1007. The battery 1008 is not necessarily disposed if the display apparatus is not a mobile apparatus. Even if the display apparatus is a mobile apparatus, the battery 1008 is not necessarily disposed at this position.

Figure 4A:
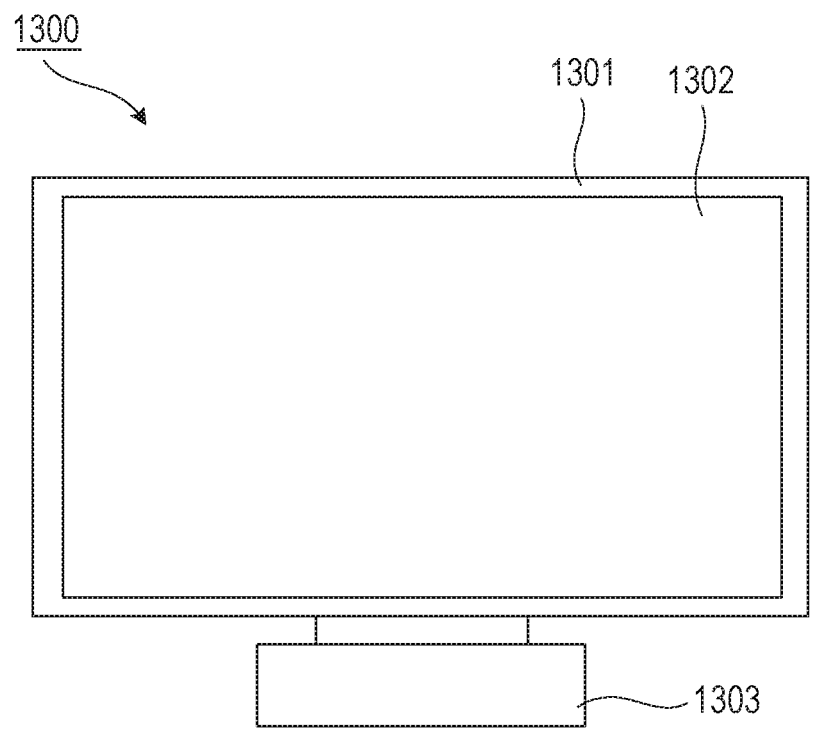
FIGS. 4A and 4B each schematically illustrate an example of a display apparatus according to this embodiment.
Figure 4B:
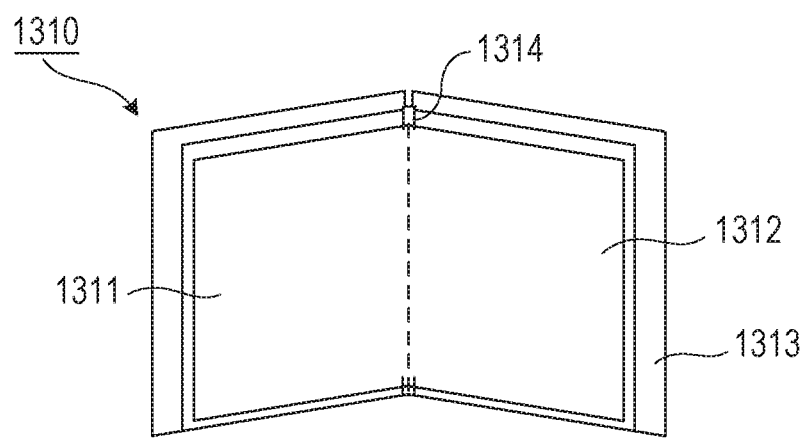

FIGS. 4A and 4B schematically illustrate examples of display apparatuses according to this embodiment. FIG. 4A illustrates a display apparatus such as a television monitor or a PC monitor. A display apparatus 1300 includes a frame 1301 and a display unit 1302. The organic light-emitting element according to this embodiment may be used for the display unit 1302. The display apparatus 1300 also includes a base 1303 that supports the frame 1301 and the display unit 1302. The form of the base 1303 is not limited to that in FIG. 4A. The lower side of the frame 1301 may also serve as a base. The frame 1301 and the display unit 1302 may be curved. The radius of curvature may be 5000 mm or more and 6000 mm or less. A display apparatus 1310 in FIG. 4B is a so-called foldable display apparatus. The display apparatus 1310 includes a first display unit 1311, a second display unit 1312, a housing 1313, and a bending point 1314. The first display unit 1311 and the second display unit 1312 may include the organic light-emitting element according to this embodiment. The first display unit 1311 and the second display unit 1312 may constitute a single seamless display apparatus. The first display unit 1311 and the second display unit 1312 can be divided by the bending point. The first display unit 1311 and the second display unit 1312 may display different images or a single image may be displayed in a combination of the first and second display units.

Photoelectric Conversion Apparatus

The display apparatus according to this embodiment may be used in a display unit of a photoelectric conversion apparatus such as an image pickup apparatus that includes an optical unit including a plurality of lenses and an image pickup element configured to receive light that has passed through the optical unit. The photoelectric conversion apparatus may include a display unit configured to display information obtained by the image pickup element. The display unit may be a display unit exposed to the outside of the photoelectric conversion apparatus or a display unit disposed in a viewfinder. The photoelectric conversion apparatus may be a digital camera or a digital video camera.

Figure 5:
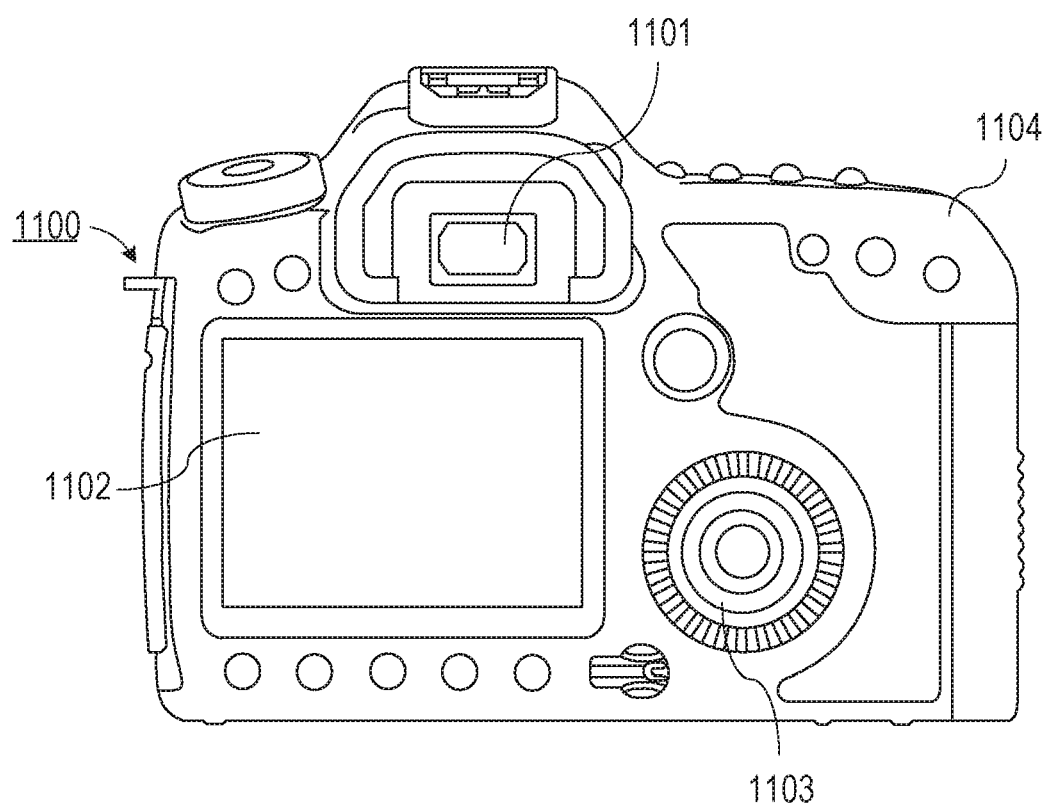
FIG. 5 schematically illustrates an example of an image pickup apparatus according to this embodiment.

FIG. 5 schematically illustrates an example of an image pickup apparatus according to this embodiment. An image pickup apparatus 1100 may include a viewfinder 1101, a rear display 1102, an operating unit 1103, and a housing 1104. The viewfinder 1101 may include the display apparatus according to this embodiment. In this case, the display apparatus may display not only an image to be captured, but also environmental information, image capturing instructions, and the like. The environmental information may be, for example, the intensity of external light, the direction of external light, the moving speed of a subject, and the possibility that the subject is hidden by an object. Since the timing appropriate for capturing an image is only a moment, the information is desirably displayed as quickly as possible. Therefore, the display apparatus including the organic light-emitting element according to an embodiment of the present disclosure can be used. This is because the organic light-emitting element has a high response speed. For apparatuses required to have a high display speed, the display apparatus including the organic light-emitting element can be more suitably used than liquid crystal display apparatuses. The image pickup apparatus 1100 includes an optical unit (not illustrated). The optical unit includes a plurality of lenses and focuses an image on the image pickup element accommodated in the housing 1104. By adjusting the relative positions of the plurality of lenses, the focal point can be adjusted. This operation can also be performed automatically.

Electronic Apparatus

Figure 6:
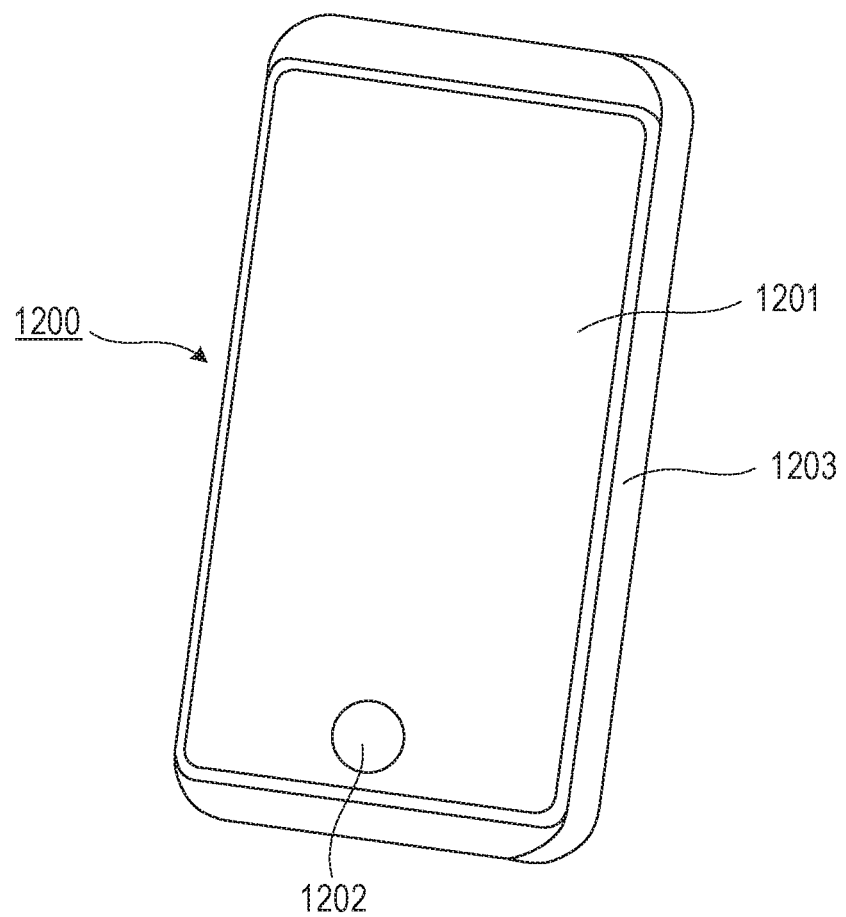
FIG. 6 schematically illustrates an example of a mobile apparatus according to this embodiment.

The display apparatus according to this embodiment may be used in a display unit of an electronic apparatus such as a mobile terminal. The display unit may have both a display function and an operational function. Examples of the mobile terminal include cellular phones such as smartphones, tablet computers, and head-mounted displays. FIG. 6 schematically illustrates an example of a mobile apparatus according to this embodiment. A mobile apparatus 1200 includes a display unit 1201, an operating unit 1202, and a housing 1203. The housing 1203 may include a circuit, a printed board including the circuit, a battery, and a communication unit. The operating unit 1202 may be a button or a touch panel response unit. The operating unit may be a biometric authentication unit that releases a lock through recognition of fingerprints. A mobile apparatus including a communication unit may be referred to as a communication apparatus.

Lighting Apparatus

Figure 7:
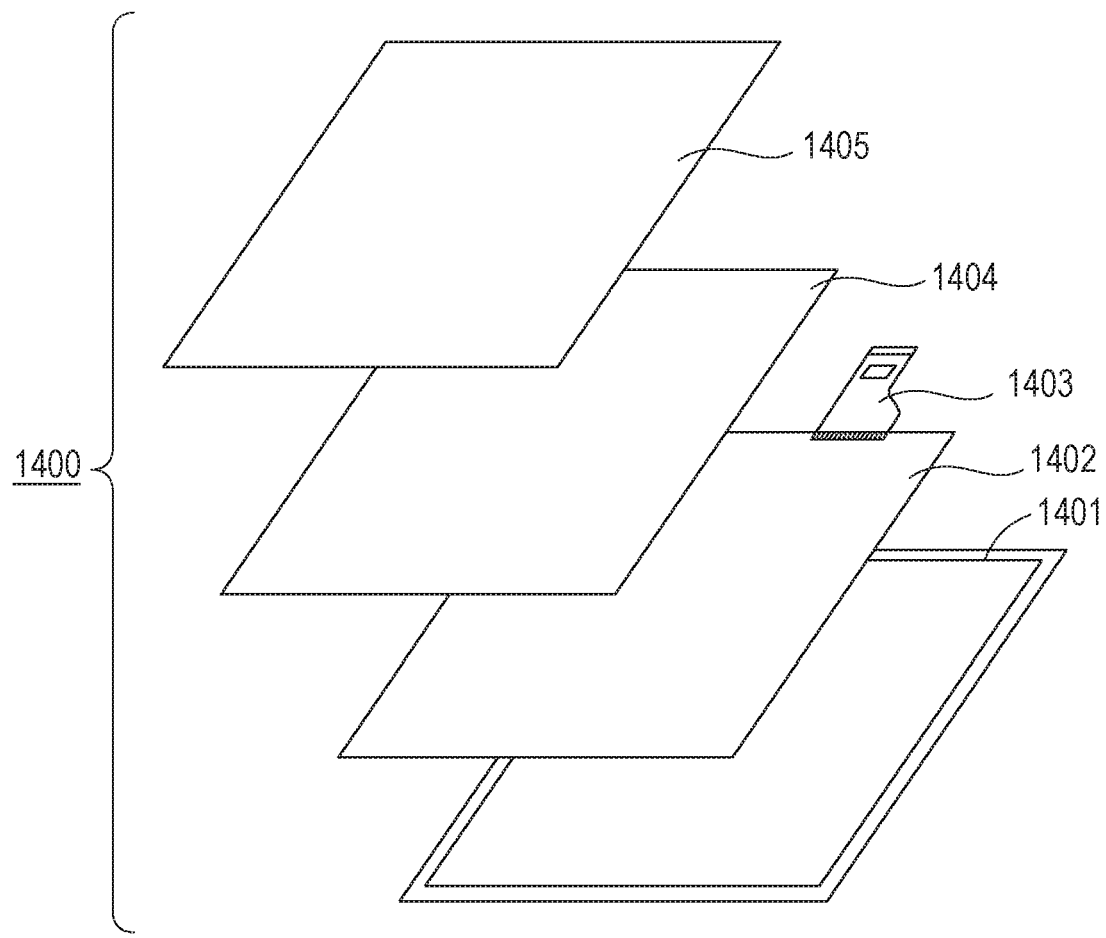
FIG. 7 schematically illustrates an example of a lighting apparatus according to this embodiment.

FIG. 7 schematically illustrates an example of a lighting apparatus according to this embodiment. A lighting apparatus 1400 may include a housing 1401, a light source 1402, a circuit board 1403, an optical filter 1404, and a light diffusion unit 1405. The light source 1402 may include the organic light-emitting element according to this embodiment. The optical filter 1404 may be a filter for improving the color rendering of the light source 1402. The light diffusion unit 1405 used for lighting up or the like effectively diffuses light from the light source 1402 and allows the light to reach a wide area. A cover may be optionally disposed on the outermost part.

The lighting apparatus is, for example, an apparatus that lights a room. The lighting apparatus may emit light of white, natural white, or any other color from blue to red. The lighting apparatus may include a light modulation circuit configured to modulate the light. The lighting apparatus may include the organic light-emitting element according to an embodiment of the present disclosure and a power supply circuit connected to the organic light-emitting element. The power supply circuit is a circuit that converts an alternating voltage to a direct voltage. The lighting apparatus may include an inverter circuit. The color "white" has a color temperature of 4200 K and the color "natural white" has a color temperature of 5000 K. The lighting apparatus may include a color filter. The lighting apparatus according to this embodiment may include a heat dissipation unit. The heat dissipation unit dissipates heat in the apparatus to the outside and is formed of, for example, a metal having a high specific heat or a liquid silicon.

Moving Object

Figure 8:
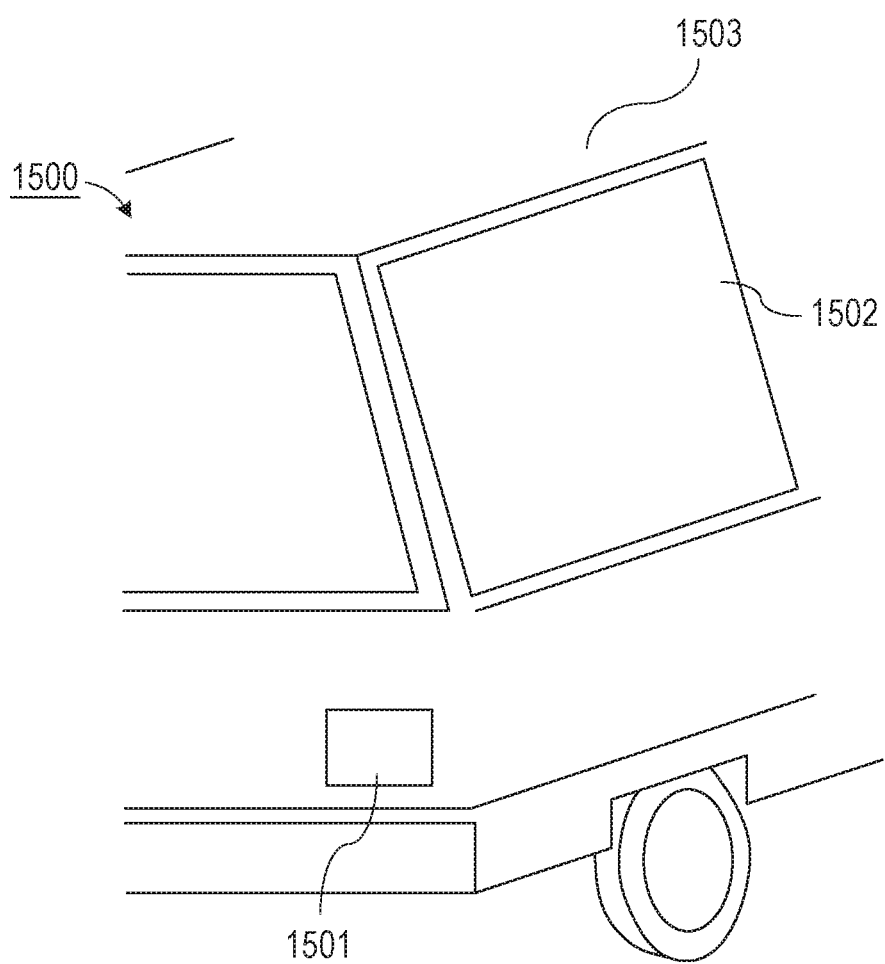
FIG. 8 schematically illustrates an example of a moving object according to this embodiment.

A moving object according to this embodiment may be, for example, an automobile, a ship, an aircraft, or a drone. The moving object may include a body and a lighting fixture disposed on the body. The lighting fixture may emit light for allowing the position of the body to be recognized. The lighting fixture may include the organic light-emitting element according to this embodiment. FIG. 8 schematically illustrates an example of a moving object according to this embodiment, which is an automobile including a tail lamp that is an example of a lighting fixture for vehicles. An automobile 1500 serving as a body includes a tail lamp 1501, and the tail lamp 1501 may be lit through, for example, application of the brake. The tail lamp 1501 may include the organic light-emitting element according to this embodiment. The tail lamp 1501 may include a protective member that protects the organic light-emitting element. The protective member may be made of any material as long as the protective member has a relatively high strength and transparency. The protective member may be made of polycarbonate or the like. The polycarbonate may be mixed with, for example, a furandicarboxylic acid derivative or an acrylonitrile derivative. The automobile 1500 may include a car body 1503 and windows 1502 attached to the car body 1503. The windows 1502 may be transparent displays as long as the windows 1502 are not a front or rear window of the automobile 1500. The transparent display may include the organic light-emitting element according to this embodiment. In this case, for example, the electrode included in the organic light-emitting element is formed of a transparent material.

EXAMPLES

Hereafter, the present disclosure will be described based on Examples, but is not limited to Examples.

Example 1 (Synthesis of Exemplary Compound A2)

(1) Synthesis of Compound E3

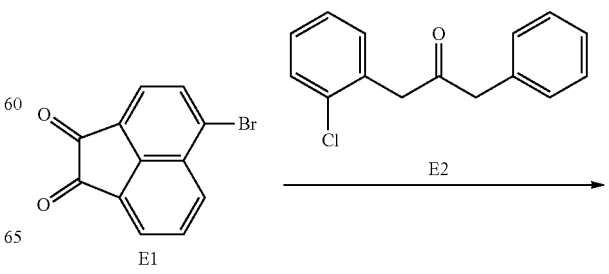

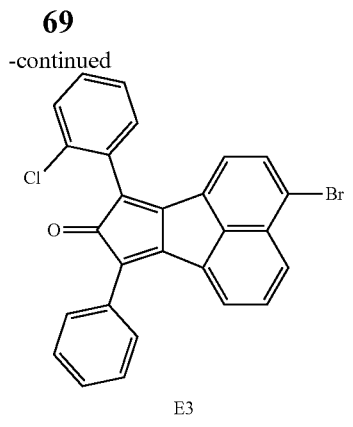

E3

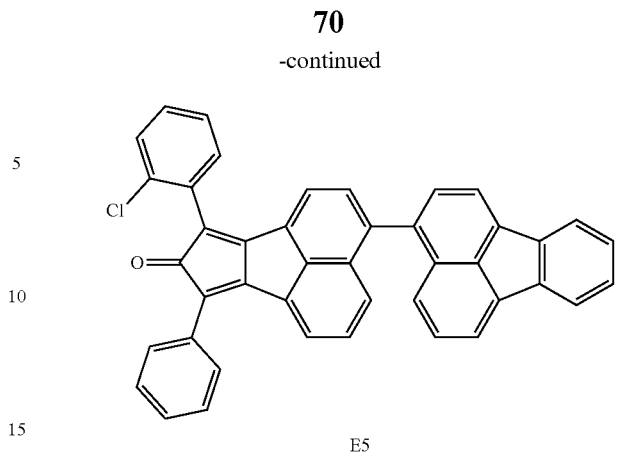

E5

The following reagents and solvent were charged into a 100 ml recovery flask.
Compound E1: 2.00 g (7.66 mmol)
Compound E2: 1.97 g (8.04 mmol)
Ethanol: 40 ml Subsequently, a solution prepared by dissolving 556 mg (8.43 mmol) of 85% sodium hydroxide in 10 ml of ethanol was added dropwise thereto at room temperature. After the completion of the dropwise addition, the temperature was increased to 40° C. in a nitrogen stream, and stirring was performed at this temperature (40° C.) for 4 hours. After the completion of the reaction, water was added and the resulting product was filtered and washed by dispersion with water and methanol. Thus, 3.20 g of a dark green compound E3 (yield: 89%) was obtained.

(2) Synthesis of Compound E5

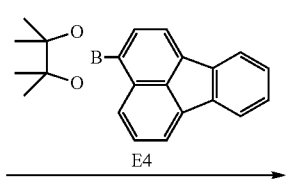

E3

The following reagents and solvents were charged into a 200 ml recovery flask.
Compound E3: 3.00 g (6.39 mmol)
Compound E4: 2.20 g (6.71 mmol)
Pd(PPh$_3$)$_4$: 221 mg (0.192 mmol)
Sodium carbonate: 1.35 g (12.8 mmol)
Toluene: 50 ml
Ethanol: 25 ml
Water: 25 ml Subsequently, the reaction solution was heated to 90° C. in a nitrogen stream and stirred at this temperature (90° C.) for 4 hours. After the completion of the reaction, the resulting product was extracted with toluene and water, then concentrated, purified by silica gel column chromatography (heptane:toluene=1:1), and then washed by dispersion with methanol. Thus, 3.02 g (yield: 80%) of a black compound E5 was obtained.

(3) Synthesis of Compound E7

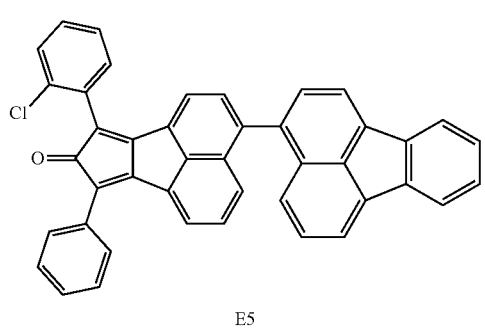

E5

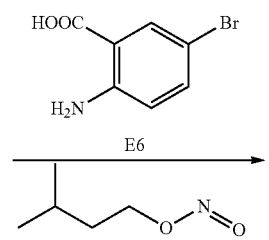

E6

-continued

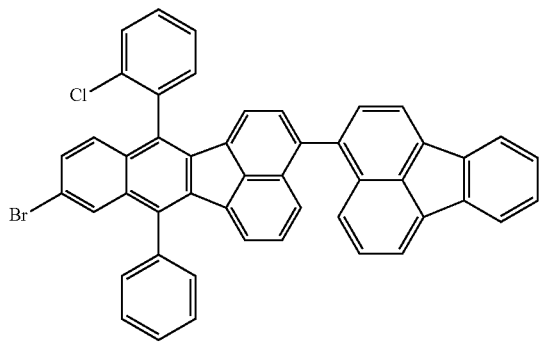

E7

The following reagents and solvent were charged into a 100 ml recovery flask.

Compound E5: 2.80 g (4.74 mmol)
Compound E6: 1.43 g (6.63 mmol)
Isoamyl nitrite: 888 mg (7.58 mmol)
Toluene: 50 ml Subsequently, the reaction solution was heated to 105° C. in a nitrogen stream and stirred at this temperature (105° C.) for 2 hours. Furthermore, 1.02 g (4.74 mmol) of the compound E6 and 666 mg (5.69 mmol) of the isoamyl nitrite were added thereto, and stirring was performed for 2 hours. After the completion of the reaction, the resulting product was extracted with toluene and water, then concentrated, purified by silica gel column chromatography (heptane:toluene=4:1), and then washed by dispersion with ethanol. Thus, 2.21 g of a yellow compound E7 (yield: 65%) was obtained.

(4) Synthesis of Compound E8

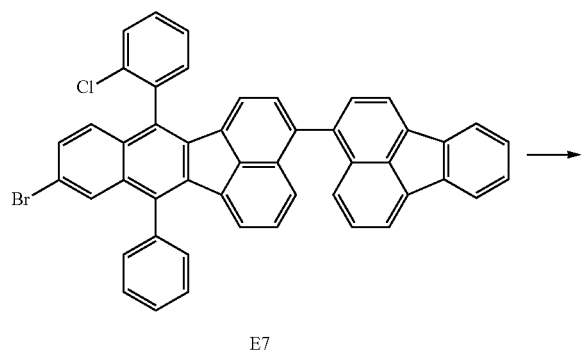

E7

→

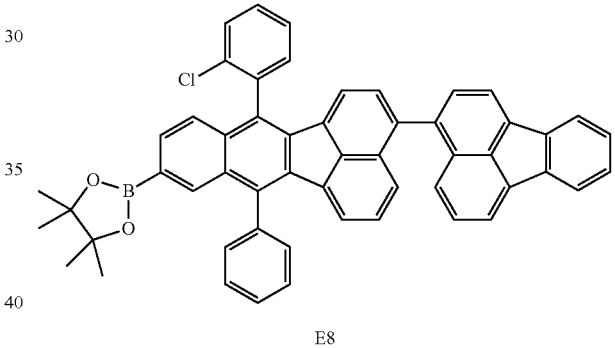

E8

The following reagents and solvent were charged into a 100 ml recovery flask.

Compound E7: 2.10 g (2.92 mmol)
Bis(pinacolborane): 1.48 g (5.84 mmol)
PdCl$_2$(dppf)$_2$: 62 mg (0.088 mmol)
Potassium acetate: 860 mg (8.76 mmol)
Toluene: 30 ml Subsequently, the reaction solution was heated to 90° C. in a nitrogen stream and stirred at this temperature (90° C.) for 4 hours. After the completion of the reaction, the resulting product was concentrated, purified by silica gel column chromatography (heptane:toluene=1:1), and then washed by dispersion with methanol. Thus, 1.52 g of a yellow compound E8 (yield: 68%) was obtained.

(5) Synthesis of Compound E10

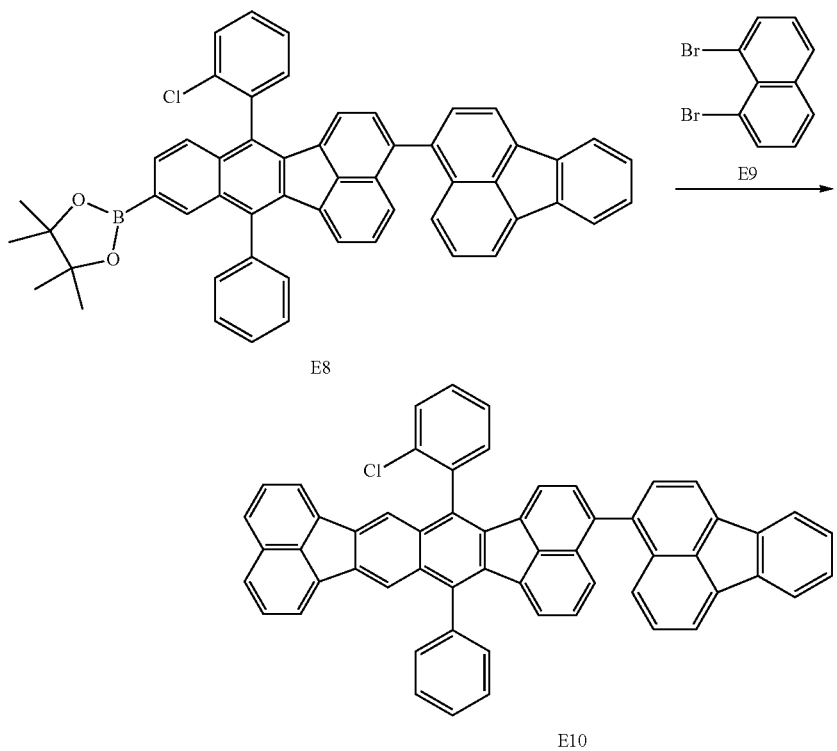

The following reagents and solvent were charged into a 50 ml recovery flask.
Compound E8: 1.80 g (2.35 mmol)
Compound E9: 673 mg (2.35 mmol)
$PdCl_2(PPh_3)_2$: 329 mg (0.47 mmol)
DBU: 1.41 g (9.40 mmol)
DMAc: 30 ml Subsequently, the reaction solution was heated to 170° C. in a nitrogen stream and stirred at this temperature (170° C.) for 24 hours. After the completion of the reaction, the resulting product was extracted with toluene and water, then concentrated, purified by silica gel column chromatography (heptane:toluene=4:1), and then washed by dispersion with heptane/ethanol. Thus, 448 mg of a yellow compound E10 (yield: 25%) was obtained.

(6) Synthesis of Compound E11

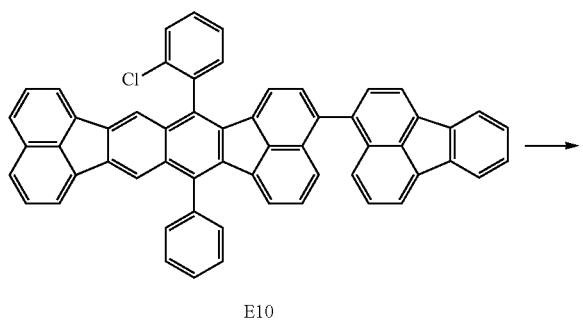

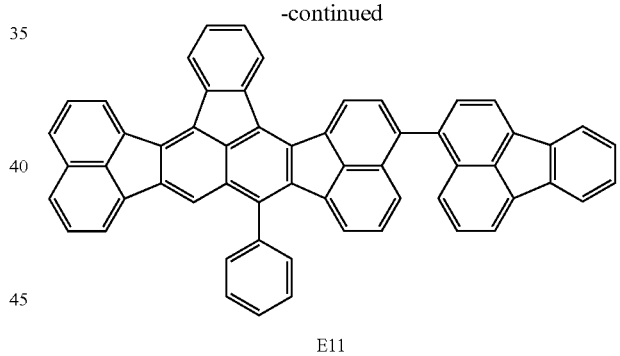

The following reagents and solvent were charged into a 50 ml recovery flask.
Compound E8: 420 mg (0.550 mmol)
$Pd(dba)_2$: 95 mg (0.165 mmol)
$P(Cy)_3$: 95 mg (0.34 mmol)
DBU: 0.25 g (1.65 mmol)
DMAc: 10 ml Subsequently, the reaction solution was heated to 170° C. in a nitrogen stream and stirred at this temperature (170° C.) for 12 hours. After the completion of the reaction, the resulting product was extracted with toluene and water, then concentrated, purified by silica gel column chromatography (heptane:toluene=4:1), and then washed by dispersion with heptane/ethanol. Thus, 312 mg of a yellow compound E11 (yield: 78%) was obtained.

(7) Synthesis of Exemplary Compound A2

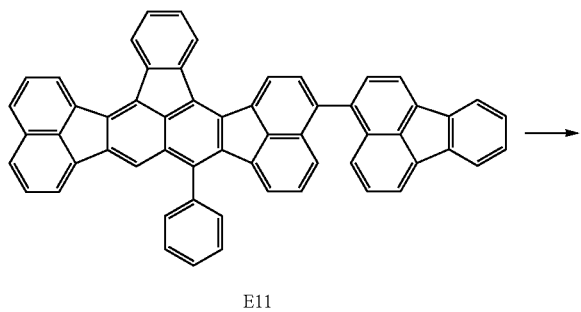

E11

↓

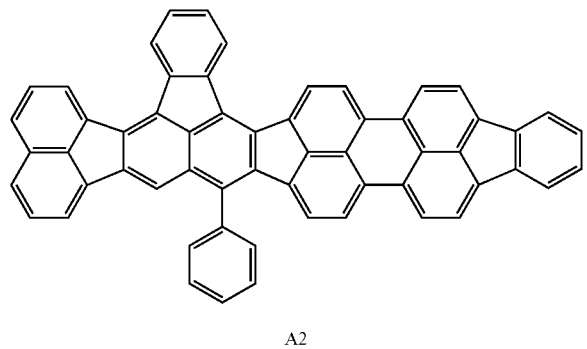

A2

The following reagents and solvent were charged into a 20 ml recovery flask.

Compound E11: 300 mg (0.413 mmol)
t-BuOK: 1.39 g (12.4 mmol)
DBU (diazabicycloundecene): 3.71 ml (24.8 mmol)
Diethylene glycol dimethyl ether: 12 ml Subsequently, the reaction solution was heated to 180° C. in a nitrogen stream and stirred at this temperature (180° C.) for 10 hours. After the completion of the reaction, water was added to precipitate a crystal. Then, the crystal was separated by filtration and sequentially washed by dispersion with water, methanol, ethanol, and heptane. Subsequently, the obtained deep purple solid was dissolved in chlorobenzene at 130° C., and alumina was added thereto to perform a heat adsorption process. The resulting product was hot-filtered, concentrated, and washed by dispersion with acetone/heptane. Thus, 225 mg of a deep purple exemplary compound A2 (yield: 75%) was obtained.

A toluene solution of the exemplary compound A2 in a concentration of $1\times10^{-5}$ mol/L was subjected to photoluminescence measurement at an excitation wavelength of 350 nm using an F-4500 manufactured by Hitachi, Ltd. The emission spectrum showed a peak having the maximum intensity at 598 nm.

The exemplary compound A2 was subjected to mass spectrometry using MALDI-TOF-MS (Autoflex LRF manufactured by Bruker).

MALDI-TOF-MS
Measured value: m/z=725, Calculated value: $C_{52}H_{26}$=725

Examples 2 to 17 (Synthesis of Exemplary Compound)

Exemplary compounds shown in Tables 4 to 6 were synthesized in the same manner as in Example 1, except that the raw materials E2, E4, and E9 in Example 1 were changed to raw materials 1, 2, and 3. The exemplary compounds were subjected to mass spectrometry in the same manner as in Example 1 to determine the measured value m/z.

TABLE 4

| Example | Exemplary compound | Raw material 1 |
|---|---|---|
| 2 | 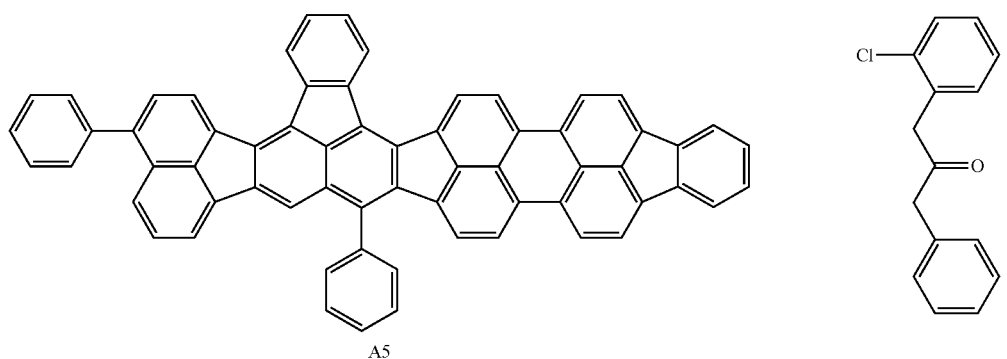 A5 | |

TABLE 4-continued
| | | |
|---|---|---|
| 3 | 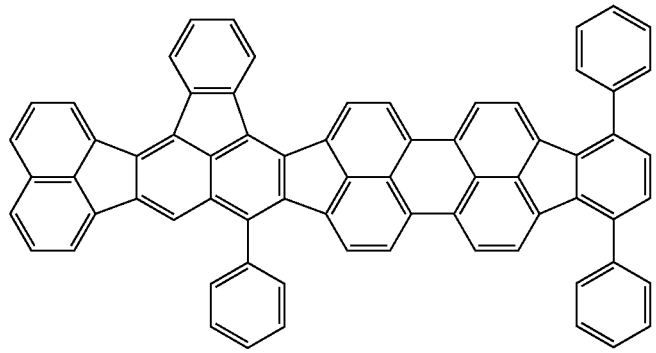<br>A8 | 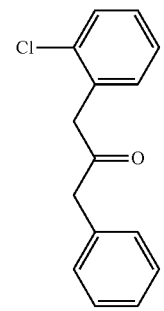 [SMILES: O=C(Cc1ccccc1)Cc1ccccc1Cl] |
| 4 | 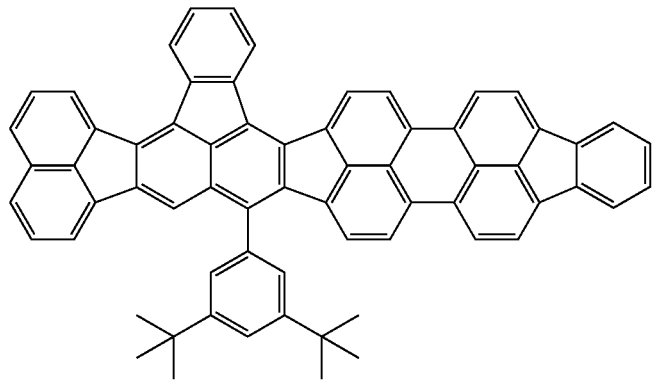<br>A11 | 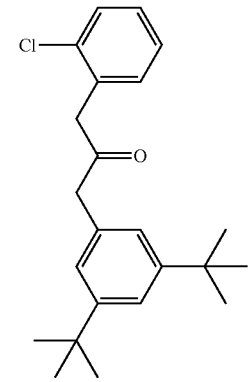 [SMILES: CC(C)(C)c1cc(CC(=O)Cc2ccccc2Cl)cc(C(C)(C)C)c1] |
| 5 | 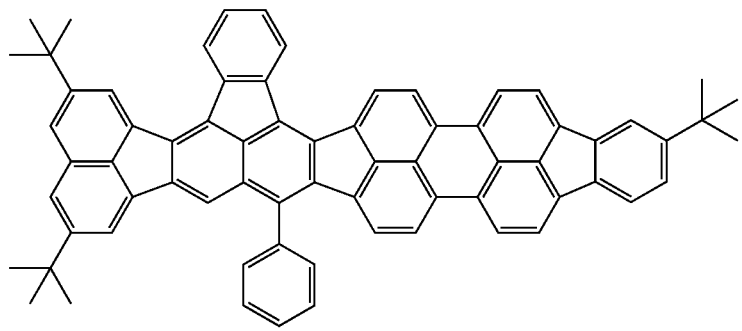<br>A13 | 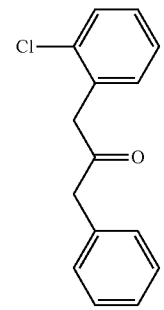 [SMILES: O=C(Cc1ccccc1)Cc1ccccc1Cl] |
| Example | Raw material 2 | Raw material 3 | m/z |
|---|---|---|---|
| 2 | 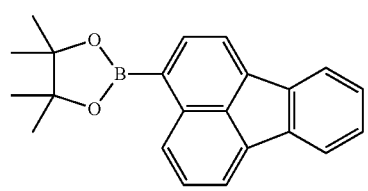 [SMILES: CC1(C)OB(c2ccc3c4c(cccc24)-c2ccccc2-3)OC1(C)C] | 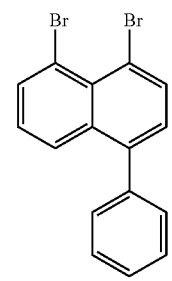 [SMILES: Brc1cccc2c(-c3ccccc3)ccc(Br)c12] | 801 |

TABLE 4-continued
| | | | |
|---|---|---|---|
| 3 | 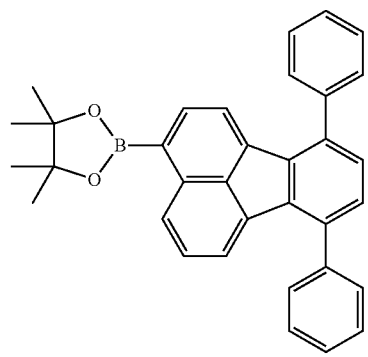 [SMILES: CC1(C)OB(c2ccc3c4c(cccc24)-c2c(-c4ccccc4)ccc(-c4ccccc4)c2-3)OC1(C)C] | 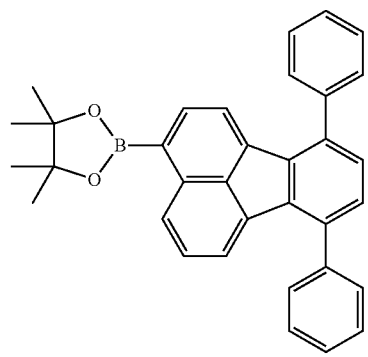 [SMILES: CC1(C)OB(c2ccc3c4c(cccc24)-c2c(-c4ccccc4)ccc(-c4ccccc4)c2-3)OC1(C)C] | 877 |
| 4 | 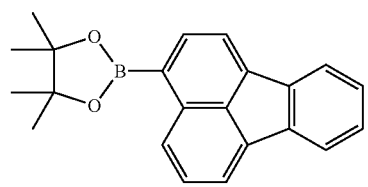 [SMILES: CC1(C)OB(c2ccc3c4c(cccc24)-c2ccccc2-3)OC1(C)C] | 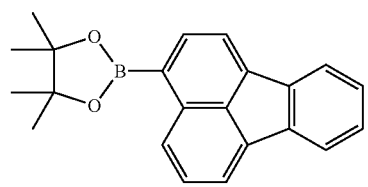 [SMILES: CC1(C)OB(c2ccc3c4c(cccc24)-c2ccccc2-3)OC1(C)C] | 837 |
| 5 | 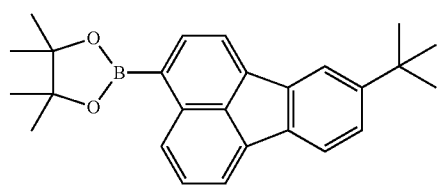 [SMILES: CC(C)(C)c1ccc2c(c1)-c1ccc(B3OC(C)(C)C(C)(C)O3)c3cccc-2c13] | 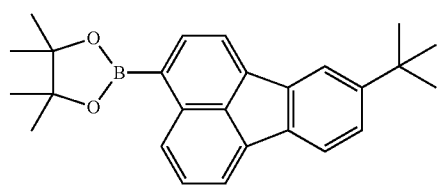 [SMILES: CC(C)(C)c1ccc2c(c1)-c1ccc(B3OC(C)(C)C(C)(C)O3)c3cccc-2c13] | 893 |
TABLE 5
| | | |
|---|---|---|
| 6 | 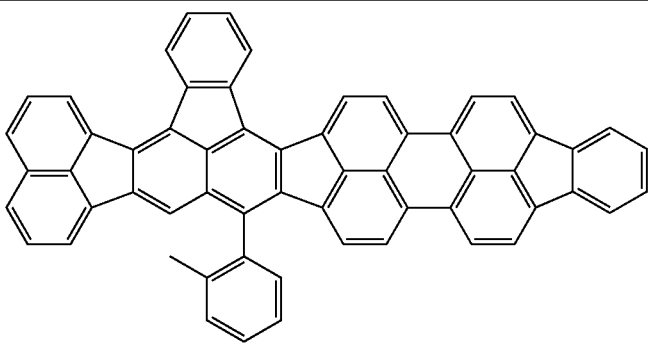 B1 | 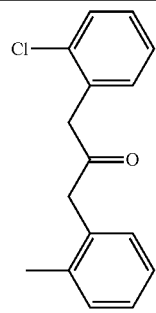 |
| 7 | 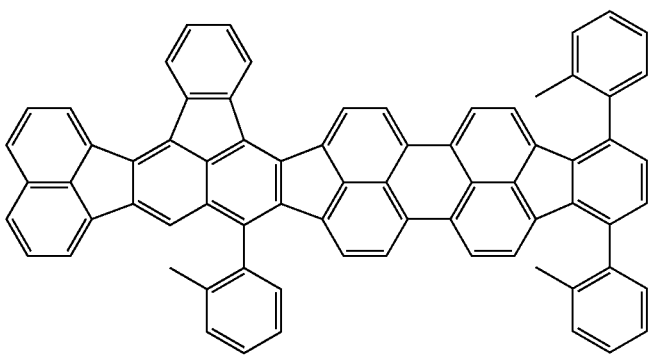 B3 | 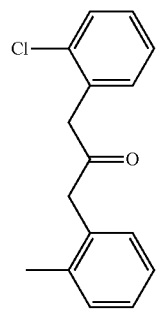 [SMILES: Cc1ccccc1CC(=O)Cc1ccccc1Cl] |

TABLE 5-continued
| | | |
|---|---|---|
| 8 | 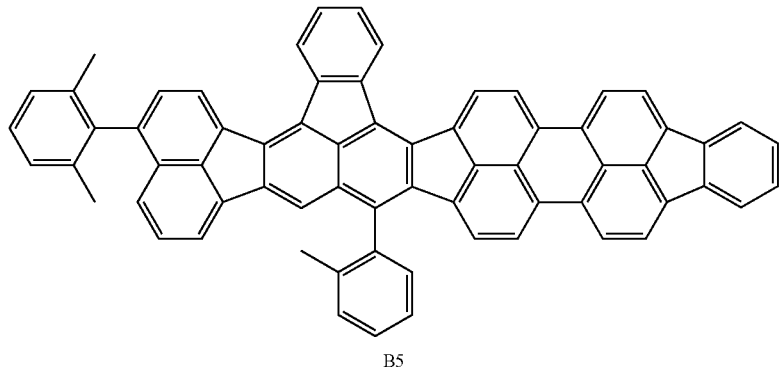<br>B5 | 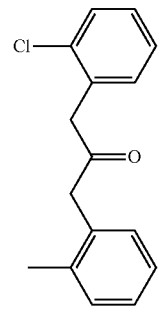 [SMILES: Cc1ccccc1CC(=O)Cc1ccccc1Cl] |
| 9 | 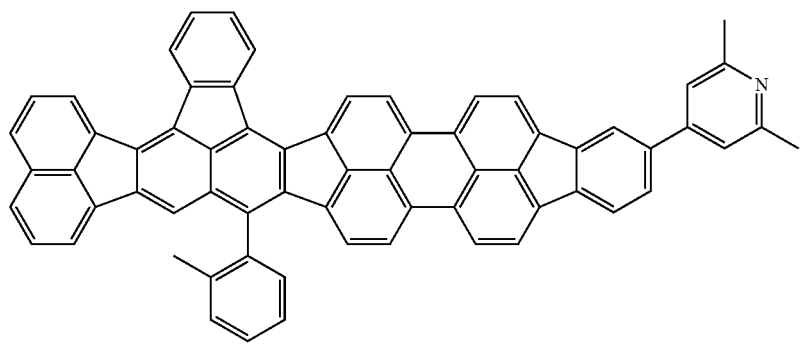<br>B9 | 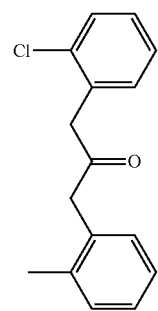 [SMILES: Cc1ccccc1CC(=O)Cc1ccccc1Cl] |
| 10 | 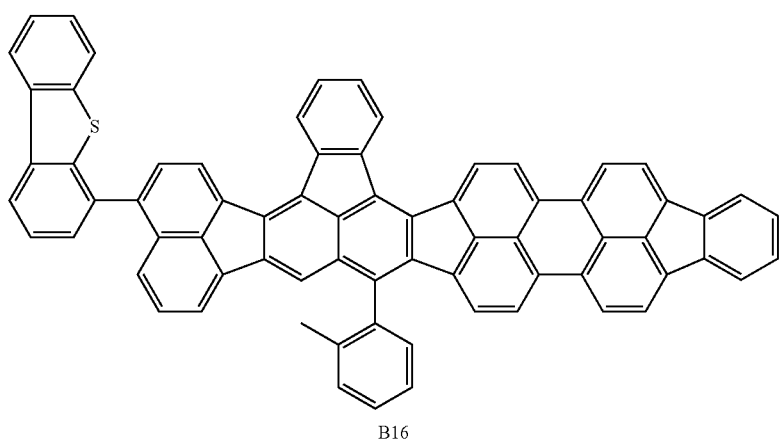<br>B16 | 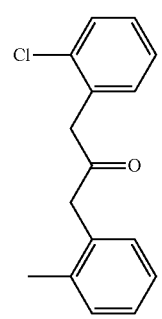 [SMILES: Cc1ccccc1CC(=O)Cc1ccccc1Cl] |
| 6 | 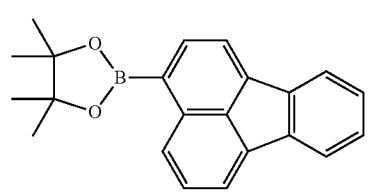 | 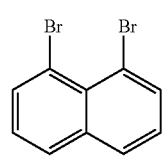 739 |

TABLE 5-continued
| | | | |
|---|---|---|---|
| 7 | 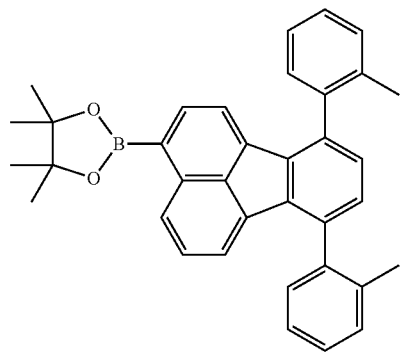 | 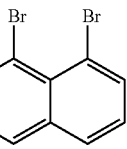 | 919 |
| 8 | 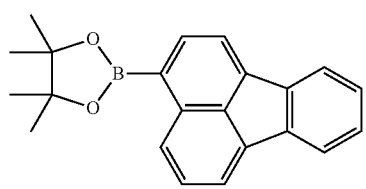 [SMILES: CC1(C)OB(c2ccc3c4c(cccc24)-c2ccccc2-3)OC1(C)C] | 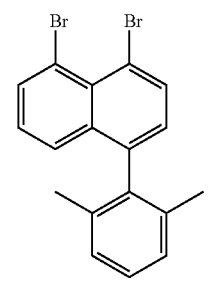 [SMILES: Cc1cccc(C)c1-c1ccc(Br)c2c(Br)cccc12] | 843 |
| 9 | 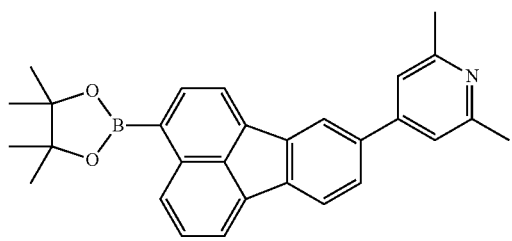 | 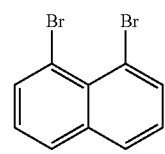 | 844 |
| 10 | 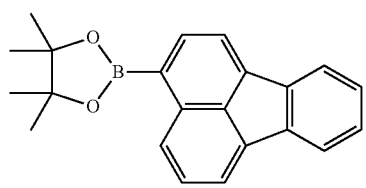 [SMILES: CC1(C)OB(c2ccc3c4c(cccc24)-c2ccccc2-3)OC1(C)C] | 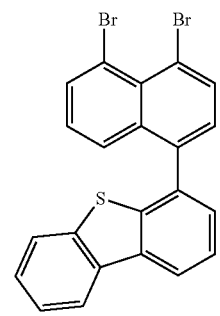 [SMILES: Brc1cccc2c(-c3cccc4c3sc3ccccc34)ccc(Br)c12] | 921 |

TABLE 6
| | | |
|---|---|---|
| 11 | 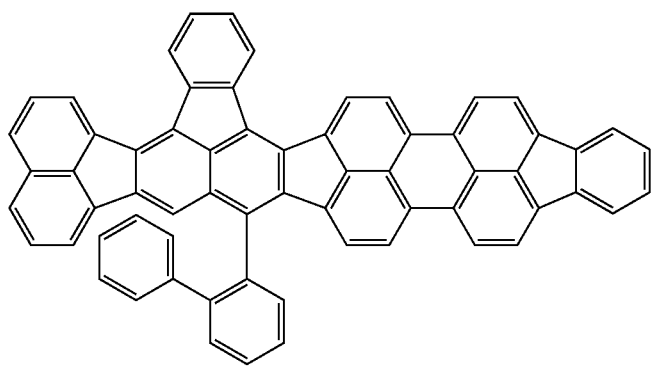<br>C1 | 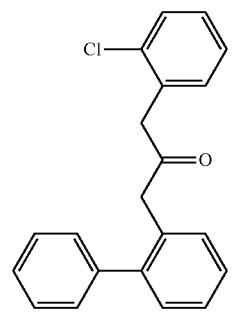 [SMILES: O=C(Cc1ccccc1Cl)Cc1ccccc1-c1ccccc1] |
| 12 | 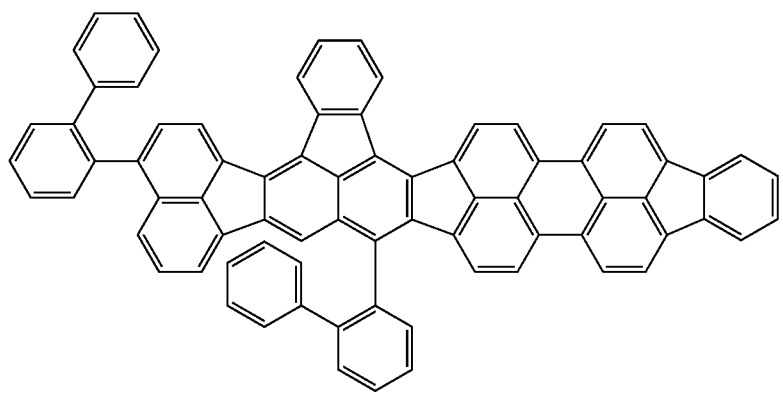<br>C3 | 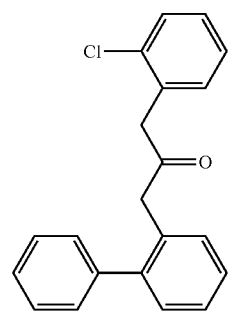 [SMILES: O=C(Cc1ccccc1Cl)Cc1ccccc1-c1ccccc1] |
| 13 | 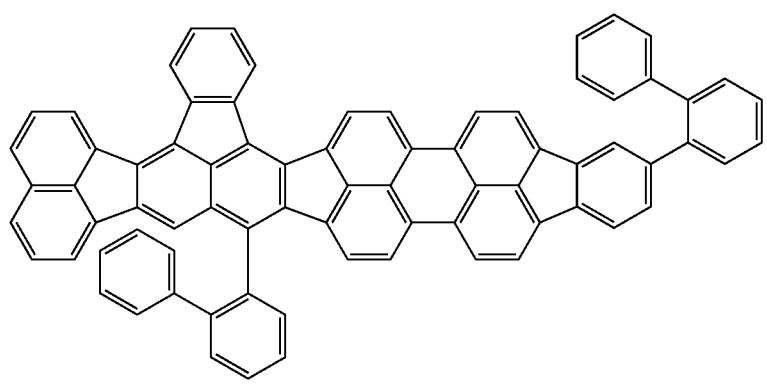<br>C5 | 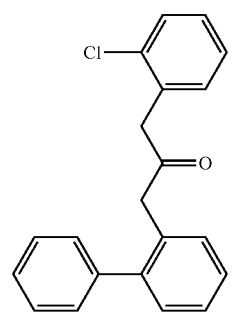 [SMILES: O=C(Cc1ccccc1Cl)Cc1ccccc1-c1ccccc1] |
| 14 | 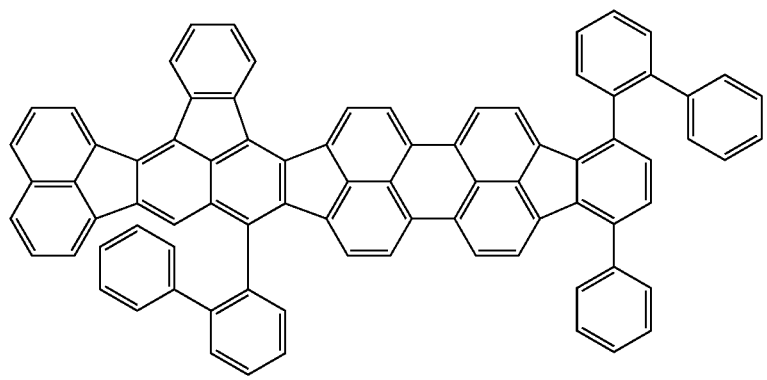<br>C6 | 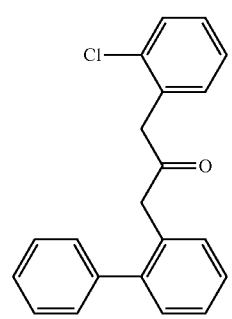 [SMILES: O=C(Cc1ccccc1Cl)Cc1ccccc1-c1ccccc1] |

TABLE 6-continued
| 15 | 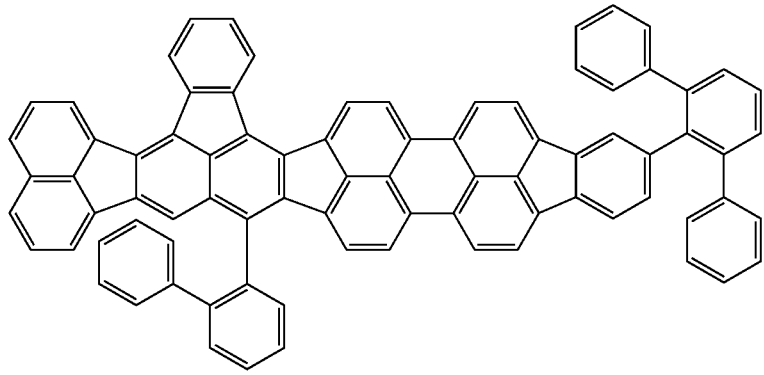 C7 | 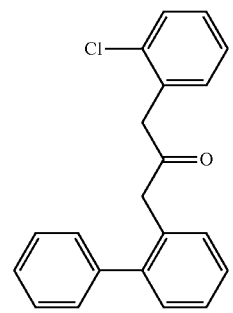 [SMILES: O=C(Cc1ccccc1Cl)Cc1ccccc1-c1ccccc1] |
| --- | --- | --- |
| 16 | 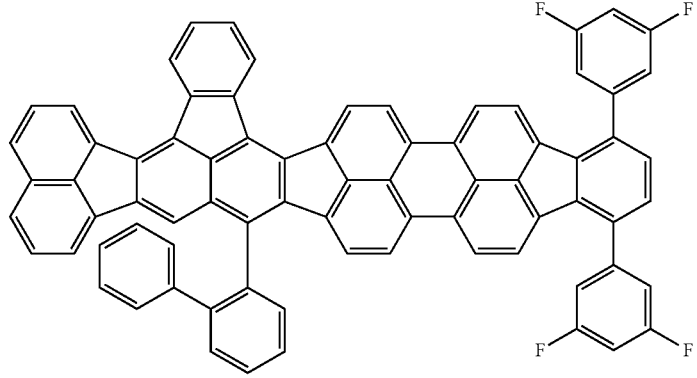 C12 | 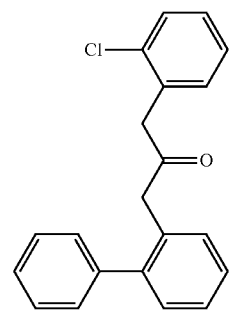 [SMILES: O=C(Cc1ccccc1Cl)Cc1ccccc1-c1ccccc1] |
| 17 | 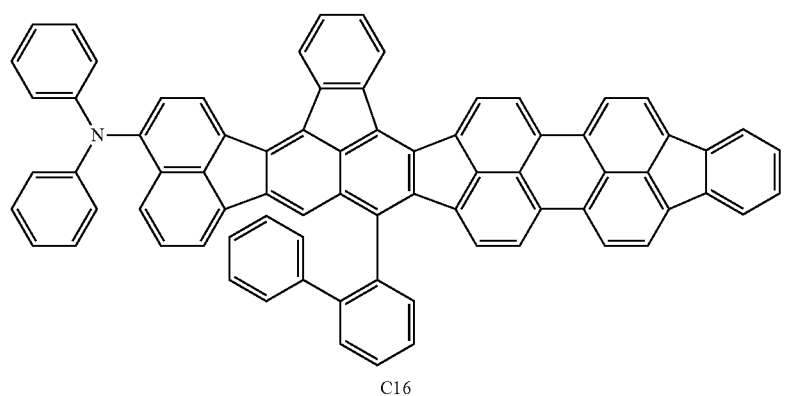 C16 | 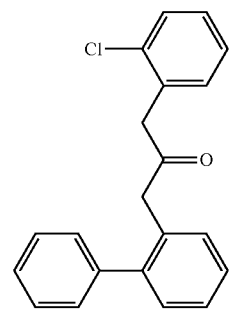 [SMILES: O=C(Cc1ccccc1Cl)Cc1ccccc1-c1ccccc1] |

TABLE 6-continued
| 11 | 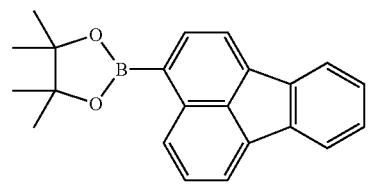 | 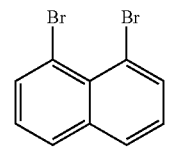 [SMILES: Brc1cccc2cccc(Br)c12] | 801 |
| 12 | 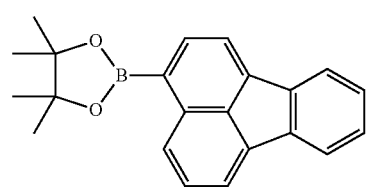 | 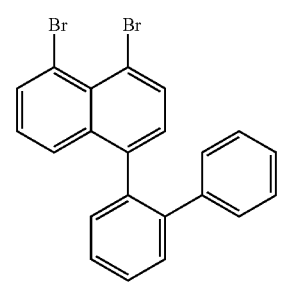 [SMILES: Brc1cccc2c(-c3ccccc3-c3ccccc3)ccc(Br)c12] | 953 |
| 13 | 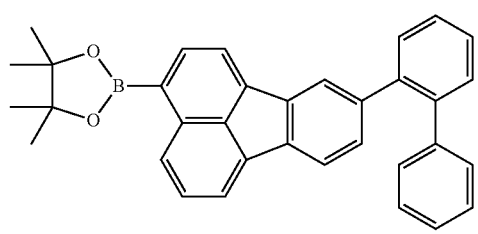 | 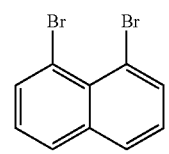 | 953 |
| 14 | 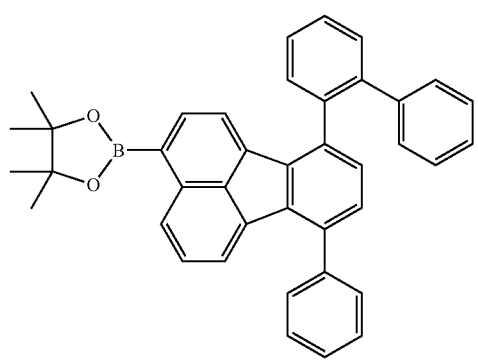 | 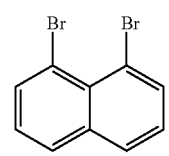 | 1029 |

TABLE 6-continued

| | | | |
|---|---|---|---|
| 15 | 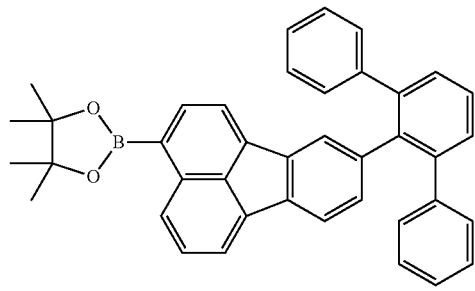 [SMILES: CC1(C)OB(c2ccc3c4c(cccc24)-c2ccc(-c4c(-c5ccccc5)cccc4-c4ccccc4)cc2-3)OC1(C)C] | 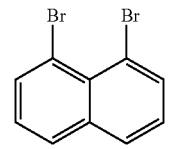 | 1029 |
| 16 | 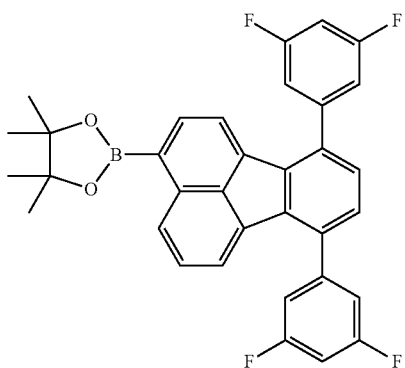 [SMILES: CC1(C)OB(c2ccc3c4c(cccc24)-c2c(-c4cc(F)cc(F)c4)ccc(-c4cc(F)cc(F)c4)c2-3)OC1(C)C] | 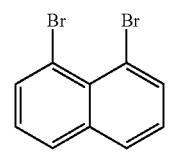 [SMILES: Brc1cccc2cccc(Br)c12] | 1025 |
| 17 | 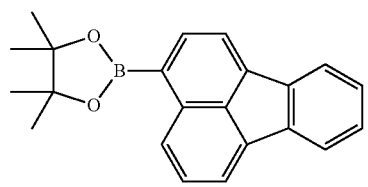 [SMILES: CC1(C)OB(c2ccc3c4c(cccc24)-c2ccccc2-3)OC1(C)C] | 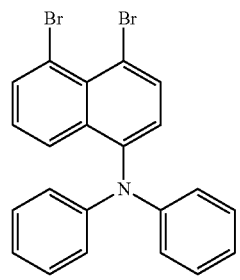 [SMILES: Brc1cccc2c(N(c3ccccc3)c3ccccc3)ccc(Br)c12] | 968 |

Example 18

A bottom-emission organic light-emitting element was produced in which an anode, a hole injection layer, a hole transport layer, an electron blocking layer, a light-emitting layer, a hole blocking layer, an electron transport layer, an electron injection layer, and a cathode were sequentially formed on a substrate.

First, ITO was deposited on a glass substrate, and a desired patterning process was performed to form an ITO electrode (anode). At this time, the thickness of the ITO electrode was set to 100 nm. Such a substrate on which the ITO electrode was formed was used as an ITO substrate in the following process. Subsequently, the organic compound layers and the electrode layer shown in Table 7 were successively formed on the ITO substrate by performing vacuum vapor deposition through resistance heating in a vacuum chamber at $1.33 \times 10^{-4}$ Pa. At this time, the electrode area of a counter electrode (metal electrode layer, cathode) was set to 3 $mm^2$.

TABLE 7

|  | Material |  | Thickness (nm) |
| --- | --- | --- | --- |
| Cathode | Al |  | 100 |
| Electron injection layer (EIL) | LiF |  | 1 |
| Electron transport layer (ETL) | ET5 |  | 20 |
| Hole blocking layer (HBL) | ET17 |  | 20 |
| Light-emitting layer (EML) | Host EM17<br>Guest A2 | Mass ratio<br>EM17:A2 = 99.7:0.3 | 30 |
| Electron blocking layer (EBL) | HT12 |  | 15 |
| Hole transport layer (HTL) | HT3 |  | 30 |
| Hole injection layer (HIL) | HT16 |  | 5 |

The characteristics of the obtained element were measured and evaluated. The light-emitting element had a maximum emission wavelength of 617 nm and a maximum external quantum efficiency (E.Q.E.) of 4.5%, and emitted red light with a chromaticity of (X, Y)=(0.67, 0.33). Furthermore, a continuous driving test at a current density of 100 mA/cm$^2$ was performed to measure a time taken when the luminance decrease reached 5%. The time was more than 500 hours. For the measuring instruments, specifically, the current-voltage characteristics were measured with a microammeter 4140B manufactured by Hewlett-Packard Company, and the emission luminance was measured with a BM7 manufactured by TOPCON Corporation.

(5) Synthesis of Compound E10

Examples 19 to 30 and Comparative Example 1

Organic light-emitting elements were produced in the same manner as in Example 18, except that the compounds in Example 18 were appropriately changed to those in Table 8. The characteristics of the obtained elements were measured and evaluated in the same manner as in Example 18. Table 8 shows the measurement results.

As is clear from Table 8, the chromaticity coordinates in Comparative Example 1 are (0.65, 0.34). The red-light-emitting elements according to an embodiment of the present disclosure tend to achieve a color reproduction range wider than the color reproduction range of sRGB. This is because the compound according to an embodiment of the present disclosure emits red light having a longer wavelength.

Example 31

A top-emission organic light-emitting element was produced in which an anode, a hole injection layer, a hole transport layer, an electron blocking layer, a first light-emitting layer, a second light-emitting layer, a hole blocking layer, an electron transport layer, an electron injection layer, and a cathode were sequentially formed on a substrate.

A Ti film having a thickness of 40 nm was formed on a glass substrate by a sputtering method and patterned by photolithography to form an anode. At this time, the electrode area of a counter electrode (metal electrode layer,

TABLE 8

|  |  |  |  | EML |  |  |  | E.Q.E [%] | Chromaticity coordinates of red (x, y) |
| --- | --- | --- | --- | --- | --- | --- | --- | --- | --- |
|  | HIL | HTL | EBL | Host | Guest | HBL | ETL |  |  |
| Example 19 | HT16 | HT3 | HT11 | EM17 | A8 | ET17 | ET5 | 4.7 | (0.69, 0.32) |
| Example 20 | HT16 | HT2 | HT12 | EM17 | A11 | ET12 | ET2 | 4.8 | (0.67, 0.33) |
| Example 21 | HT16 | HT2 | HT8 | EM16 | A11 | ET10 | ET3 | 4.8 | (0.68, 0.33) |
| Example 22 | HT16 | HT2 | HT12 | EM17 | B1 | ET12 | ET2 | 4.7 | (0.67, 0.33) |
| Example 23 | HT16 | HT1 | HT8 | EM16 | B3 | ET18 | ET3 | 4.8 | (0.68, 0.32) |
| Example 24 | HT16 | HT2 | HT12 | EM16 | B5 | ET12 | ET2 | 4.8 | (0.68, 0.33) |
| Example 25 | HT16 | HT2 | HT8 | EM17 | B9 | ET11 | ET2 | 4.7 | (0.68, 0.32) |
| Example 26 | HT16 | HT2 | HT8 | EM17 | C1 | ET18 | ET2 | 4.8 | (0.68, 0.33) |
| Example 27 | HT16 | HT1 | HT12 | EM16 | C3 | ET10 | ET2 | 4.8 | (0.69, 0.32) |
| Example 28 | HT16 | HT1 | HT12 | EM16 | C5 | ET10 | ET3 | 4.8 | (0.69, 0.32) |
| Example 29 | HT16 | HT2 | HT8 | EM17 | C7 | ET18 | ET3 | 4.9 | (0.69, 0.32) |
| Example 30 | HT17 | HT6 | HT8 | EM17 | C11 | ET18 | ET3 | 4.9 | (0.69, 0.32) |
| Comparative Example 1 | HT16 | HT3 | HT12 | EM17 | Comparative compound 1-B | ET17 | ET5 | 4.4 | (0.65, 0.34) | cathode) was set to 3 mm². Subsequently, the cleaned substrate on which the electrode had been formed and materials were placed in a vacuum evaporation system (manufactured by ULVAC, Inc.), and the system was evacuated to a pressure of $1.33\times10^{-4}$ Pa ($1\times10^{-6}$ Torr) and then UV/ozone cleaning was performed. Subsequently, layers shown in Table 9 were formed. Lastly, sealing was performed in a nitrogen atmosphere.

TABLE 9

|  | Material |  | Thickness (nm) |
|---|---|---|---|
| Cathode | Mg<br>Ag | Weight ratio<br>Mg:Ag = 50:50 | 10 |
| Electron injection layer (EIL) | LiF |  | 1 |
| Electron transport layer (ETL) | ET2 |  | 30 |
| Hole blocking layer (HBL) | ET12 |  | 70 |
| Second light-emitting layer (2nd EML) | Second host | EM1 | Weight ratio EM1:BD5 = 99.4:0.6 | 10 |
|  | Second guest (blue dopant) | BD5 |  |  |
| First light-emitting layer (1st EML) | First host | EM1 | Weight ratio EM1:A8:GD8 = 96.7:0.3:3.0 | 10 |
|  | First guest (red dopant) | A8 |  |  |
|  | Third guest (green dopant) | GD8 |  |  |
| Electron blocking layer (EBL) | HT7 |  | 10 |
| Hole transport layer (HTL) | HT2 |  | 20 |
| Hole injection layer (HIL) | HT16 |  | 5 |

The characteristics of the obtained element were measured and evaluated. The obtained element exhibited good white-light emission. The chromaticity coordinates of red after transmission through an RGB color filter were estimated from the obtained white-light emission spectrum. The chromaticity coordinates of red in sRGB were (0.70, 0.32).

Examples 32 to 37 and Comparative Example 2

Organic light-emitting elements were produced in the same manner as in Example 31, except that the compounds in Example 31 were appropriately changed to those in Table 10. The characteristics of the obtained elements were measured and evaluated in the same manner as in Example 31. Table 10 shows the measurement results.

TABLE 10

|  | 1st EML | | | 2nd EML | | Chromaticity |
|---|---|---|---|---|---|---|
|  | First host | First guest | Third guest | Second host | Second guest | coordinates of red (x, y) |
| Example 32 | EM1 | A11 | GD8 | EM1 | BD5 | (0.68, 0.32) |
| Example 33 | EM5 | B3 | GD8 | EM1 | BD4 | (0.69, 0.32) |
| Example 34 | EM1 | C1 | GD9 | EM5 | BD7 | (0.69, 0.32) |
| Example 35 | EM5 | C3 | GD4 | EM5 | BD5 | (0.69, 0.31) |
| Example 36 | EM1 | C7 | GD7 | EM1 | BD6 | (0.69, 0.31) |
| Example 37 | EM11 | C11 | GD4 | EM11 | BD6 | (0.70, 0.30) |
| Comparative Example 2 | EM1 | Comparative compound 1-A | GD8 | EM1 | BD5 | (0.66, 0.34) |

As is clear from Table 10, the chromaticity coordinates of red in Comparative Example 2 are (0.66, 0.34). The white-light-emitting elements according to an embodiment of the present disclosure tend to achieve a color reproduction range wider than the color reproduction range of sRGB. This is because the compound according to an embodiment of the present disclosure emits red light having a longer wavelength.

According to the present disclosure, an organic compound in which the basic skeleton itself can emit red light with a high color purity can be provided.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-102197, filed May 31, 2019, which is hereby incorporated by reference herein in its entirety.

What is claimed is:

1. An organic compound represented by formula (1):

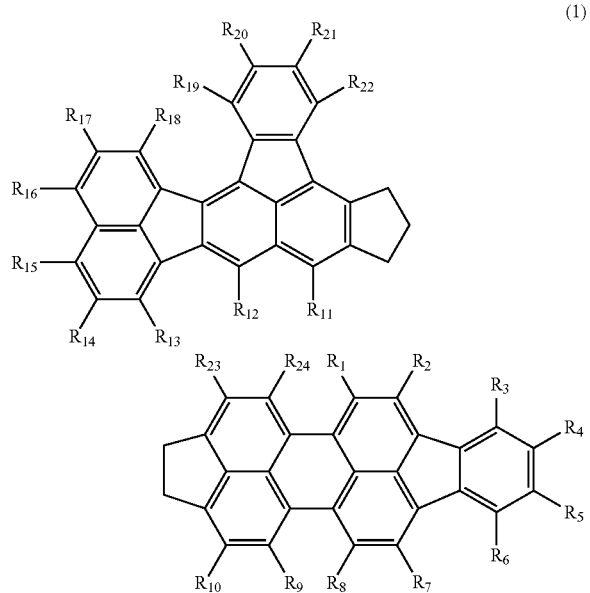

(1)

wherein $R_1$ to $R_{24}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

2. The organic compound according to claim 1, wherein $R_1$ to $R_{24}$ are each independently selected from the group consisting of a hydrogen atom, a substituted or unsubstituted alkyl group, and a substituted or unsubstituted aryl group.

3. The organic compound according to claim 1, wherein at least one of $R_{11}$ and $R_{12}$ is selected from the group consisting of a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

4. The organic compound according to claim 1, wherein at least one of $R_{11}$ and $R_{12}$ is selected from the group consisting of a substituted or unsubstituted alkyl group and a substituted or unsubstituted aryl group.

5. The organic compound according to claim 1, wherein at least one of $R_{11}$ and $R_{12}$ is an aryl group having a substituent.

6. The organic compound according to claim 5, wherein the aryl group has a substituent at an ortho position thereof.

7. The organic compound according to claim 1, wherein at least one of $R_{11}$ and $R_{12}$ is a substituted or unsubstituted phenyl group.

8. An organic light-emitting element comprising:
an anode;
a cathode; and
an organic compound layer disposed between the anode and the cathode,
wherein the organic compound layer includes a layer containing the organic compound according to claim 1.

9. The organic light-emitting element according to claim 8, wherein the layer containing the organic compound is a light-emitting layer.

10. The organic light-emitting element according to claim 9,
wherein the organic compound layer further includes another light-emitting layer disposed together with the light-emitting layer so as to form a multilayer structure, and
the other light-emitting layer emits light having a color different from a color of light emitted from the light-emitting layer.

11. The organic light-emitting element according to claim 10, wherein the organic light-emitting element emits white light.

12. A display apparatus comprising a plurality of pixels,
wherein the plurality of pixels include the organic light-emitting element according to claim 8 and an active element connected to the organic light-emitting element.

13. The display apparatus according to claim 12, further comprising a color filter.

14. A photoelectric conversion apparatus comprising:
an optical unit including a plurality of lenses;
an image pickup element that receives light which has passed through the optical unit; and
a display unit,
wherein the display unit displays information captured by the image pickup element, and
the display unit includes the display apparatus according to claim 12.

15. An electronic apparatus comprising:
a housing;
a communication unit that communicates with an external unit; and
a display unit,
wherein the display unit is the display apparatus according to claim 12.

16. A lighting apparatus comprising:
a light source; and
a light diffusion unit or an optical filter,
wherein the light source includes the organic light-emitting element according to claim 8.

17. A moving object comprising:
a body; and
a lighting fixture disposed on the body,
wherein the lighting fixture includes the organic light-emitting element according to claim 8.

18. An exposure light source for an electrophotographic image forming apparatus, comprising the organic light-emitting element according to claim 8.

* * * * *